(12) United States Patent
Meerpoel et al.

(10) Patent No.: US 7,169,796 B2
(45) Date of Patent: Jan. 30, 2007

(54) POLYARYLCARBOXAMIDES USEFUL AS LIPID LOWERING AGENTS

(75) Inventors: Lieven Meerpoel, Beerse (BE); Peter Walter Maria Roevens, Malle (BE); Leo Jacobus Jozef Backx, Arendonk (BE); Louis Jozef Elisabeth Van der Veken, Vosselaar (BE); Marcel Viellevoye, Breda (NL)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/029,956

(22) Filed: Jan. 5, 2005

(65) Prior Publication Data

US 2005/0159402 A1    Jul. 21, 2005

Related U.S. Application Data

(62) Division of application No. 10/363,665, filed as application No. PCT/EP01/09926 on Aug. 27, 2001, now Pat. No. 6,878,724.

(30) Foreign Application Priority Data

Sep. 4, 2000    (EP) ................... 00203067

(51) Int. Cl.
    A61K 31/445    (2006.01)
    C07D 211/14    (2006.01)
    C07D 401/10    (2006.01)

(52) U.S. Cl. .................... 514/317; 546/192
(58) Field of Classification Search ............ 514/317; 546/192
    See application file for complete search history.

(56) References Cited

U.S. PATENT DOCUMENTS

| | | | |
|---|---|---|---|
| 3,910,930 A | 10/1975 | Janssen et al. | |
| 3,929,801 A | 12/1975 | Janssen et al. | |
| 4,329,348 A | 5/1982 | Huebner | |
| 4,470,989 A | 9/1984 | Henning et al. | |
| 5,137,901 A | 8/1992 | Junge et al. | |
| 5,371,094 A | 12/1994 | Heine et al. | |
| 5,492,918 A | 2/1996 | Wild et al. | |
| 5,541,199 A | 7/1996 | Mewshaw | |
| 5,696,136 A | 12/1997 | Heine et al. | |
| 5,760,246 A | 6/1998 | Biller et al. | |
| 5,827,875 A | 10/1998 | Dickson, Jr. et al. | |
| 5,919,795 A | 7/1999 | Chang et al. | |
| 5,965,577 A | 10/1999 | Tino | |
| 5,968,950 A | 10/1999 | Quallich et al. | |
| 6,133,277 A | 10/2000 | Wigerinck et al. | |
| 2004/0014971 A1 | 1/2004 | Meerpoel et al. | |
| 2004/0019051 A1 | 1/2004 | Van Emelen et al. | |

FOREIGN PATENT DOCUMENTS

| CA | 2091102 | | 9/1993 |
|---|---|---|---|
| CA | 2091102 | A1 | 9/1993 |
| EP | 0643057 | A1 | 3/1995 |
| WO | WO93/17017 | A1 | 9/1993 |
| WO | WO95/05383 | A1 | 2/1995 |
| WO | WO 96/26205 | A1 | 8/1996 |
| WO | WO96/40640 | A1 | 12/1996 |
| WO | WO 96/40640 | A1 | 12/1996 |
| WO | WO98/23593 | A1 | 6/1998 |
| WO | WO 98/27979 | A1 | 7/1998 |
| WO | WO99/29687 | A1 | 6/1999 |
| WO | WO99/66407 | A1 | 12/1999 |
| WO | WO00/32582 | A1 | 6/2000 |
| WO | WO 00/32582 | A1 | 6/2000 |
| WO | WO00/75136 | A1 | 12/2000 |
| WO | WO00/75137 | A1 | 12/2000 |
| WO | WO01/77077 | A1 | 10/2001 |
| WO | WO 01/92241 | A1 | 12/2001 |
| WO | WO01/98306 | A1 | 12/2001 |
| WO | WO02/20501 | A2 | 3/2002 |
| WO | WO02/42271 | A2 | 5/2002 |
| WO | WO02/081460 | A1 | 10/2002 |

OTHER PUBLICATIONS

Sharpe, D., et al., *Cloning and Gene Defects in Microsomal Triglyceride Transfer Protein Associated with Abetalipoproteinaemia*, Nature, Sep. 1993, vol. 365, Issue No. 6441, pp. 65-69.

Sharpe, D. et al., "Cloning and gene defects in microsomal triglyceride transfer protein associated with abetalipoproteinaemia." *Nature*, 1993, pp. 65-69, vol. 365.

Akrakawa, T. "New Aspects of Gastric Adaptive Relaxation, Reflex after Food Intake for More Food: Involvement of Capsaicin-sensitive Sensory Nerves and Nitric Oxide." *J. Smooth Muscle Res.*, 1997, pp. 81-88, vol. 33.

Wetterau, J. R. et al., "An MTP Inhibitor That Normalizes Atherogenic Lipoprotein Levels in WHHL Rabbits." *Science*, 1998, pp. 751-754, vol. 282.

PCT International Search Report dated Mar. 6, 2002 for PCT Application No. PCT/EP01/09926 which relates to U.S. Appl. No. 11/029,956.

*Primary Examiner*—Taofiq Solola

(57) ABSTRACT

Polyarylcarboxamide compounds of formula I)

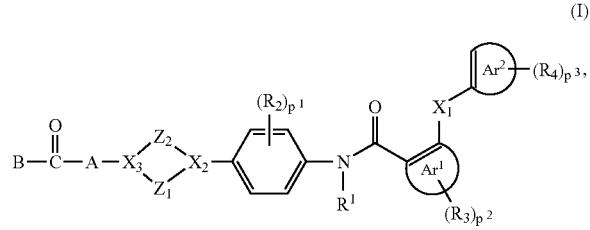

are useful as lipid lowering agents.

5 Claims, No Drawings

POLYARYLCARBOXAMIDES USEFUL AS LIPID LOWERING AGENTS

CROSS REFERENCE TO RELATED APPLICATIONS

This application is a divisional application of and claims priority to U.S. patent application No. 10/363,665 filed Feb. 28, 2003, now U.S. Pat. No. 6,878,724, which is the national stage of Application No. PCT/EP01/09926, filed Aug. 27, 2001, which application claims priority from EP 00203067.4, filed Sep. 4, 2000.

The present invention is concerned with novel polyarylcarboxamides having apolipoprotein B inhibiting activity and concomitant lipid lowering activity. The invention further relates to methods for preparing such compounds, pharmaceutical compositions comprising said compounds as well as the use of said compounds as a medicine for the treatment of hyperlipidemia, obesity and type II diabetes.

BACKGROUND OF THE INVENTION

Obesity is the cause of a myriad of serious health problems like the adult onset of diabetes and heart disease. In addition, the loss of weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia. Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis inhibitors such as HMG Co-enzyme-A reductase inhibitors. The inconvenience of administration (a granular form to be dispersed in water or orange juice) and the major side-effects (gastrointestinal discomfort and constipation) of bile acid sequestrant resins constitute major drawbacks. Fibric acid derivatives induce a moderate decrease (by 5 to 25%) of LDL cholesterol (except in hypertriglyceridemic patients in whom initially low levels tend to increase) and, although usually well tolerated, suffer from side-effects including potentiation of warfarine, pruritus, fatigue, headache, insomnia, painful reversible myopathy and stiffness in large muscle groups, impotency and impaired renal function. Nicotinic acid is a potent lipid lowering agent resulting in a 15 to 40% decrease in LDL cholesterol (and even 45 to 60% when combined with a bile acid sequestrant resin) but with a high incidence of troublesome side-effects related to the drug's associated vasodilatory action, such as headache, flushing, palpitations, tachychardia and occasional syncopes, as well as other side-effects such as gastro-intestinal discomfort, hyperucemia and impairment of glucose tolerance. Among the family of HMG Co-enzyme-A reductase inhibitors, lovastatin and simvastatin are both inactive prodrugs containing a lactone ring which is hydrolyzed in the liver to form the corresponding active hydroxy-acid derivative. Inducing a reduction of LDL cholesterol by 35 to 45%, they are generally well tolerated with alow incidence of minor side effects. However there still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of a coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, so named because it appears to be about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolaemia, familial combined hyperlipidaemia, familial hypercholesterolaemia, remnant hyperlipidaemia, chylomicronaemia syndrome and familial hypertriglyceridaemia.

Microsomal triglyceride transfer protein (hereinafter referred as MTP) is known to catalyze the transport of triglyceride and cholesteryl ester by preference to phospholipids such as phosphatidylcholine. It was demonstrated by D. Sharp et al., *Nature* (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans. MTP inhibitors have been reported in Canadian patent application No. 2,091,102 and in WO 96/26205. MTP inhibitors belonging to the class of polyarylcarboxamides have also been reported in U.S. Pat. No. 5,760,246 as well as in WO-96/40640 and WO-98/27979.

One of the goals of the present invention is to provide an improved treatment for patients suffering from obesity or atherosclerosis, especially coronary atherosclerosis and more generally from disorders which are related to atherosclerosis, such as ischaemic heart disease, peripheral vascular disease and cerebral vascular disease. Another goal of the present invention is to cause regression of atherosclerosis and inhibit its clinical consequences, particularly morbidity and mortality.

SUMMARY OF THE INVENTION

The present invention is based on the unexpected discovery that a class of novel polyarylcarboxamide compounds is acting as selective MTP inhibitors, i.e. is able to selectively block MTP at the level of the gut wall in mammals, and is therefore a promising candidate as a medicine, namely for the treatment of hyperlipidemia. The present invention additionally provides several methods for preparing such polyarylcarboxamide compounds, as well as pharmaceutical compositions including such compounds. Furthermore, the invention provides a certain number of novel compounds which are useful intermediates for the preparation of the therapeutically active polyarylcarboxamide compounds, as well as methods for preparing such intermediates. Finally, the invention provides a method of treatment of a condition selected from atherosclerosis, pancreatitis, obesity, hypercholesterolemia, hypertriglyceridemia, hyperlipidemia, diabetes and type II diabetes, comprising administering a therapeutically active polyarylcarboxamide compound to a mammal.

DETAILED DESCRIPTION OF THE INVENTION

The present invention relates to a family of novel polyarylcarboxamide compounds of formula (I)

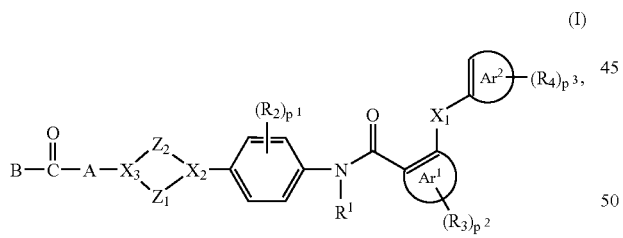

(I)

the N-oxides, the pharmaceutically acceptable addition salts and the stereochemically isomeric forms thereof, wherein $Z_1$ is selected from $(CH_2)_n$ wherein n is 1 to 3, $CH_2CH_2O$ and $OCH_2CH_2$;

$Z_2$ is $(CH_2)_m$ wherein m is 1 or 2;

$X_1$ represents O, $CH_2$, CO, NH, $CH_2O$, $OCH_2$, $CH_2S$, $SCH_2$ or a direct bond;

$X_2$ and $X_3$ are each independently selected from CH, N and a $sp^2$ carbon atom;

$R_1$ is hydrogen or $C_{1-4}$alkyl;

$Ar^1$ is an aromatic ring selected from phenyl, naphthalenyl, pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl and thienyl, optionally substituted with one or two $R_3$ substituents;

$Ar^2$ is an aromatic ring selected from phenyl, naphthalenyl, pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl and thienyl, optionally substituted with one, two or three $R_4$ substituents;

each $R_2$ and $R_3$ is independently selected from $C_{1-4}$alkyl, $C_{1-4}$alkyloxy, halo, trifluoromethyl;

each $R_4$ is independently selected from $C_{1-4}$alkyl, $C_{1-4}$alkyloxy, halo, hydroxy, mercapto, cyano, nitro, $C_{1-4}$alkylthio or polyhalo$C_{1-6}$alkyl, amino, $C_{1-4}$alkylamino and di($C_{1-4}$alkyl)amino;

$p^1$ and $p^2$ are each 0 to 2;

$p^3$ is 0 to 3;

$X_1$ and $R_4$ taken together with the aromatic rings $Ar^1$ and $Ar^2$ to which they are attached may form a fluoren-1-yl or a fluoren-4-yl group;

A represents a $C_{1-6}$alkanediyl substituted with one or two groups selected from aryl, heteroaryl and $C_{3-10}$cycloalkyl; or when $X_3$ is CH, A may also represent a nitrogen atom substituted with hydrogen, $C_{1-10}$alkyl, aryl, heteroaryl, aryl$C_{1-10}$alkyl, heteroaryl$C_{1-10}$alkyl or $C_{3-10}$ cycloalkyl;

B represents hydrogen; $C_{1-10}$alkyl; aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkoxycarbonyl, $C_{1-10}$alkylaminocarbonyl and di($C_{1-10}$alkyl)aminocarbonyl; aryl$C_{1-10}$alkyl; heteroaryl $C_{1-10}$alkyl; $C_{3-10}$cycloalkyl; polyhalo$C_{1-6}$alkyl; $C_{3-6}$ alkenyl; $C_{3-6}$ alkynyl; $NR_6R_7$; or $OR_8$;

$R_6$ and $R_7$ each independently represent hydrogen, $C_{1-10}$alkyl, aryl or heteroaryl each optionally substituted with a group selected from halo, cyano, $C_{1-4}$ alkyloxy, amino, $C_{1-10}$alkylamino, di($C_{1-10}$alkyl) amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl, heteroaryl$C_{1-10}$alkyl, $C_{3-10}$cycloalkyl, $C_{7-10}$polycycloalkyl, polyhalo$C_{1-6}$alkyl, $C_{3-8}$alkenyl, $C_{3-8}$ alkynyl, fused benzo-$C_{5-8}$cycloalkyl, and wherein $R_6$ and $R_7$ taken together with the nitrogen atom to which they are attached may form a $C_{4-8}$ saturated heterocyclic radical; and $R_8$ represents $C_{1-10}$alkyl, aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl; heteroaryl$C_{1-10}$alkyl; $C_{3-10}$cycloalkyl; $C_{7-10}$ polycycloalkyl; polyhalo$C_{1-6}$alkyl; $C_{3-8}$ alkenyl; $C_{3-8}$alkynyl; or fused benzo-$C_{5-8}$cycloalkyl.

Unless otherwise stated, as used in the foregoing definitions and hereinafter:

halo is generic to fluoro, chloro, bromo and iodo;

$C_{1-4}$alkyl defines straight and branched chain saturated hydrocarbon radicals having from 1 to 4 carbon atoms such as, for example, methyl, ethyl, propyl, n-butyl, 1-methylethyl, 2-methylpropyl, 1,1-dimethylethyl and the like;

$C_{1-6}$alkyl is meant to include $C_{1-4}$alkyl (as hereinabove defined) and the higher homologues thereof having 5 or 6 carbon atoms, such as for instance 2-methylbutyl, n-pentyl, dimethylpropyl, n-hexyl, 2-methylpentyl, 3-methylpentyl and the like;

$C_{1-10}$alkyl is meant to include $C_{1-6}$alkyl (as hereinabove defined) and the higher homologues thereof having 7 to 10 carbon atoms, such as for instance heptyl, ethylhexyl, octyl, nonyl, decyl and the like;

$C_{3-10}$cycloalkyl is generic to cyclopropyl, cyclobutyl, cyclopentyl, cyclohexyl, cycloheptyl, cyclooctyl, cyclononyl and cyclodecyl;

polyhalo$C_{1-6}$alkyl is defined as polyhalosubstituted $C_{1-6}$alkyl, in particular $C_{1-6}$alkyl (as hereinabove defined) substituted with 2 to 13 halogen atoms such as difluoromethyl, trifluoromethyl, trifluoroethyl, octafluoropentyl and the like;

aryl is defined as mono- and polyaromatic groups such as phenyl or naphthalenyl optionally substituted with one to three substituents each independently selected from nitro, azido, cyano, halo, hydroxy, $C_{1-6}$ alkyl, $C_{3-7}$cycloalkyl, $C_{1-4}$alkyloxy, polyhalo$C_{1-6}$alkyl, amino, mono- or di($C_{1-6}$alkyl)amino;

heteroaryl is defined as mono- and polyheteroaromatic groups such as those including one or more heteroatoms selected from nitrogen, oxygen, sulfur and phosphorus, in particular pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl and the like, including all possible isomeric forms thereof;

$C_{3-6}$alkenyl defines straight and branched chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl, 3-hexenyl, 2-hexenyl and the like;

$C_{3-6}$alkynyl defines straight and branched chain hydrocarbon radicals containing one triple bond and having from 3 to 6 carbon atoms such as, for example, 2-propynyl, 3-butynyl, 2-butynyl, 2-pentynyl, 3-pentynyl, 3-methyl-2-butynyl, 3-hexynyl, 2-hexynyl and the like;

$C_{4-8}$cycloalkenyl defines cyclic hydrocarbon radicals containing one double bond and having from 4 to 8 carbon atoms such as, for example cyclobutenyl, cyclopentenyl, cyclohexenyl, cycloheptenyl, cyclooctenyl and the like;

fused benzo-$C_{5-8}$cycloalkyl defines radicals such as, for instance, indanyl, 1,2,3,4-tetrahydronaphthalenyl, fluorenyl and the like;

$C_{7-10}$ polycycloalkyl defines radicals having from 7 to 10 carbon atoms such as, for instance, norbornyl;

$C_{1-6}$alkylamino defines primary amino radicals having from 1 to 6 carbon atoms such as, for example, methylamino, ethylamino, propylamino, iso propylamino, butylamino, isobutylamino and the like;

di($C_{1-6}$ alkyl)amino defines secondary amino radicals having from 1 to 6 carbon atoms such as, for example, dimethylamino, diethylamino, dipropylamino, di-isopropylamino, N-methyl-N'-ethylamino, N-ethyl-N'-propylamino and the like;

$C_{1-6}$alkylthio defines a $C_{1-6}$alkyl group attached to a sulfur atom, such as methylthio, ethylthio, propylthio, isopropylthio, butylthio and the like;

$C_{1-6}$acyl defines a $C_{1-6}$alkyl group attached to a carbonyl group such as, for instance acetyl, propionyl, butyryl, isobutyryl and the like.

The pharmaceutically acceptable addition salts as mentioned hereinabove are meant to include the therapeutically active non-toxic acid addition salt forms which the compounds of formula (I) are able to form and which may conveniently be obtained by treating the base form of such compounds with an appropriate acid. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic, pamoic and the like. Conversely the salt form can be converted by treatment with an appropriate alkali into the free base form.

The term pharmaceutically acceptable addition salt as used hereinabove also includes the solvates which the compounds of formula (I) as well as their salts are able to form, such as for example hydrates, alcoholates and the like.

The N-oxide forms of the compounds of formula (I), are meant to include those compounds wherein one or more nitrogen atoms are oxidized, using methods well known in the art for converting a trivalent nitrogen into its N-oxide form. Said N-oxidation reaction may usually be carried out by reacting the compound of formula (I) with 3-phenyl-2-(phenylsulfonyl)oxaziridine or with an appropriate organic or inorganic peroxide in at least one suitable solvent. Appropriate inorganic peroxides include for example hydrogen peroxide and alkali metal or alkaline-earth metal peroxides, e.g. sodium or potassium peroxides. Appropriate organic peroxides may comprise peroxy acids such as, for example benzenecarboperoxoic acid or halo substituted benzenecarboperoxoic acid (e.g. 3-chlorobenzene-carboperoxoic acid), peroxoalkanoic acids (e.g. peroxoacetic acid) and alkylhydroperoxides (e.g. tert-butyl hydroperoxide). Suitable solvents for this reaction include for instance water, lower alcohols (e.g. ethanol and the like), hydrocarbons (e.g. toluene), ketones (e.g. 2-butanone), halogenated hydrocarbons (e.g. dichloromethane) and mixtures of such solvents.

The polyarylcarboxamide compounds of formula (I) may have at least one chiral center in the A group and/or the B group and/or the cyclic group including $X_2$ and $X_3$.

The term "stereochemically isomeric forms" as used hereinbefore defines all the possible isomeric forms which the compounds of formula (I) may possess. Unless otherwise stated, the chemical designation of compounds denotes the mixture of all possible stereochemically isomeric forms, said mixtures containing all diastereomers and enantiomers of the basic molecular structure. More particularly, stereogenic centers may have either the R— or S-configuration; substituents on bivalent cyclic saturated radicals may have either the cis- or trans-configuration. The same definition applies to the various novel intermediates, as described herein, which are used to prepare the polyarylcarboxamide compounds of formula (I).

Pure stereoisomeric forms of the said compounds and intermediates are defined as isomers substantially free of other enantiomeric or diastereomeric forms of the same basic molecular structure. In particular, the term "stereoisomerically pure" or "chirally pure" relates to compounds or intermediates having a stereoisomeric excess of at least 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Consequently, if a mixture of enantiomers is obtained during any of the following preparation methods, it can be separated by liquid chromatography using a suitable chiral stationary phase. Suitable chiral stationary phases are, for example, polysaccharides, in particular cellulose or amylose derivatives. Commercially available polysaccharide based chiral stationary phases are ChiralCel™ CA, OA, OB, OC, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like.

The terms cis and trans are used herein in accordance with Chemical Abstracts nomenclature and refer to the position of the substituents on a ring moiety.

The absolute stereochemical configuration of the polyarylcarboxamide compounds of formula (I) and of the intermediates used in their preparation may easily be determined by those skilled in the art while using well-known methods such as, for example, X-ray diffraction.

Furthermore, some polyarylcarboxamide compounds of formula (I) and some of the intermediates used in their preparation may exhibit polymorphism. It is to be understood that the present invention encompasses any polymorphic forms possessing properties useful in the treatment of the conditions noted hereinabove.

A group of interesting compounds consists of those compounds of formula (I) wherein one or more of the following restrictions apply:
a) $R^1$ is hydrogen;
b) $R^2$ is hydrogen or $C_{1-4}$alkyl;
c) $R^3$ is hydrogen or $C_{1-4}$alkyl;
d) $R^4$ is hydrogen, $C_{1-4}$alkyl or trifluoromethyl;
e) $p^1$ is 1;
f) $p^2$ is 1;
g) $p^3$ is 1;
h) the bivalent radical A is $C_{1-6}$alkanediyl substituted with one aryl group, in particular A is a methylene group substituted with phenyl;
i) B is $C_{1-4}$alkyloxy, or $C_{1-10}$alkylamino.

Interesting compounds are those compounds of formula (I) wherein $Z_1$, $Z_2$, $X_2$ and $X_3$ taken together form a six-membered heterocycle.

Particular compounds are those compounds of formula (I) wherein radical B represents methyloxy or ethyloxy.

Other particular compounds are those compounds of formula (I) wherein $R_2$ and/or $R_3$ are/is $C_{1-4}$alkyl.

Yet other particular compounds are those compounds of formula (I) wherein $R_4$ is $C_{1-4}$alkyl or trifluoromethoxy.

More preferred compounds are those particular compounds of formula (I) wherein $Z_1$, $Z_2$, $X_2$ and $X_3$ taken together form a piperidine or piperazine group and $X_1$ is a direct bond.

More preferred compounds of formula (I) are those compounds wherein $R_2$ and $R_3$ are each hydrogen and $R_4$ is hydrogen, trifluoromethyl, chloro or tert-butyl.

Most preferred compound of formula (I) are

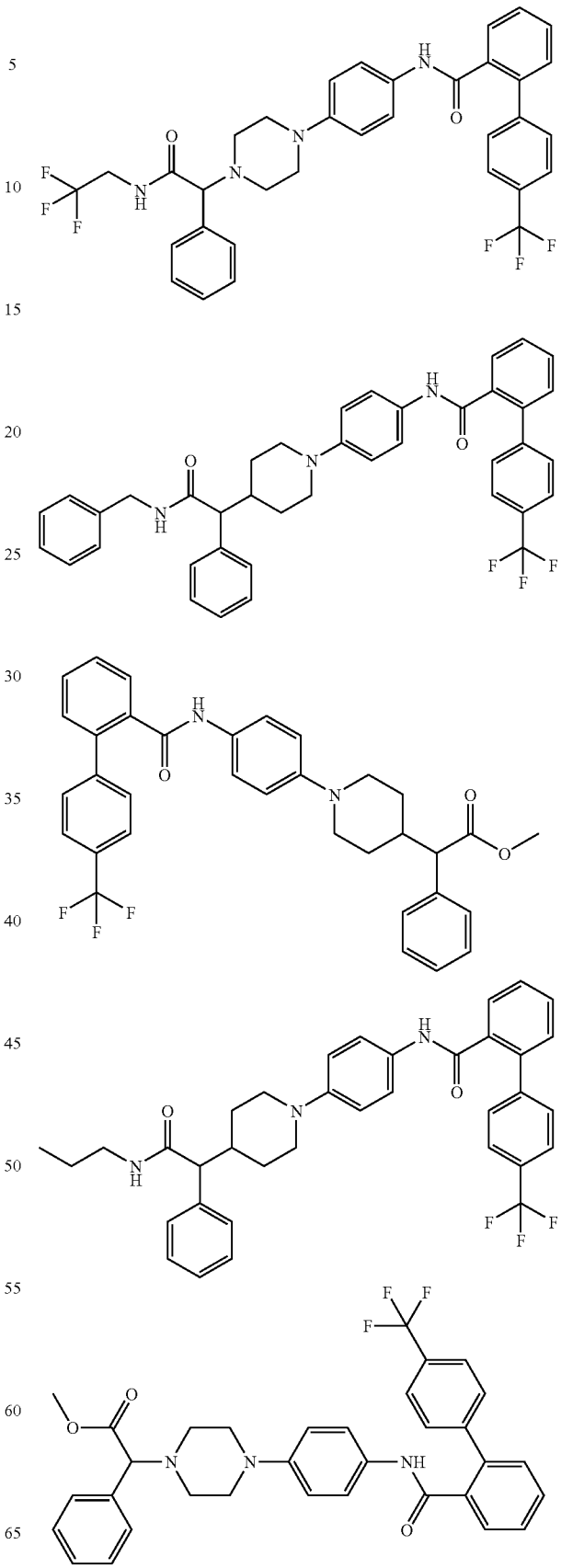

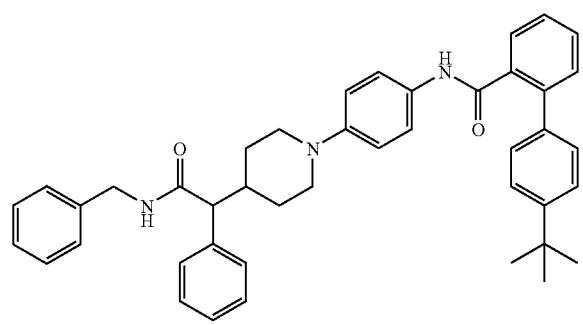
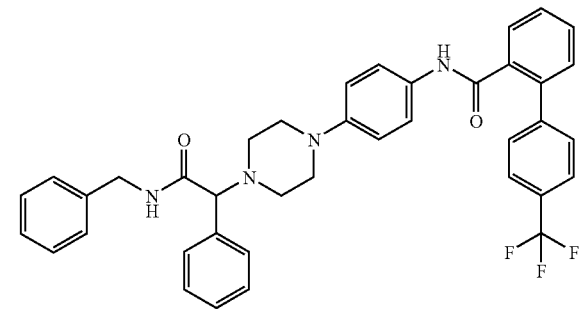

-continued
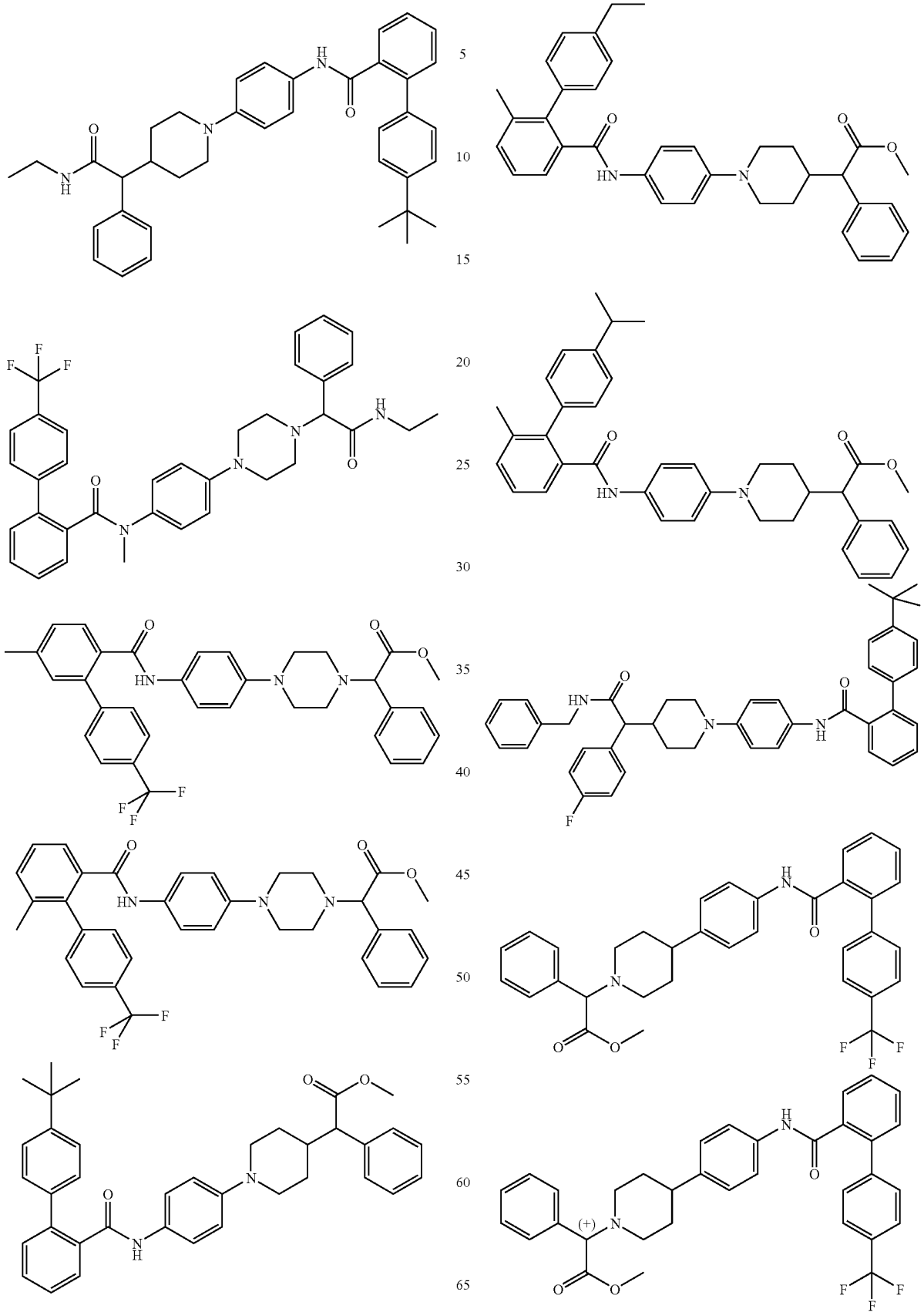

-continued

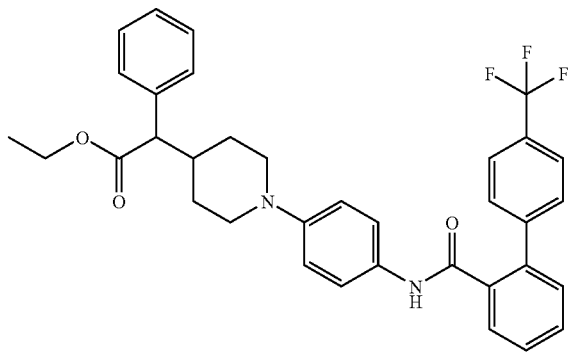

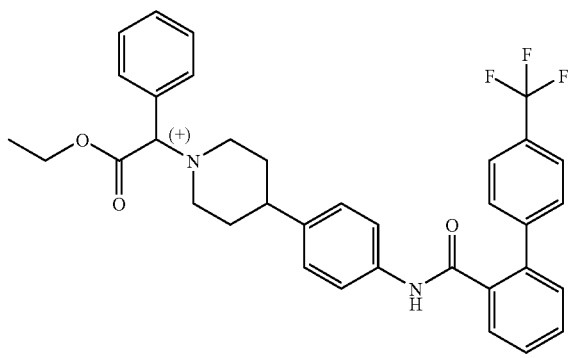

and the stereoisomeric forms, the pharmaceutically acceptable acid addition salts, or the N-oxides thereof.

One advantage of the present invention is the easiness with which the compounds of formula (I) can be manufactured by a high number of different processes. Some of these processes will now be described in details, without pretending to provide an exhaustive list of the methods for preparing the said compounds.

A first process for preparing a polyarylcarboxamide compound according to this invention is a process wherein an intermediate phenylene amine having the formula

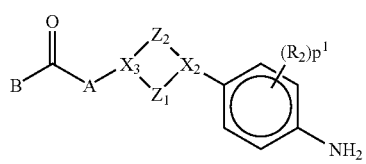
(II)

wherein $Z_1$, $Z_2$, $X_2$, $X_3$, $p^1$, $R_1$, $R_2$, A and B are as defined in formula (I), is reacted with a polyarylcarboxylic acid or halide having the formula (III),

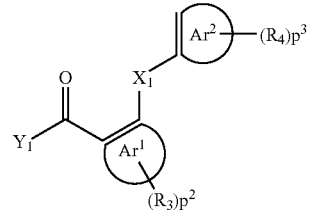
(III)

wherein $X_1$, $Ar^1$, $Ar^2$, $p^2$, $p^3$, $R_3$ and $R_4$ are as defined in formula (I) and $Y_1$ is selected from hydroxy and halo, in at least one reaction-inert solvent and optionally in the presence of a suitable base, the said process further optionally comprising converting a compound of formula (I) into an addition salt thereof, and/or preparing stereochemically isomeric forms thereof. In case $Y_1$ is hydroxy, it may be convenient to activate the biphenylcarboxylic acid of formula (III) by adding an effective amount of a reaction promoter. Non-limiting examples of such reaction promoters include carbonyldiimidazole, diimides such as N,N'-dicyclohexylcarbodiimide or 1-(3-dimethylaminopropyl)-3-ethylcarbodiimide, and functional derivatives thereof. For this type of acylation procedure, it is preferred to use a polar aprotic solvent such as, for instance, methylene chloride. Suitable bases for carrying out this first process include tertiary amines such as triethylamine, triisopropylamine and the like. Suitable temperatures for carrying out the first process of the invention typically range from about 20° C. to about 140° C., depending on the particular solvent used, and will most often be the boiling temperature of the said solvent.

A second process for preparing a polyarylcarboxamide compound according to this invention, wherein $X_3$ is nitrogen, is a process wherein an intermediate having the formula

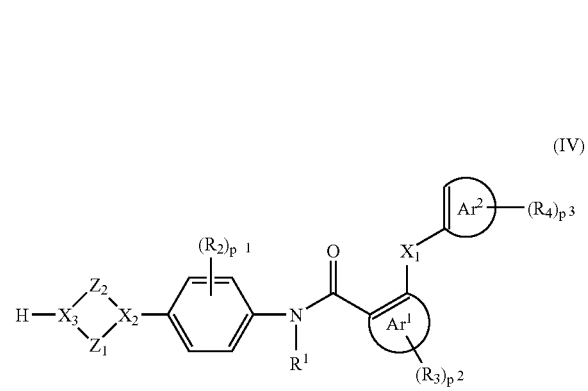
(IV)

wherein $Z_1$, $Z_2$, $X_1$, $X_2$, $p^1$, $p^2$, $p^3$, $Ar^1$, $Ar^2$, $R_1$, $R_2$, $R_3$ and $R_4$ are as defined in formula (I) and $X_3$ is nitrogen, is reacted with a reactant having the formula (V)

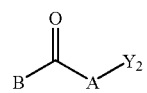
(V)

wherein A and B are as defined in formula (I) and $Y_2$ is selected from halo, tosyloxy, mesyloxy, naphtylsulfonyloxy, or -A-$Y_2$ is R'$_5$COR$_5$, wherein R$_5$ and R'$_5$ are such that the radical R'$_5$CHR$_5$ is encompassed by the definition of A in formula (I), in at least one reaction-inert solvent and optionally in the presence of at least one suitable nucleophilic substitution activator and/or a suitable base, the said process further optionally comprising converting a compound of formula (I) into an addition salt thereof, and/or preparing stereochemically isomeric forms thereof. When $Y_2$ is halo, the alkylation coupling procedure may for instance be effected in the presence of sodium or potassium carbonate or a tertiary amine such as triethylamine or diisopropylethylamine in a solvent such as dimethylformamide or methylisopropylketone and optionally in the presence of a catalytic amount of potassium iodide in order to enhance nucleophilic substitution. Intermediates of formula (IV) wherein $X_3$ is nitrogen may also be reductively N-alkylated by means of an aldehyde or a ketone of formula (V) wherein -A-$Y_2$ is R'$_5$COR$_5$, thus forming compounds of formula (I). Said reductive N-alkylation may be performed in a reaction-inert solvent such as for example toluene, methanol, tetrahydrofuran or a mixture thereof, and in the presence of a reducing agent. Non-limiting examples of such reducing agents include hydrogen and borohydrides, e.g. sodium borohydride, zinc borohydride, lithium borohydride, sodium cyanoborohydride, triacetoxy borohydride and the like. When a borohydride is used as the reducing agent, it may be convenient to perform the N-alkylation in the additional presence of a catalyst. Non-limiting. examples of such catalysts include transition metal alkoxides, e.g. titanium (IV)isopropoxide, titanium(IV)-n-butoxide and the like, as disclosed in *J. Org. Chem.* (1990), 55:2552–4. When hydrogen is used as the reducing agent, it may be convenient to perform the N-alkylation in the additional presence of a catalyst. Non-limiting examples of catalysts suitable for this purpose include a noble metal supported on a carrier such as for instance palladium-on-charcoal or platinum-on-charcoal. The formation of a Schiff base in a first step of the said reductive N-alkylation reaction may be further enhanced by the additional presence of a suitable reagent such as aluminium terbutoxide, calcium oxide, calcium hydride and the like. An appropriate catalyst-poison, e.g. thiophene, butanethiol, quinoline sulfur or the like, may also be added to the reaction mixture in order to prevent undesired hydrogenation of certain functional groups in the reactants and/or the reaction product. Stirring and optionally elevated temperature and/or pressure may further enhance the rate of such a reaction.

A third process for preparing a polyarylcarboxamide compound of the invention is a process wherein an intermediate having the formula

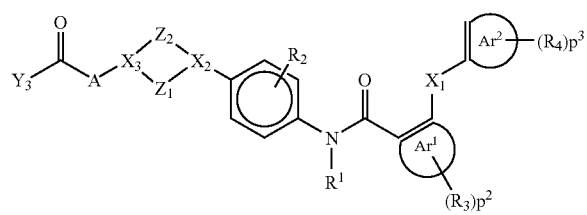

(VI)

wherein $Z_1$, $Z_2$, $X_1$, $X_2$, $X_3$, $p^1$, $p^2$, $p^3$, Ar$^1$, Ar$^2$, $R_1$, $R_2$, $R_3$, $R_4$ and A are as defined in formula (I) and $Y_3$ is selected from halo and hydroxy, is reacted with a reactant of the formula BH, wherein B is NR$_6$R$_7$ or OR$_8$ and R$_6$, R$_7$ and R$_8$ are as defined in formula (I); in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof. In case $Y_3$ is hydroxy, it may be convenient to activate the carboxylic acid of formula (VI) by adding an effective amount of a reaction promoter. Non-limiting examples of such reaction promoters include carbonyldiimidazole, diimides such as N,N'-dicyclohexylcarbodiimide or 1-(3-dimethylaminopropyl)-3-ethylcarbo-diimide, and functional derivatives thereof. In case a chirally pure reactant of formula (V) is used, a fast and enantiomerization-free reaction of the intermediate of formula (VI) with the said reactant may be performed in the further presence of an effective amount of a compound such as hydroxybenzotriazole, benzotriazolyloxytris (dimethylamino)phosphonium hexafluorophosphate, tetrapyrrolidinophosphonium hexafluorophosphate, bromotripyrrolidinophosphonium hexafluorophosphate, or a functional derivative thereof, such as disclosed by D. Hudson, *J. Org. Chem.* (1988), 53:617. In case $Y_3$ is hydroxy and B is OR$_8$, then the esterification reaction may conveniently be performed in the presence of an effective amount of an acid such as sulfuric acid and the like.

A fourth process for preparing a polyarylcarboxamide compound according to this invention wherein $X_3$ is nitrogen and wherein A is a group suitable for a Michael addition reaction, is a process wherein an intermediate having the formula (IV), wherein $X_3$ is nitrogen, is reacted with a reactant of the formula (VII)

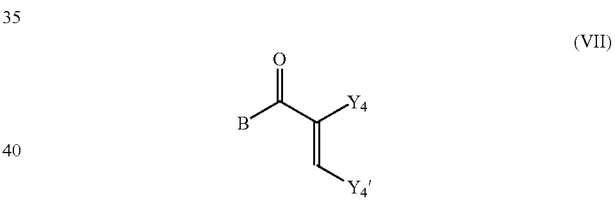

(VII)

wherein B is as defined in formula (I), and $Y_4$ and $Y'_4$ are such that the radical

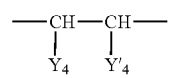

is encompassed by the definition of A in formula (I), in at least one reaction-inert solvent, the said process further optionally comprising converting a compound of formula (I) into an addition salt thereof, and/or preparing stereochemically isomeric forms thereof. The reaction-inert solvent may be, for instance, dimethylformamide or methanol and the reaction temperature may be the boiling point of the said solvent. Contrary to most of the alternative processes for preparing the polyarylcarboxamide compounds of this invention, this fourth process does not require the presence of a catalyst or otherwise coupling reagent in order to quantatively yield the target compound. A base such as sodium carbonate, potassium carbonate, cesium carbonate and the like may optionally be added to the reaction mixture. As conventionally defined in the art, A preferably is an α,β-unsaturated carbonyl compound, such as a ketone or an ester, the β carbon atom of which is susceptible of a nucleophilic attack. Non-limiting examples of groups A suitable for such a Michael addition reaction include for instance:

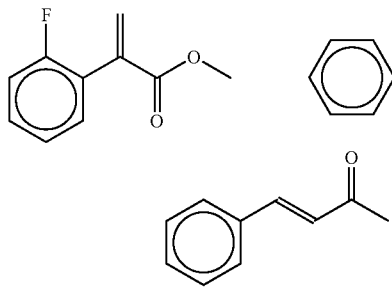

A fifth process for preparing a polyarylcarboxamide compound according to this invention is a process wherein an intermediate having the formula (VIII)

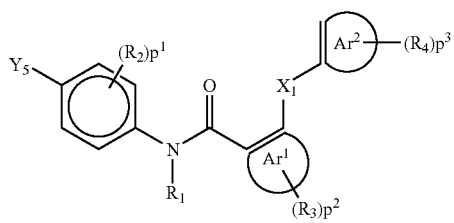

wherein $X_1$, $p^1$, $p^2$, $p^3$, $Ar^1$, $Ar^2$, $R_1$, $R_2$, $R_3$ and $R_4$ are as defined in formula (I) and $Y_5$ is selected from halo, $B(OH)_2$, alkylboronates and cyclic analogues thereof, is reacted with a reactant having the formula (IX)

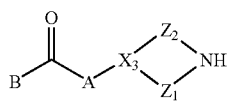

wherein $Z_1$, $Z_2$, $X_3$, A and B are as defined in formula (I), in at least one reaction-inert solvent and optionally in the presence of at least one transition metal coupling reagent and/or at least one suitable ligand, the said process further optionally comprising converting a compound of formula (I) into an addition salt thereof, and/or preparing stereochemically isomeric forms thereof. This type of reaction being known in the art as the Buchwaldt reaction, reference to the applicable metal coupling reagents and/or suitable ligands, e.g. palladium compounds such as palladium tetra(triphenylphosphine), tris(dibenzylidene-acetone dipalladium, 2,2'-bis(diphenylphosphino)-1,1'-binaphtyl and the like, may be found for instance in *Tetrahedron Letters* (1996) 37(40) 7181–7184 and *J. Am. Chem. Soc.* (1996) 118:7216. If $Y_5$ is $B(OH)_2$, an alkylboronate or a cyclic analogue thereof, then cupric acetate should be used as the coupling reagent, according to *Tetrahedron Letters* (1998) 39:2933–6.

A sixth process for preparing a polyarylcarboxamide compound according to this invention is a process wherein an intermediate having the formula (X)

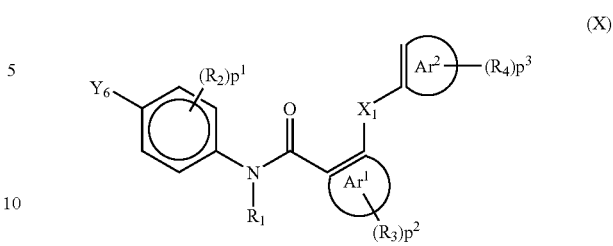

wherein $p^1$, $p^2$, $p^3$, $Ar^1$, $Ar^2$, $X_1$, $R_1$, $R_2$, $R_3$ and $R_4$ are as defined in formula (I), is reacted with a reactant having the formula (XI)

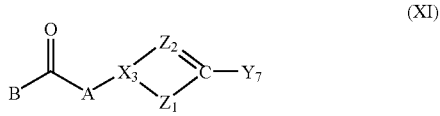

wherein $Z_1$, $Z_2$, $X_3$, A and B are as defined in formula (I), one of $Y_6$ and $Y_7$ is selected from bromo, iodo and trifluoromethylsulfonate and the other of $Y_6$ and $Y_7$ is selected from tri($C_{1-4}$alkyl) tin, $B(OH)_2$, alkylboronates and cyclic analogues thereof, in at least one reaction-inert solvent and optionally in the presence of at least one transition metal coupling reagent and/or at least one suitable ligand such as palladium associated with triphenylphosphine, triphenylarsine and the like, the said process further optionally comprising converting a compound of formula (I) into an addition salt thereof, and/or preparing stereochemically isomeric forms thereof. This type of reaction being known in the art as the Stille reaction or the Suzuki reaction, reference to the applicable transition metal coupling reagents and/or suitable ligands may be found for instance in *Syn. Letters* (1998)6,671–5, in *Chem. Rev.* (1999)99(6)1549–1581 and in The Stille Reaction (John Wiley & Sons, Inc.) ISBN 0-471-31273-8.

A seventh process for preparing a polyarylcarboxamide compound according to this invention is a process wherein an intermediate having the formula (XII)

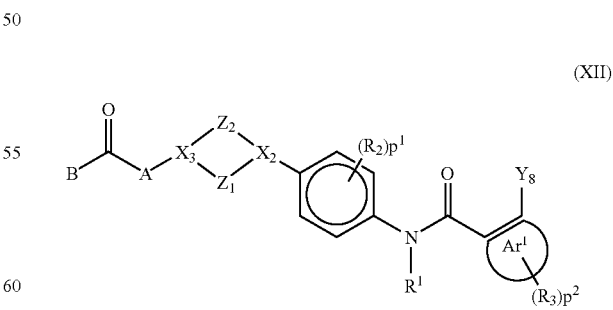

wherein $Z_1$, $Z_2$, $X_2$, $X_3$, $p^1$, $p^2$, $Ar^1$, $R_1$, $R_2$, $R_3$, A and B are as defined in formula (I) and $Y_8$ is selected from bromo, iodo and trifluoromethylsulfonate, is reacted either with an arylboric acid having the formula (XIII a)

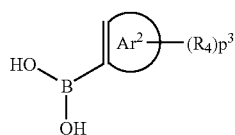

(XIII-a)

wherein $p^3$, $Ar^2$ and $R_4$ are as defined in formula (I), or with an aryl-tin reactant having the formula (XIII b)

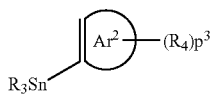

(XIII-b)

wherein $R_3$, $R_4$, $Ar^2$ and $p^3$ are as defined in formula (I), in at least one reaction-inert solvent and optionally in the presence of at least one transition metal coupling reagent and/or at least one suitable ligand, the said process further optionally comprising converting a compound of formula (I) into an addition salt thereof, and/or preparing or stereochemically isomeric forms thereof. This type of reaction being known in the art as the Stille reaction or the Suzuki reaction, reference to the applicable transition metal coupling reagents and/or suitable ligands may be found for instance in the literature cited above. Exemplary coupling reagents for this process are e.g. bis(triphenylphospine) dichloropalladium and diacetylpalladium. Exemplary reaction-inert solvents for this reaction are 1,4-dioxane, toluene, dimethylformamide, tetrahydrofuran, dimethylether and the like.

Furthermore, a process for preparing a polyarylcarboxamide compound of the formula (I) wherein B is $NR_6R_7$, from a polyarylcarboxamide compound of the formula (I) wherein B is $OR_5$ is a process comprising in a first step hydrolyzing the latter and in a second step reacting the resulting corresponding carboxylic acid with an amine having the formula $HNR_6R_7$ in at least one reaction-inert solvent and further optionally comprising converting the resulting compound of formula (I) wherein B is $NR_6R_7$ into an addition salt thereof, and/or preparing stereochemically isomeric forms thereof. The hydrolysis first step is preferably effected in an acidic-medium such as strongly concentrated hydrochloric acid and optionally in the presence of an organic solvent such as dioxane.

The compounds of formula (I) can also conveniently be prepared using solid phase synthesis techniques. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry are described in for example "The Combinatorial Index" (B. Bunin, Academic Press) and Novabiochem's 1999 Catalogue & Peptide Synthesis Handbook (Novabiochem AG, Switzerland) both incorporated herein by reference.

Furthermore, the invention provides compounds of any of the formulae (II), (III), (IV), (VI), (VIII), (X) and (XII) hereunder:

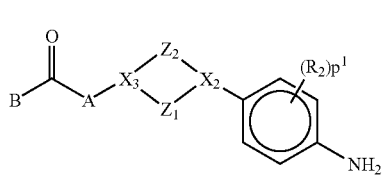

(II)

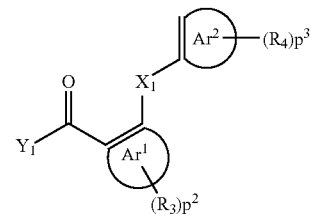

(III)

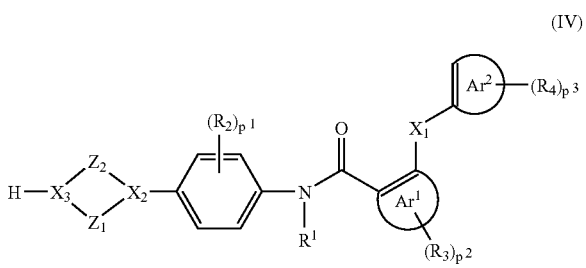

(IV)

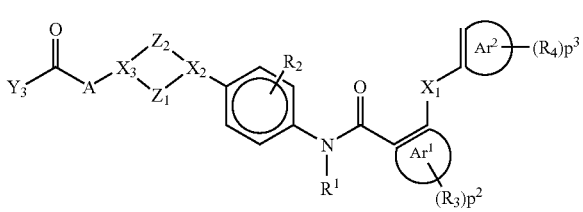

(VI)

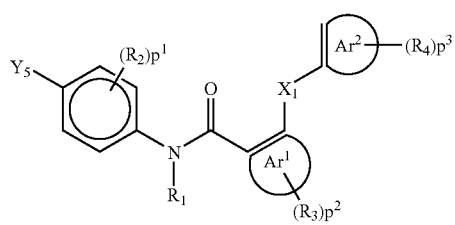

(VIII)

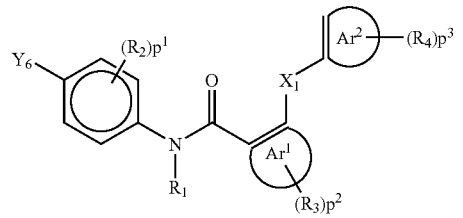

(X)

-continued

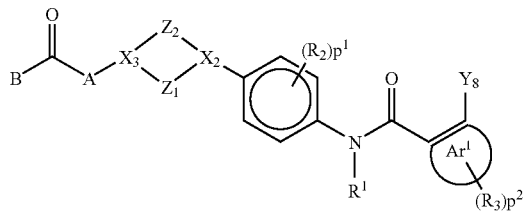

(XII)

wherein:
- $Z_1$ is selected from $(CH_2)_n$ wherein n is 1 to 3, $CH_2CH_2O$ and $OCH_2CH_2$;
- $Z_2$ is $(CH_2)_m$ wherein m is 1 or 2;
- $X_1$ represents O, $CH_2$, CO, NH, $CH_2O$, $OCH_2$, $CH_2S$, $SCH_2$ or a direct bond;
- $X_2$ and $X_3$ are each independently selected from CH, N and a sp2 carbon atom;
- $R_1$ is hydrogen or $C_{1-4}$ alkyl;
- $Ar^1$ is an aromatic ring selected from phenyl, naphthalenyl, pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl and thienyl, optionally substituted with one or two $R_3$ substituents;
- $Ar^2$ is an aromatic ring selected from phenyl, naphthalenyl, pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl and thienyl, optionally substituted with one, two or three $R_4$ substituents;
- each $R_2$ and $R_3$ is independently selected from $C_{1-4}$ alkyl, $C_{1-4}$ alkyloxy, halo and trifluoromethyl;
- each $R_4$ is independently selected from $C_{1-4}$ alkyl, $C_{1-4}$ alkyloxy, halo, hydroxy, mercapto, cyano, nitro, $C_{1-4}$ alkylthio or polyhalo$C_{1-6}$alkyl, amino, $C_{1-4}$alkylamino and di($C_{1-4}$alkyl)amino;
- $p^1$ and $p^2$ are each 0 to 2;
- $p^3$ is 0 to 3;
- $X_1$ and $R_4$ taken together with the aromatic rings to which they are attached may form a fluoren-1-yl or a fluoren-4-yl group;
- A represents a $C_{1-6}$ alkanediyl optionally substituted with one or two groups selected from aryl, heteroaryl and $C_{3-10}$ cycloalkyl; oxygen; or a direct bond;
- B represents hydrogen; $C_{1-10}$alkyl; aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkoxycarbonyl, $C_{1-10}$alkylaminocarbonyl and di($C_{1-10}$alkyl)aminocarbonyl; aryl$C_{1-10}$alkyl; heteroaryl$C_{1-10}$alkyl; $C_{3-10}$ cycloalkyl; polyhalo$C_{1-6}$alkyl; $C_{3-6}$ alkenyl; $C_{3-6}$ alkynyl; $NR_6R_7$; or $OR_8$;
- $R_6$ and $R_7$ each independently represent hydrogen, $C_{1-10}$alkyl, aryl or heteroaryl each optionally substituted with a group selected from halo, cyano, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl, heteroaryl$C_{1-10}$alkyl, $C_{3-10}$cycloalkyl, $C_{7-10}$polycycloalkyl, polyhalo$C_{1-6}$alkyl, $C_{3-8}$alkenyl, $C_{3-8}$alkynyl, fused benzo-$C_{5-8}$cycloalkyl, and wherein $R_6$ and $R_7$ taken together with the nitrogen atom to which they are attached may form a $C_{4-8}$ saturated heterocyclic radical;
- $R_8$ represents $C_{1-10}$alkyl, aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl; heteroaryl$C_{1-10}$alkyl; $C_{3-10}$cycloalkyl; $C_{7-10}$ polycycloalkyl; polyhalo$C_{1-6}$alkyl; $C_{3-8}$alkenyl; $C_{3-8}$alkynyl; or fused benzo-$C_{5-8}$ cycloalkyl;
- when $X_3$ is CH, A may also represent a nitrogen atom substituted with hydrogen, $C_{1-10}$alkyl, aryl, heteroaryl, aryl$C_{1-10}$alkyl, heteroaryl$C_{1-10}$alkyl or $C_{3-10}$cycloalkyl;
- $Y_1$ and $Y_3$ are each independently selected from hydroxy and halo;
- $Y_5$ is selected from halo, B(OH)$_2$, alkylboronates and cyclic analogues thereof; and
- $Y_6$ and $Y_8$ are each independently selected from bromo, iodo and trifluoromethylsulfonate, which are useful as intermediates for the preparation of the polyarylcarboxamide compounds of the present invention. In turn, the present invention provides methods for preparing the above-mentioned families of intermediate compounds, such as disclosed in the foregoing examples.

The polyarylcarboxamide compounds of formula (I), the N-oxide forms, the pharmaceutically acceptable salts and stereoisomeric forms thereof possess favourable apolipoprotein B inhibiting activity and concomitant lipid lowering activity. Therefore the present compounds are useful as a medicine especially in a method of treating patients suffering from hyperlipidemia, obesity, atherosclerosis or type II diabetes. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL.

The causal relationship between hypercholesterolemia—particularly that associated with increased plasma concentrations of low density lipoproteins (LDL) and very low density lipoproteins (VLDL)—and premature atherosclerosis and cardiovascular disease is well established. VLDL is secreted by the liver and contains apolipoprotein B (apo-B); these particles undergo degradation in the circulation to LDL, which transports about 60 to 70% of the total serum cholesterol. Apo-B is also the principal protein component of LDL. Increased LDL-cholesterol in serum, due to oversynthesis or decreased metabolism, is causally related to atherosclerosis. In contrast, high density lipoproteins (HDL) which contain apolipoprotein A1, have a protective effect and are inversely correlated with risk of coronary heart disease. The HDL/LDL ratio is thus a convenient method of assessing the atherogenic potential of an individual's plasma lipid profile.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylomicronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthetized by the intestine, is necessary for the assembly of chylomicrons and therefore has an obligatory role in the intestinal absorption of dietary fats. The present invention provides polyarylcarboxamide compounds which are acting as selective MTP inhibitors at the level of the gut wall.

Additionally the present invention provides pharmaceutical compositions comprising at least one pharmaceutically acceptable carrier and a therapeutically effective amount of a polyarylcarboxamide compound having the formula (I).

In order to prepare the pharmaceutical compositions of this invention, an effective amount of the particular compound, in base or addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl, p-hydroxybenzoates or sorbic acid).

Pharmaceutically-acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The polyarylcarboxamide compounds of this invention may be formulated for parenteral administration by injection, conveniently intravenous, intramuscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The polyarylcarboxamide compounds of this invention may also be formulated in rectal compositions such as suppositories or retention enemas, e.g. containing conventional suppository bases such as cocoa butter and/or other glycerides.

The polyarylcarboxamide compounds of this invention may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such inhibition may be determined readily by one skilled in the art according to standard assays, i.e. Methods of Enzymology (1981) 71:455–509. Exemplary compounds are described e.g. in U.S. Pat. No. 4,231,938 (including lovastatin), U.S. Pat. No. 4,444,784 (including simvastatin), U.S. Pat. No. 4,739,073 (including fluvastatin), U.S. Pat. No. 4,346,227 (including pravastatin), EP-A-491,226 (including rivastatin) and U.S. Pat. No. 4,647,576 (including atorvastatin).

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one skilled in the art according to standard assays, i.e. Methods of Enzymology (1985) 110:19–26. Exemplary compounds are described e.g. in U.S. Pat. No. 5,120,729 relating to beta-lactam derivatives, U.S. Pat. No. 5,064,856 relating to spiro-lactone derivatives and U.S. Pat. No. 4,847,271 relating to oxetane compounds.

Any HMG-CoA reductase gene expression inhibitor may be used as the second compound in the combination therapy aspect of this invention. These agents may be HMG-CoA reductase trancription inhibitors that block the transcription of DNA or translation inhibitors that prevent translation of mRNA coding for HMG-CoA reductase into protein. Such inhibitors may either affect trancription or translation directly or may be biotransformed into compounds having the above-mentioned attributes by one or more enzymes in the cholesterol biosynthetic cascade or may lead to accumulation of a metabolite having the above-mentioned activities. Such regulation may be determined readily by one skilled in the art according to standard assays, i.e. Methods of Enzymology (1985) 110:9–19. Exemplary compounds are described e.g. in U.S. Pat. No. 5,041,432 and E. I. Mercer, *Prog. Lip. Res.* (1993) 32:357–416.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL. Exemplary compounds are described e.g. in U.S. Pat. No. 5,512,548, in *J. Antibiot.* (1996) 49(8):815–816 and *Bioorg. Med. Chem. Lett.* (1996) 6:1951–1954.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase. Such inhibition may be determined readily by one skilled in the art according to standard assays, i.e. the method of Heider et al., *Journal of Lipid Research* (1983) 24:1127. Exemplary compounds are described e.g. in U.S. Pat. No. 5,510,379, in WO 96/26948 and WO 96/10559.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase. Such inhibition may be determined readily by one skilled in the art according to standard methods, i.e. Methods of Enzymology (1985) 110:359–373. Exemplary compounds are described e.g. in EP-A-567,026, in EP-A-645,378 and in EP-A-645,377.

Those of skill in the treatment of hyperlipidemia will easily determine. the therapeutically effective amount of a polyarylcarboxamide compound of this invention from the test results presented hereinafter. In general it is contemplated that a therapeutically effective dose will be from about 0.001 mg/kg to about 5 mg/kg of body weight, more preferably from about 0.01 mg/kg to about 0.5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular polyarylcarboxamide compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the polyarylcarboxamide compounds of the instant invention. The effective daily amount ranges mentioned hereinabove are therefore only guidelines.

Experimental Part

In the procedures described hereinafter the following abbreviations were used: "ACN" stands for acetonitrile; "THF" stands for tetrahydrofuran; "DCM" stands for dichloromethane; "DIPE" stands for diisopropylether; "DMF" means N,N-dimethyl-formamide;. "NMP" means N-methyl-2-pyrrolidone; "TFA" means trifluoroacetic acid; "TIS" means triisopropylsilane; "DIPEA" means diisopropylethylamine; "TMSOTf" means trimethylsilyl triflate and "MIK" means methyl isobutyl ketone. Extrelut™ is a product of Merck KgaA, Darmstadt, Germany, and is a short column comprising diatomaceous earth.

A. PREPARATION OF INTERMEDIATE COMPOUNDS

EXAMPLE A.1

α-Bromo-methyl ester benzeneacetic acid (0.026 mole) was added dropwise to a mixture of 1-(4-nitrophenyl)piperazine (0.028 mole) and $Na_2CO_3$ (0.024 mole) in DMF (150 ml) while stirring. The mixture was stirred at room temperature for 66 hours, poured out into ice water (500 ml) and stirred for 30 minutes. The precipitate was filtered off and dissolved in DCM. The organic solution was dried, filtered and the solvent was evaporated. This fraction was purified over silica gel on a glass filter (eluent: $CH_2Cl_2$/$CH_3OH$ 99/1). The pure fractions were collected and the solvent was evaporated. Part of this fraction was stirred in ethanol. The precipitate was filtered off and dried, yielding 0.04 g of (±)-methyl 4-(4-nitrophenyl)-α-phenyl-1-piperazineacetate (intermediate 1, melting point 92° C.).

EXAMPLE A.2

A mixture of intermediate (1) (0.026 mole) and KOH (0.13 mole) in ethanol (150 ml) was stirred at room temperature for 18 hours, heated at 50° C. for 2.5 hours and cooled to room temperature. The precipitate was filtered off, stirred in 2-propanol, filtered off, washed three times with 2-propanol and dried. This fraction was stirred and refluxed in 2-propanol. HCl/2-propanol 6N (19.94 ml) was added. The mixture was stirred and refluxed, filtered warm and stirred in water (350 ml). The precipitate was filtered off and dried, yielding 5.94 g of (±)-4-(4-nitrophenyl)-α-phenyl-1-piperazineacetic acid monohydrate (intermediate 2).

EXAMPLE A.3

A mixture of intermediate (1) (0.0136 mole) and 1-(3-dimethylaminopropyl)-3-ethylcarbodiimide (0.02 mole) in DCM (125 ml) was stirred for two hours to give mixture (1). A mixture of 2,2,2-trifluoroethylamine (0.014 mole) in DCM (25 ml) was stirred. Triethylamine (1.5 g) was added and the mixture was stirred for 5 minutes to give mixture (2). Mixtures (1) and (2) were combined. The resulting mixture was stirred overnight and washed with water. The organic layer was separated, dried, filtered and the solvent was evaporated. The residue was purified by column chromatography over silica gel (eluent: $CH_2Cl_2$/$CH_3OH$ 98/2). The pure fractions were collected and the solvent was evaporated. This fraction was purified by column chromatography over silica gel (eluent: DCM/hexane/ethyl acetate 50/20/30). The pure fractions were collected and the solvent was evaporated, yielding 2.3 g (±)-4-(4-nitrophenyl)-α-phenyl-N-(2,2,2-trifluoroethyl)-1-piperazineacetamide (intermediate 3).

EXAMPLE A.4

A mixture of intermediate (3) (0.0054 mole) in methanol (150 ml) was hydrogenated with Pd/C 10% (1 g) as a catalyst in the presence of a 4% thiophene solution (1 ml). After uptake of hydrogen (2 equivalents), the catalyst was filtered off and the filtrate was evaporated. The residue was triturated in DIPE. The precipitate was filtered off and dried, yielding 1.5 g of (±)-4-(4-aminophenyl)-α-phenyl-N-(2,2,2-trifluoroethyl)-1-piperazineacetamide (intermediate 4, melting point 136° C.).

EXAMPLE A.5

A mixture of 4'-(trifluoromethyl)-[1,1'-biphenyl]-2-carbonyl chloride (0.185 mole) in DCM (1500 ml) and triethylamine (50 ml) was stirred on an ice-bath for 5 minutes. 4-[4-(Phenylmethyl)-1-piperazinyl]-benzenamine (0.37 mole) in DCM (500 ml) was added dropwise. The mixture was stirred for 3 hours. The organic layer was separated, washed with water, dried, filtered and the solvent was evaporated. The residue was triturated in DIPE. The precipitate was filtered off and dried, yielding 99.8 g of N-[4-[4-(phenylmethyl)-1-piperazinyl]phenyl]-4'-(trifluoro-methyl)-[1,1'-biphenyl]-2-carboxamide (intermediate 5, melting point 180° C.).

EXAMPLE A.6

A mixture of intermediate (5) (0.19 mole) in methanol (600 ml) and THF (600 ml) was hydrogenated overnight with Pd/C 10% (3 g) as a catalyst. After uptake of hydrogen (1 equivalent), the catalyst was filtered off and the filtrate was evaporated. The residue was triturated in DIPE. The precipitate was filtered off, dried, and dissolved in water. The mixture was alkalinized with $Na_2CO_3$ and then extracted with DCM. The organic layer was separated, dried, filtered and the solvent was evaporated. The residue was triturated in DIPE. The precipitate was filtered off and dried, yielding 40 g of N-[4-(1-piperazinyl)phenyl]-4'-(trifluoromethyl)-[1,1'-biphenyl]-2-carboxamide (intermediate 6).

EXAMPLE A.7

A mixture of 4'-(trifluoromethyl)-[1,1'-biphenyl]-2-carboxylic acid (0.09 mole) in DCM (500 ml) and DMF (5 ml) was stirred. Ethanedioyl dichloride (0.09 mole) was added dropwise. The mixture was stirred for 1 hour to give mixture (1). A mixture of 4-[1-(phenylmethyl)-4-piperidinyl]-benzenamine (0.046 mole) in DCM (500 ml) and triethylamine (20 ml) was stirred on an ice-bath. Mixture (1) was added dropwise. The mixture was stirred and refluxed overnight, then cooled and washed with water. The organic layer was separated, dried, filtered and the solvent was evaporated. The residue was purified by column chromatography over silica gel (eluent: $CH_2Cl_2/CH_3OH$ 98/2). The pure fractions were collected and the solvent was evaporated. The residue was triturated in DIPE. The precipitate was filtered off and dried, yielding 5.6 g of N-[4-[1-(phenylmethyl)-4-piperidinyl]phenyl]-4'-(trifluoromethyl)-[1,1'-biphenyl]-2-carboxamide (intermediate 7, melting point 134° C.).

EXAMPLE A.8

A mixture of intermediate (7) (0.025 mole) in methanol (250 ml) was hydrogenated at 50° C. overnight with Pd/C 10% (2 g) as a catalyst. After uptake of hydrogen (1 equivalent), the catalyst was filtered off and the filtrate was evaporated. The residue was triturated in DIPE. The precipitate was filtered off and dried. A part (0.2 g) of this fraction was purified by high performance liquid chromatography over RP-18 (eluent: ($NH_4OAc$ 0.5%/$CH_3CN$ 90/10)/$CH_3OH$/$CH_3CN$ 75/25/0, 0/50/50, 0/0/100 and 75/25/0; column: Hyperprep RP 100 Å 8 μm). The pure fractions were collected and the solvent was evaporated, yielding 0.119 g of N-[4-(4-piperidinyl)phenyl]-4'-(trifluoromethyl)-[1,1'-biphenyl]-2-carboxamide acetate (1:2) (intermediate 8, melting point 150° C.).

EXAMPLE A.9

A mixture of 4-[4-(phenylmethyl)-1-piperazinyl]-benzenamine (0.12 mole) in THF (300 ml) and triethylamine (50 ml) was stirred. [1,1'-Biphenyl]-2-carbonyl chloride (0.12 mole) was added dropwise. The mixture was stirred overnight. The solvent was evaporated. The residue was dissolved in DCM. The organic layer was separated, washed, dried, filtered and the solvent was evaporated. The residue was triturated in DIPE/2-propanol. The precipitate was filtered off and dried. A part (1 g) of this fraction was purified by column chromatography over silica gel (eluent: $CH_2Cl_2$/$CH_3OH$ 99/1). The pure fractions were collected and the solvent was evaporated. The residue was triturated in DIPE. The precipitate was filtered off and dried, yielding 0.84 g of N-[4-[4-(phenylmethyl)-1-piperazinyl]phenyl]-[1,1'-biphenyl]-2-carboxamide (intermediate 9, melting point 162° C.).

EXAMPLE A.10

A mixture of intermediate (9) (0.1 mole) in methanol (500 ml) was hydrogenated for two hours with palladium-on-carbon (10%) (10 g) as a catalyst. After uptake of hydrogen (1 equivalent), the catalyst was filtered off and the filtrate was evaporated. The residue was triturated in 2-propanol. The precipitate was filtered off and dried, yielding 29 g of N-[4-(1-piperazinyl)phenyl]-[1,1'-biphenyl]-2-carboxamide (intermediate 10, melting point 176° C.).

EXAMPLE A.11 a) A mixture of 4-(4-bromophenyl)-1-(phenylmethyl)-4-piperidinol (0.23 mole) and $Cu_2O$ (2 g) in aqueous ammonia (500 ml) was stirred at 180° C. for twelve hours. The mixture was cooled, extracted with DCM and washed with water. The organic layer was dried, filtered off and evaporated, yielding 60 g of 4-[1,2,3,6-tetrahydro-1-(phenylmethyl)-4-pyridinyl]benzenamine.

b) [1,1'-Biphenyl]-2-carbonyl chloride (0.05 mole) was added dropwise to a stirring mixture of 4-[1,2,3,6-tetrahydro-1-(phenylmethyl)-4-pyridinyl]benzenamine (0.045 mole) in THF (300 ml) and triethylamine (25 ml). The mixture was stirred overnight. The solvent was evaporated. The residue was dissolved in DCM. The organic layer was separated, washed, dried, filtered and the solvent was evaporated. The residue was triturated in DIPE. The precipitate was filtered off and dried, yielding 18.5 g of N-[4-[1,2,3,6-tetrahydro-1-(phenylmethyl)-4-pyridinyl]phenyl]-[1,1'-biphenyl]-2-carboxamide (intermediate 11, melting point 142° C.).

EXAMPLE A.12

A mixture of α-phenyl-4-piperidineacetonitrile hydrochloride (0.05 mole), 1-fluoro-4-nitrobenzene (0.06 mole) and potassium carbonate (0.15 mole) in DMF (200 ml) was stirred at 50° C. for four hours. Water and DIPE were added. The mixture was cooled. The precipitate was filtered off, washed with water and DIPE and dried, yielding 11.6 g of (±)-1-(4-nitrophenyl)-α-phenyl-4-piperidine-acetonitrile (intermediate 12, melting point 118° C.).

EXAMPLE A.13

A mixture of intermediate (12) (0.036 mole) in a 48% aqueous solution of hydrogen bromide (100 ml) was stirred and refluxed for three hours, cooled, poured out into water and extracted twice with DCM. The organic layer was separated, washed with water, dried, filtered and the solvent was evaporated. The residue was triturated with 2-propanol. The precipitate was filtered off and dried, yielding 9.5 g of (±)-1-(4-nitrophenyl)-α-phenyl-4-piperidineacetic acid (intermediate 13, melting point 216° C.).

EXAMPLE A.14

Thionyl chloride (0.01 mole) was added to a mixture of intermediate (13) (0.0029 mole) in DCM (10 ml). The mixture was stirred for one minute overnight and then allowed to stand. The solvent was evaporated. The residue was dissolved in DCM (10 ml). Methanol (10 ml) was added. The mixture was allowed to stand for four hours, then poured out into a $NaHCO_3$ solution and extracted with DCM. The organic layer was separated, dried, filtered and the solvent was evaporated. The residue was triturated in hexane/DIPE. The precipitate was filtered off and dried, yielding 0.9 g of (±)-methyl 1-(4-nitrophenyl)-α-phenyl-4-piperidineacetate (intermediate 14, melting point 124° C.).

EXAMPLE A.15

A mixture of intermediate (14) (0.0022 mole) in methanol (100 ml) was hydrogenated at 50° C. with palladium-on-carbon (10%) (0.1 g) as a catalyst in the presence of a 4% thiophene solution (0.1 ml). After uptake of hydrogen (3 equivalents), the catalyst was filtered off and the filtrate was evaporated. The residue was triturated in hexane. The precipitate was filtered off and dried, yielding 0.7 g of (±)-methyl 1-(4-aminophenyl)-α-phenyl-4-piperidineacetate (intermediate 15, melting point 125° C.).

EXAMPLES A.16 to A.18

In order to facilitate the understanding of these examples, the following presents a scheme (scheme 1) of the preparation of intermediate resins starting from a commercially available resin:

Scheme 1:
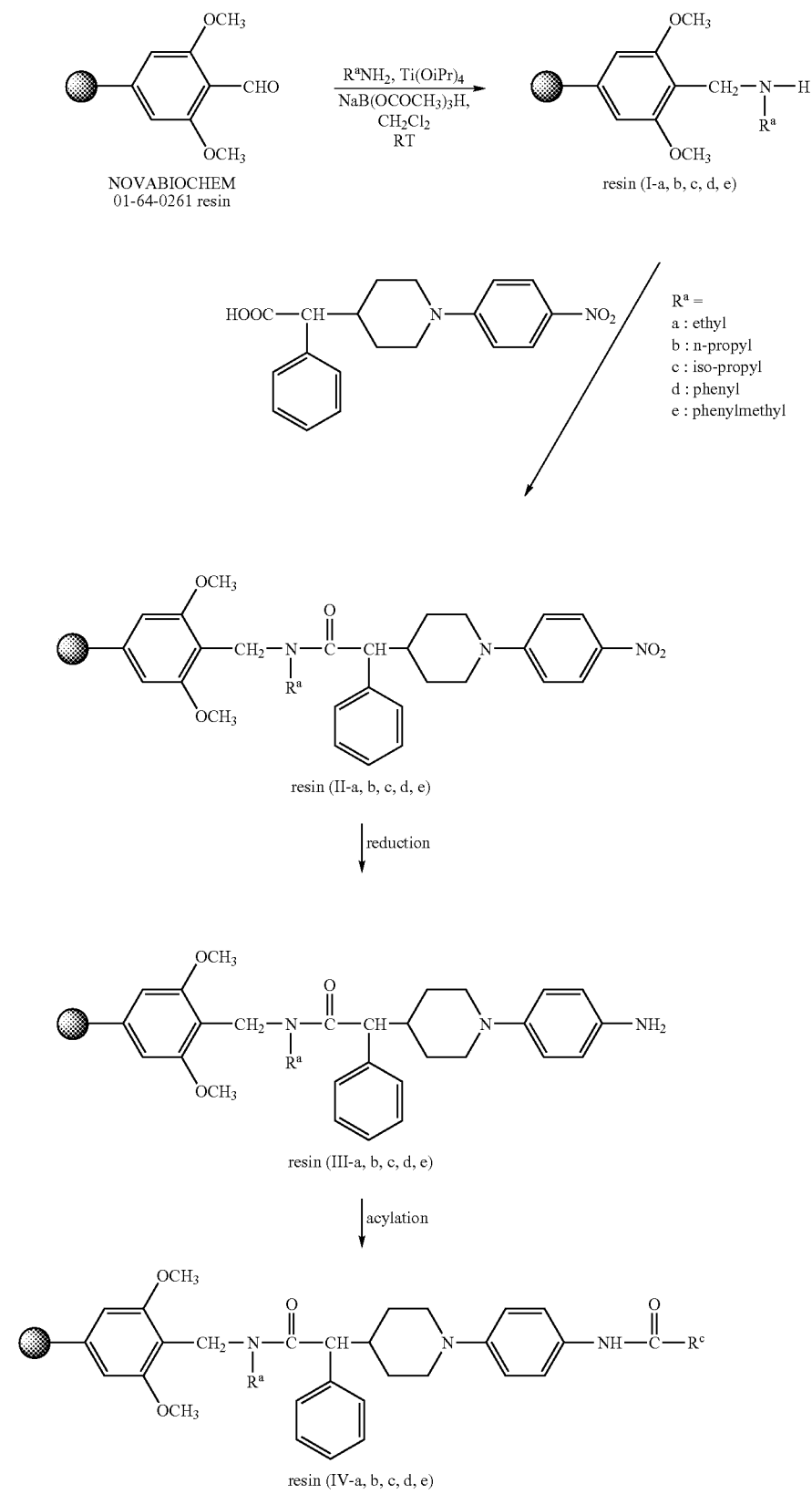

$R^c$ being ortho-iodophenyl, and $Z^a$ being hydroxy or chloro.

EXAMPLE A.16

Ethylamine (0.0056 mole; 2.8 ml of a 2 M solution in THF, thus $R^a$=a in scheme 1) was added to a Novabiochem 01-64-0261 commercial resin (1 g) in DCM (15 ml). Titanium (IV) isopropoxide (1.65 ml) was added and the mixture was shaken for one hour at room temperature. Triacetoxy borohydride (1.187 g) was added and the reaction mixture was shaken for 48 hours at room temperature. The mixture was filtered, and the filter residue was washed three times with DCM, three times with a (1:1) mixture of DCM and methanol, three times with firstly methanol, then secondly with DCM, once with a mixture of 10 ml DCM and 2 ml DIPEA, three times with firstly DCM, then secondly with methanol, then dried, quantitatively yielding an ethylamino terminated resin identified as I-a in scheme 1, which is used in the next reaction step without further purification.

EXAMPLE A.17

Intermediate (13) (0.0056 mole) was added to the resin of example A.16 (0.00112 mole). A solution of a complex of (T-4)-hexafluorophosphate($1^-$) (1-hydroxy-1H-benzotriazolato-O)tri-1-pyrrolidinyl-phosphorus($1^+$) (hereinafter referred to as "PyBOP") (2.9 g) in DCM (15 ml) and DMF (5 ml) was added. Triethylamine (0.0112 mole) was added and the reaction mixture was shaken for 24 hours at room temperature, filtered and the filter residue was washed with DMF (5×20 ml), then five times with (1:1) mixture of DCM and methanol (20 ml), five times with a (95:5) mixture of DCM with acetic acid (20 ml), five times with DMF (20 ml) and three times with NMP (20 ml), quantitatively yielding a nitro terminated resin identified as II-a in scheme 1.

EXAMPLE A.18

A mixture of the resin of example A.17 (0.00112 mole) and $SnCl_2.2H_2O$ (0.0224 mole) in NMP (20 ml) was shaken for six days at 55° C., then cooled, filtered and the filter residue was washed with DMF (three times), with a mixture of 10 ml DMF and 2 ml DIPEA, and then three times with firstly DCM, followed by secondly methanol, then dried, quantitatively yielding an amino terminated resin identified as III-a in scheme 1.

EXAMPLE A.19

Triisopropylamine (0.011 mole) was added to the resin of example A.18 (0.00112 mole) in DCM (10 ml). N,N-dimethyl-4-pyridinamine (0.0003 mole) in DCM (3 ml) was added. A solution of o-iodobenzoyl chloride (0.00336 mole) in DCM (5 ml) was added and the reaction mixture was shaken overnight at room temperature. The mixture was filtered, the residue was Washed three times with DCM, once with a mixture of DCM (10 ml) and DIPEA (2 ml), three times with DCM then methanol, then dried. The resulting product was treated with benzylamine (1 ml) in DCM (10 ml) and shaken for 60 hours at room temperature. The mixture was filtered, washed three times with DCM, once with DCM/methanol 50/50, three times with DCM then methanol, then dried, yielding 0.00515 g (46%) of a resin identified as IV-a in scheme 1.

EXAMPLE A.20

The procedure of example A.16 is repeated while replacing ethylamine by n-propylamine, thus quantitatively yielding a n-propylamino terminated resin identified as I-b in scheme 1.

EXAMPLE A.21

The first experimental procedure of example A.17 is repeated while replacing the resin of example A.16 by the resin of example A.20, thus quantitatively yielding the resin identified as II-b in scheme 1.

EXAMPLE A.22

The procedure of example A.18 is repeated while replacing the resin of example A.17 by the resin of example A.21, thus quantitatively yielding the resin identified as III-b in scheme 1.

EXAMPLE A.23

The procedure of example A.19 is repeated while replacing the resin of example A.18 by the resin of example A.22, thus yielding the resin identified as IV-b in scheme 1.

EXAMPLE A.24

The procedure of example A.16 is repeated while replacing ethylamine by isopropylamine, thus quantitatively yielding an isopropylamino terminated resin identified as I-c in scheme 1.

EXAMPLE A.25

The first experimental procedure of example A.17 is repeated while replacing the resin of example A.16 by the resin of example A.24, thus quantitatively yielding the resin identified as II-c in scheme 1.

EXAMPLE A.26

The procedure of example A.18 is repeated while replacing the resin of example A.17 by the resin of example A.25, thus quantitatively yielding the resin identified as III-c in scheme 1.

EXAMPLE A.27

The procedure of example A.19 is repeated while replacing the resin of example A.18 by the resin of example A.26, thus yielding the resin identified as IV-c in scheme 1.

EXAMPLE A.28

The procedure of example A.16 is repeated while replacing ethylamine by phenylamine, thus quantitatively yielding a phenylamino terminated resin identified as I-d in scheme 1.

EXAMPLE A.29

The first experimental procedure of example A.17 is repeated while replacing the resin of example A.16 by the resin of example A.28, thus quantitatively yielding the resin identified as II-d in scheme 1.

EXAMPLE A.30

The procedure of example A.18 is repeated while replacing the resin of example A.17 by the resin of example A.29, thus quantitatively yielding the resin identified as III-d in scheme 1.

EXAMPLE A.31

The procedure of example A.19 is repeated while replacing the resin of example A.18 by the resin of example A.30, thus yielding the resin identified as IV-d in scheme 1.

EXAMPLE A.32

The procedure of example A.16 is repeated while replacing ethylamine by benzylamine, thus quantitatively yielding a benzylamino terminated resin identified as I-e in scheme 1.

EXAMPLE A.33

The first experimental procedure of example A.17 is repeated while replacing the resin of example A.16 by the resin of example A.32, thus quantitatively yielding the resin identified as II-e in scheme 1.

EXAMPLE A.34

The procedure of example A.18 is repeated while replacing the resin of example A.17 by the resin of example A.33, thus quantitatively yielding the resin identified as III-e in scheme 1.

EXAMPLE A.35

The procedure of example A.19 is repeated while replacing the resin of example A.18 by the resin of example A.34, thus yielding the resin identified as IV-e in scheme 1.

EXAMPLES A.36 to A.38

In order to facilitate the understanding of these examples, the following presents another scheme (scheme 2) for the preparation of intermediate resins starting from a commercially available resin:

Scheme 2:

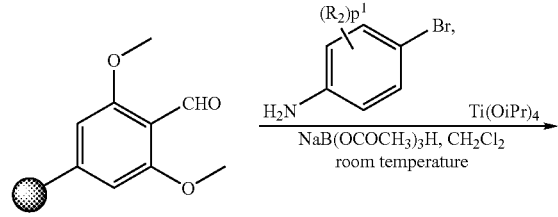

NOVABIOCHEM
01-64-0261

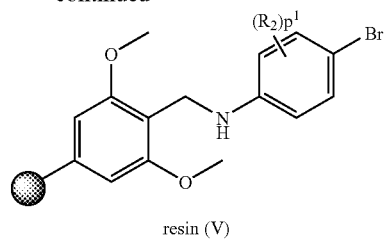

resin (V)

resin (V) →
DIPEA, DMAP, CH$_2$Cl$_2$
room temperature $R^b$ = hydrogen or CF$_3$

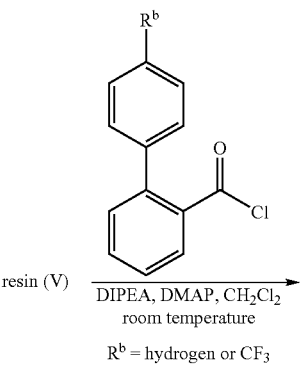

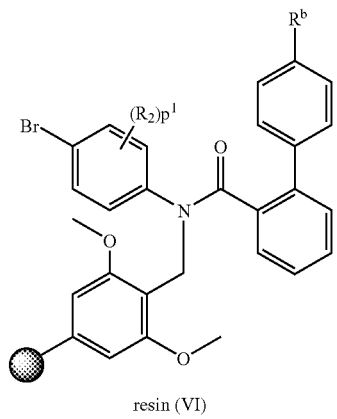

resin (VI)

resin (VI-a) : $R^b$ = H; $R_2$ = H
resin (VI-b) : $R^b$ = CF$_3$; $R_2$ = H
other resins of formula (VI) are possible
wherein $p_1$ = 1 and R = CH$_3$, F, Cl, OCH$_3$, CF$_3$

EXAMPLE A.36

A mixture of commercial Novabiochem 01-64-0261 resin (25.1 g, 0.028 mole), 4-bromoaniline (24 g, 0.140 mole) and titanium (IV) isopropoxide (41 ml, 0.140 mole) in DCM (400 ml) was stirred gently for one hour at room temperature. Sodium triacetoxyborohydride (30 g, 0.140 mole) was added and the reaction mixture was stirred overnight at room temperature. Methanol (50 ml) was added and the mixture was stirred for one hour, then filtered, washed once with DCM, once with methanol, then once with DCM (200 ml)+DIPEA (20 ml), washed three times with firstly DCM, followed secondly by methanol, then dried, yielding 29.28 g of a resin identified as V in scheme 2, which is used in the next reaction step without further purification.

EXAMPLE A.37

4-Phenyl benzoic acid (8.3 g, 0.042 mole) was dissolved in DCM (100 ml). Thionyl chloride (10 g, 0.084 mole) was added. DMF (10 drops) was added and the mixture was stirred and refluxed for one hour. The solvent was evaporated. DCM (three times 50 ml) was added. The solvent was evaporated. The residue was dissolved in DCM (50 ml). This solution was added to a mixture of the resin of example A.36 (14.64 g, 0.0133 mole), DIPEA (24 ml, 0.140 mole) and 4-dimethylaminopyridine (hereinafter referred as DMAP) (0.5 g) in DCM (150 ml). The reaction mixture was shaken overnight at room temperature, then filtered and the filter residue was washed with 100 ml DMF+20 ml DIPEA, then with methanol, water, DCM, methanol, DCM and methanol, and dried, yielding 15.73 g of a resin identified as VI-a in scheme 2.

EXAMPLE A.38

4'-(Trifluoromethyl)-2-biphenyl carboxylic acid (14.64 g, 0.042 mole) was dissolved in DCM (100 ml). DMF (1 ml) was added. Thionyl chloride (10 g, 0.084 mole) was added and the mixture was stirred and refluxed for one hour. The solvent was evaporated. DCM (twice 50 ml) was added, then the solvent was evaporated. The residue was dissolved in DCM (50 ml). This solution was added to a mixture of the resin of example A.36 (14.64 g, 0.0133 mole), DIPEA (24 ml, 0.140 mole) and DMAP (0.5 g) in DCM (150 ml). The reaction mixture was shaken for four hours at room temperature then filtered and the filter residue was washed with 100 ml DMF+20 ml DIPEA, then washed three times firstly with DCM and secondly with methanol, and finally dried. This reaction product was reacted once more with half the initial quantities of 4'-(trifluoromethyl)-2-biphenyl carboxylic acid, thionyl chloride, DIPEA and DMAP. The reaction mixture was shaken overnight at room temperature, then filtered, and the filter residue was shaken with DMF+20 ml DIPEA, then methanol, water, methanol, DCM, methanol, DCM and methanol, then dried, yielding 17.48 g of a resin identified as VI-b in scheme 2.

EXAMPLE A.39 a) A mixture of 4'-(trifluoromethyl)-[1,1'-biphenyl]-2-carboxylic acid (0.09 mol) in DCM (500 ml) and DMF (5 ml) was stirred. Ethanedioyl dichloride (0.09 mol) was added dropwise. The mixture was stirred for 1 hour to give mixture 1. A mixture of 4-[1-(phenylmethyl)-4-piperidinyl]-benzenamine hydrochloride salt (1:1) (0.046 mol) in DCM (500 ml) and triethylamine (20 ml) was stirred on an ice-bath. Mixture 1 was added dropwise. The mixture was stirred and refluxed overnight, then cooled and washed with water. The organic layer was separated, dried, filtered and the solvent was evaporated. The residue was purified by column chromatography over silica gel (eluent: CH$_2$Cl$_2$/CH$_3$OH 98/2). The pure fractions were collected and the solvent was evaporated. The residue was triturated in DIPE. The precipitate was filtered off and dried, yielding 5.6 g of N-[4-[1-(phenylmethyl)-4-piperidinyl]phenyl]-4'-(trifluoromethyl)-[1,1'-biphenyl]-2-carboxamide (intermediate 16, mp. 134° C.).

b) A mixture of intermediate (16) (0.025 mol) in methanol (250 ml) was hydrogenated at 50° C. overnight with Pd/C 10% (2 g) as a catalyst. After uptake of hydrogen (1 equivalent), the catalyst was filtered off and the filtrate was evaporated. The residue was triturated in DIPE. The precipitate was filtered off and dried, yielding 7.7 g N-[4-(4-piperidinyl)phenyl]-4'-(trifluoromethyl)-[1,1'-biphenyl]-2-carboxamide (intermediate 17).

EXAMPLE A.40 a) [1,1'-Biphenyl]-2-carboxylic acid (0.25 mol) was dissolved in DCM (500 ml) and DMF (0.5 ml). Thionyl chloride (0.51 mol) was added dropwise The mixture was stirred and refluxed for 1 hour under nitrogen flow. The solvent was evaporated. DCM (500 ml) was added twice. The solvent was evaporated twice. The residue was dissolved in DCM (200 ml) and then added dropwise at 0° C. to a mixture of 4-[1-(phenylmethyl)-4-piperidinyl]-benzenamine (0.25 mol) and N-(1-methylethyl)-2-propanamine (0.75 mol) in DCM (800 ml). The mixture was brought to room temperature and then stirred at room temperature overnight under nitrogen flow. The mixture was washed three times with water (800 ml). The organic layer was separated, dried, filtered and the solvent was evaporated, yielding 125 g of N-[4-[1-(phenylmethyl)-4-piperidinyl]phenyl]-[1,1'-biphenyl]-2-carboxamide (intermediate 18).

b) A mixture of intermediate (18) (0.145 mol) in methanol (500 ml) was hydrogenated at 50° C. during 48 hours with Pd/C (10%, 3 g) as a catalyst. After uptake of hydrogen (1 equivalent), the catalyst was filtered off and the filtrate was evaporated. The residue was triturated in DIPE. The precipitate was filtered off and dried, yielding 49 g of N-[4-(4-piperidinyl)phenyl]-[1,1'-biphenyl]-2-carboxamide (intermediate 19).

EXAMPLE A.41 a) 4'-(Trifluoromethyl)-[1,1'-biphenyl]-2-carbonyl chloride (0.12 mol) was added dropwise to a stirring mixture of 4-[1,2,3,6-tetrahydro-1-(phenylmethyl)-4-pyridinyl]benzenamine (0.095 mol) in DCM (300 ml) and triethylamine (50 ml). The mixture was stirred overnight, poured out into water and then stirred for 30 minutes. The organic layer Was separated, washed, dried, filtered and the solvent was evaporated. The residue was triturated in DIPE. The precipitate was filtered off and dried, yielding 43 g of N-[4-[1,2,3,6-tetrahydro-1-(phenylmethyl)-4-pyridinyl]phenyl]-4'-(trifluoromethyl)-[1,1'-biphenyl]-2-carboxamide (intermediate 20).

b) 1-Chloroethyl chloroformate (0.078 mol) was added dropwise to a stirring mixture of intermediate (20) (0.039 mol) in 1,2-dichloro-ethane (500 ml). The mixture was stirred for 30 minutes and then stirred and refluxed overnight. The solvent was evaporated. Methanol (500 ml) was added. The mixture was stirred and refluxed overnight. The solvent was evaporated. The residue was triturated in DIPE. The precipitate was filtered off and dried, yielding 20.8 g of N-[4-(1,2,3,6-tetrahydro-4-pyridinyl)phenyl]-4'-(trifluoromethyl )-[1,1'-biphenyl]-2-carboxamide (intermediate 21).

EXAMPLE A.42

A mixture of intermediate (11) (0.04 mol) in 1,2-dichloro-ethane (200 ml) was stirred on an ice-bath. 1-Chloroethyl chloroformate (15 ml) was added dropwise at a temperature below 5° C. The mixture was stirred for 1 hour and then stirred and refluxed overnight. The solvent was evaporated. Methanol (200 ml) was added. The mixture was stirred and refluxed for 2 hours. The solvent was evaporated. The residue was triturated in DIPE. The precipitate was filtered off and dried, yield 16.7 g of N-[4-(1,2,3,6-tetrahydfo-4-pyridinyl)phenyl]-[1,1'-biphenyl]-2-carboxamide (intermediate 22).

EXAMPLE A.43 a) A mixture of intermediate (6) (0.0047 mol) and di-tert-butyl dicarbonate (0.0052 mol) in DCM (50ml) was stirred at room temperature for 2 hours. DMF (5 ml) was added. The mixture was stirred at room temperature for 3 hours. The solvent was evaporated. The residue was stirred in DIPE. The precipitate was filtered off and dried in vacuo at 54° C., yielding 2.47 g of 1,1-dimethylethyl ester 4-[4-[[[4'-(trifluoromethyl)[1,1'-biphenyl]-2-yl]carbonyl]amino]phenyl]-1-piperazinecarboxylic acid (intermediate 23, mp. 204° C.).

b) NaH 60% in mineral oil (0.0056 mol) was treated with hexane; stirred under nitrogen flow and decanted. DMF dry (25 ml) was added to the residue. The suspension was stirred at room temperature under nitrogen flow. A solution of intermediate (23) (0.00375 mol) in DMF dry (25 ml) was added dropwise. The mixture was stirred at room temperature under nitrogen flow for 2.5 hours. A solution of methyl methanesulfonate (0.0045 mol) in DMF dry (50 ml) was added dropwise. The mixture was stirred at room temperature for 18 hours. Water (150 ml) was added. The mixture was extracted twice with DCM. The organic layer was separated, dried, filtered and the solvent was evaporated. The residue was stirred in 60 ml of hexane/DIPE (3:1). The mixture was stirred and refluxed until a clear solution was obtained and then brought to room temperature. The precipitate was filtered off and dried, yielding 1.6 g of 1,1-dimethylethyl ester 4-[4-[methyl[[4'-(trifluoromethyl)[1,1'-biphenyl]-2-yl]carbonyl]amino]phenyl]-1-piperazinecarboxylic acid (intermediate 24).

c) A solution of trifluoroacetate (20 ml) and DCM (200 ml) was added to intermediate (24) (0.0024 mol) and stirred for 1 hour and 30 minutes at room temperature. The solvent was evaporated. DCM was added and again the solvent was evaporated, yielding 1.7 g of N-methyl-N-[4-(1-piperazinyl)phenyl]-4'-(trifluoromethyl)-[1,1'-biphenyl]-2-carboxamide (intermediate 25).

EXAMPLE A.44

Intermediate resins wherein $X_2$ and $X_3$ represent N and $Z_1$ and $Z_2$ represent —$CH_2CH_2$— can be prepared as depicted in scheme 3 starting from a commercially available resin:

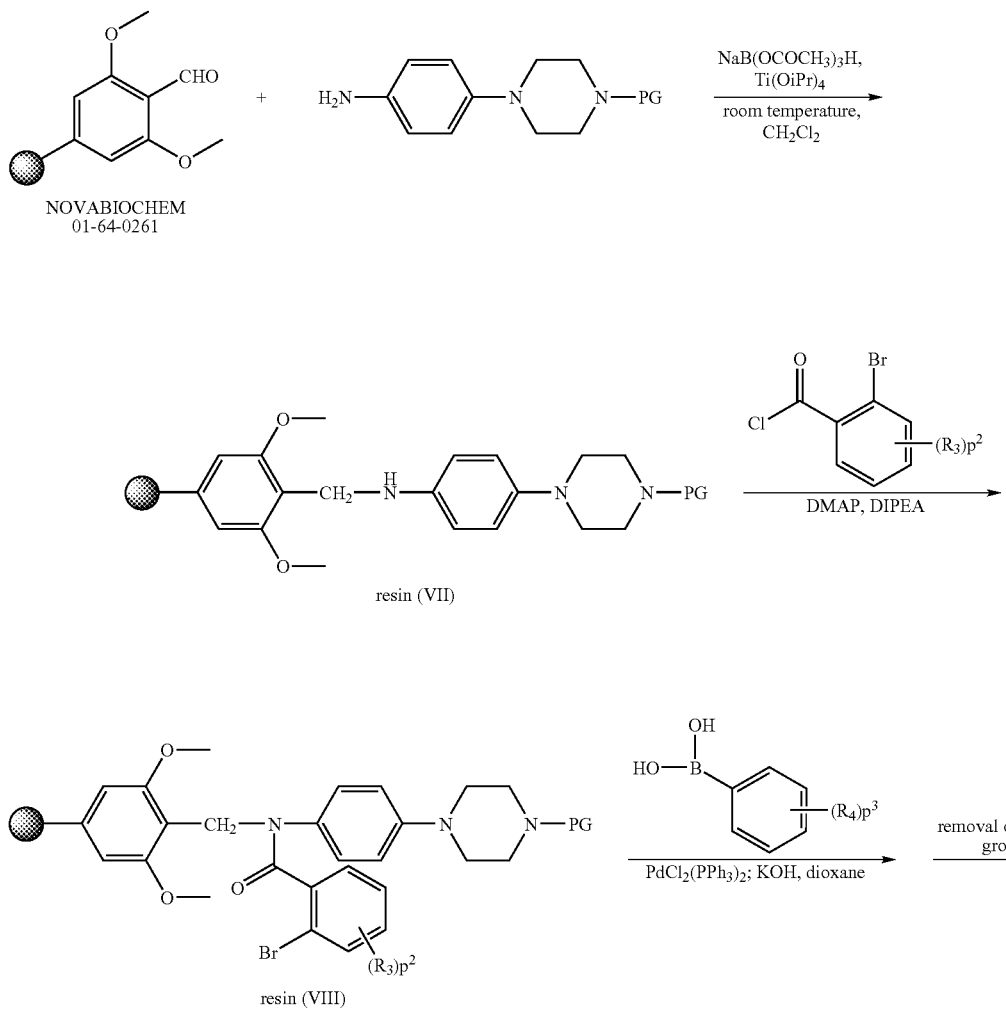

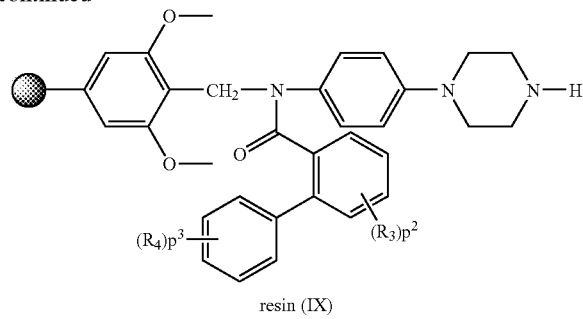

resin (IX)

a) A mixture of commercial Novabiochem 01-64-0261 resin (0.180 g, 0.002 mol), 4-(1-tert-butoxycarbonylpiperazin-4-yl)aniline ((0.001 mol), dissolved in DCM (2 ml)) and titanium (IV) isopropoxide (0.001 mol) in DCM (3 ml) was shaken for 2 hours at room temperature. Sodium triacetoxyborohydride (0.001 mol) was added portionwise and the reaction mixture was shaken for 20 hours at room temperature. The mixture was filtered and the filter residue was washed three times with DCM (3 times), methanol (3 times), and then three times with DCM, then dried, yielding resin (VII-a).

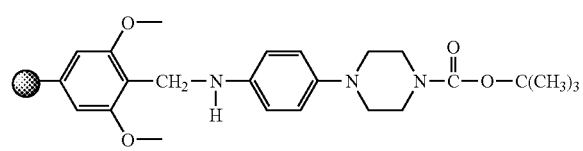

resin (VII-a)

b) 2-Bromo-4-methylbenzoic acid (0.001 mol) in DCM (5 ml) with thionyl chloride (0.013 mol) was stirred and refluxed for one hour. The mixture was blown dry under nitrogen. Again, DCM (5 ml) with thionyl chloride (0.013 mol) was added. The reaction mixture was stirred and refluxed for one hour. The mixture was blown dry under nitrogen and three times with DCM (3 ml) was added, then evaporated again. The residue was dissolved in DCM (3 ml). this solution was added to a solution of resin (VII-a) (0.0002 mol) in DCM (1 ml). DMAP (0.0002 mol) in DCM (1 ml) was added. DIPEA (0.002 mol) was added and the reaction mixture was shaken for 20 hours at room temperature. The reaction mixture was filtered and the filter residue was washed three times with DCM (3 times), methanol (3 times), and then three times with DCM, then dried, yielding resin (VIII-a).

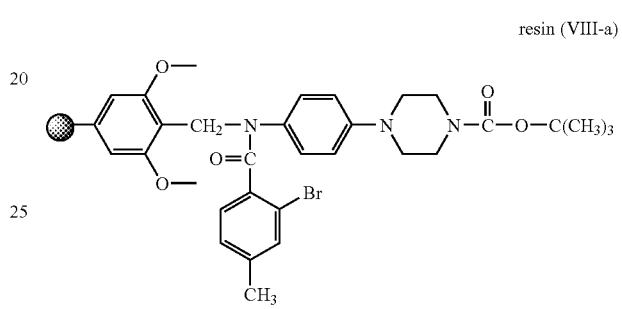

resin (VIII-a)

c) A solution of 4-(trifluoromethyl)benzeneboronic acid (0.0016 mol) in dioxane. (3 ml) was added to resin (VIII-a) (0.0002 mol) which was previously washed with dioxane (5 ml). Then, KOH (0.0032 mol of a 2 M solution) was added and the reaction mixture was shaken for 30 minutes at room temperature under a nitrogen atmosphere. $PdCl_2(PPh_3)_2$ (0.00004 mol) in NMP (0.5 ml) was added and the reaction mixture was shaken for 2 hours at 90° C. Again, $PdCl_2(PPh_3)_2$ (0.00004 mol) in NMP (0.5 ml) was added and the reaction mixture was shaken for 2 hours at 90° C. The mixture was cooled, filtered and the filter residue was washed with DMF (3 times), with water (3 times), DMF (3 times), methanol (3 times), DCM (3 times), methanol (3 times) and DCM (3 times), then dried yielding a residue. Said residue was stirred in a solution of TMSTf (1 M) and 2,6-lutidine (1.5 M) in DCM (4 ml) for 2 hours at room temperature, filtered, and washed with DCM (3 times) and methanol (3 times), and dried, yielding resin (IX-a).

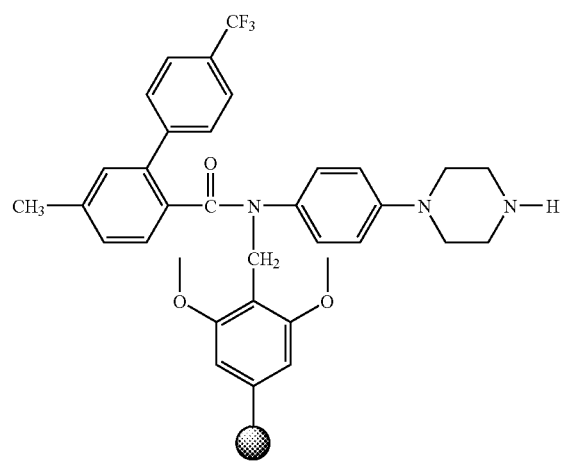

resin (IX-a)

EXAMPLE A.45

A suspension of 4-(tert-butoxycarbonylamino)piperidine (15 equivalents) in NMP (2 ml) was added to resin (VI-b) in NMP (1 ml). [1,1'-Binaphthalene]-2,2'-diylbis[diphenyl-phosphine (BINAP) (0.00011 mol) was added portionwise. tert-Butoxysodium (15 equivalents) was added portionwise. The reaction mixture was shaken for one hour under nitrogen flow. $Pd_2(dba)_3$ (0.000022 mol) in NMP (1 ml) was added and the reaction mixture was shaken for 18 hours at 105° C. The mixture was cooled, filtered and the filter residue was washed with three times (with DMF followed with water), and then three times with methanol, then DCM, yielding resin (X).

resin (X)

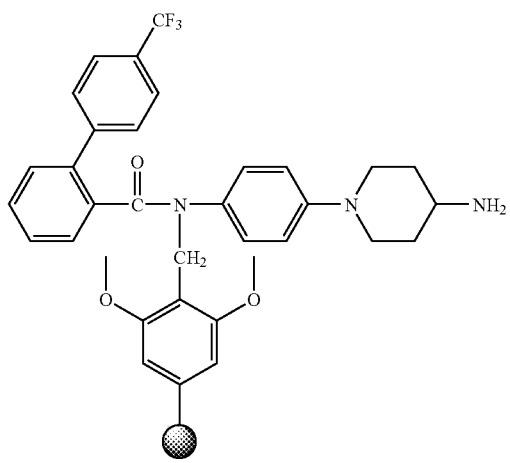

b) Resin (X) (0.00011 mol) was shaken in NMP (2 ml). Bromobenzene (0.00165 mol) in NMP (1 ml) was added. BINAP (0.068 g) was added portionwise. Tert-butoxysodium (0.190 g) was added portionwise. The mixture was shaken for 1 hour under nitrogen. $Pd_2(dba)_3$ (0.020 g) in NMP (1 ml) was added and the reaction mixture was shaken for 18 hours at 105° C., then cooled, filtered and the filter residue was washed with three times (with DMF followed with water), and then three times with methanol, then DCM yielding resin (XI).

resin (XI)

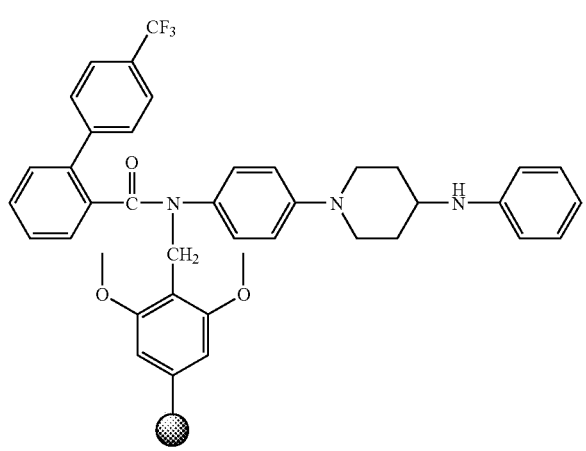

EXAMPLE A.45

Resin (XI) (0.0002 mol) was washed with DCM (4 ml), then filtered off, then dissolved in DCM (5 ml). Trichloromethyl chloroformate (0.001 mol) was added and the reaction mixture was shaken for 4 hours at room temperature. The mixture was filtered, washed three times with DCM, then dried, yielding resin (XII).

resin (XII)

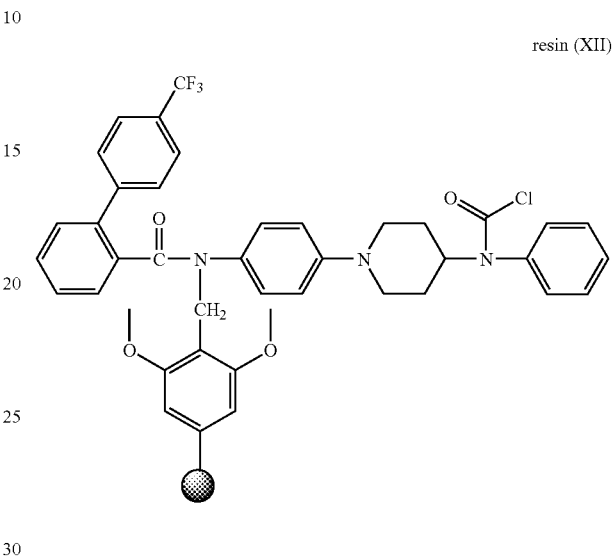

EXAMPLE A.46 a) 1-Ethyl-3-(3'-dimethylaminopropyl)carbodiimide hydrochloride (EDCI) (0.096 mol) was added at room temperature to a mixture of 4-(4-aminophenyl)-1-piperazinecarboxylic acid ethyl ester (0.08 mol), 2-iodo benzoic acid (0.096 mol) and,1-hydroxybenzotriazole (HOBT) (0.096 mol) in DCM (500 ml). The mixture was stirred at room temperature overnight. Water was added. The mixture was extracted with DCM. The organic layer was separated, dried, filtered, and the solvent was evaporated. The residue was taken up in DIPE. The precipitate was filtered off and dried, yielding 39 g of 4-[4-[(2-iodobenzoyl)-amino]phenyl]-1-piperazinecarboxylic acid, ethyl ester (intermediate 27).

b) A mixture of intermediate (27) (0.041 mol) and potassium hydroxide (0.41 mol) in ispropanol (200 ml) was stirred and refluxed for 3 hours and the solvent was evaporated till dryness. Water was added. The mixture was extracted with DCM and the solvent was evaporated, yielding 2-iodo-N-[4-(1-piperazinyl)phenyl]benzamide (intermediate 28).

c) α-Bromo-benzeneacetic acid methyl ester (0.0123 mol) was added at room temperature to a mixture of intermediate (28) (0.0123 mol) and $Na_2CO_3$ (0.0123 mol) in DMF (50 ml). The mixture was stirred at room temperature for 2 hours. Water was added. The mixture was stirred at room temperature for 15 minutes. The precipitate was filtered, washed with diethyl ether and dried, yielding 5.8 g of 4-[4-[(2-iodobenzoyl)amino]phenyl]-α-phenyl-1-piperazine-acetic acid, methyl ester (intermediate 29).

d) A mixture of intermediate (29) (0.0036 mol), tributyl-2-furanyl-stannane (0.029 mol), $PdCl_2(PPh_3)_2$ (0.0007 mol) and Na2CO3 (0.0576 mol) in dioxane (30 ml) was stirred and refluxed for 1 hour. Water was addedd. The mixture was extracted with ethyl acetate. The organic layer was separated, dried, filtered, and the solvent was evaporated. The residue was purified by column chromatography over silica gel (eluent:cyclohexane/ethyl acetate 80/20). The pure fractions were collected and the solvent was evaporated, yielding 4-[4-[[2-(2-furanyl)benzoyl]amino]phenyl]-α-phenyl-1-piperazineacetic acid, methyl ester (intermediate 30, mp. 90° C.).

e) A mixture of intermediate (30) (0.0006 mol) and potassium hydroxide (0.006 mol) in isopropanol (5 ml) was stirred at room temperature overnight. The solvent was evaporated. The residue was dissolved in isopropanol/HCl 6N and converted into the hydrochloric acid salt. The precipitate was filtered off and dried, yielding 0.31 g of 4-[4-[[2-(2-furanyl)benzoyl]amino]phenyl]-α-phenyl-1-piperazineacetic acid (intermediate 31).

B. PREPARATION OF POLYARYLCARBOXAMIDE COMPOUNDS OF THE INVENTION

EXAMPLE B.1

A mixture of 4'-(trifluoromethyl)-[1,1'-biphenyl]-2-carboxylic acid (0.012 mole) in DCM (100 ml) and DMF (8 drops) was stirred. Ethanedioyl dichloride (0.012 mole) was added. The mixture was stirred for 2 hours, to give mixture (I). Triethylamine (8 ml) was added to a mixture of intermediate (4) (0.005 mole) in DCM (100 ml). The mixture was stirred on an ice-salt bath to give mixture (II). Mixture (I) was added dropwise to mixture (II) and the resulting reaction mixture was'stirred and refluxed for two days. The solvent was evaporated. The residue was dissolved in DCM. The organic layer was separated, washed, dried, filtered and the solvent was evaporated. The residue was purified by column chromatography over silica gel (eluent: DCM/CH$_3$OH 99/1). The desired fractions were collected and the solvent was evaporated. The residue was triturated in DIPE. The precipitate was filtered off and dried, yielding 2.99 g of N-[4-[4-[2-oxo-1-phenyl-2-[(2,2,2-trifluoroethyl)amino]ethyl]-1-piperazinyl]-phenyl]-4'-(trifluoromethyl)-[1,1'-biphenyl]-2-carboxamide (melting point 208° C.) iden-tified as compound No. 1 in the following table F-1.

EXAMPLE B.2

Fluorene-4-carboxylic acid (0.00032 mole) in 1 ml of 1/1-mixture of DCM/NMP was added to PyBOP (0.00064 mole) in DCM (1 ml). This mixture was stood for 30 minutes, then added to the resin of example A.34. DCM (5 ml) was added, followed by DIPEA (0.00085 mole). The reaction mixture was shaken for 24 hours at room temperature, then filtered, washed 3 times with DCM, 3 times with methanol, followed by DCM. A mixture of TFA/DCM/TIS (5/93/2) (4 ml) was added and the mixture was shaken for one hour at room temperature. The mixture was filtered, the filter residue was washed with a mixture of TFA/DCM/TIS (5/93/2) (2 ml) and with DCM (2 ml). The filtrate was blown dry at 50° C. under a gentle stream of nitrogen gas, dissolved in DCM (5 ml) and DMF (1 ml) and a Novabiochem 01-64-0171 resin was added while stirring the mixture at room temperature. Then, after one hour, an Argonaut P/N 800277 resin (0.040 g) was added. The mixture was stirred for four hours at room temperature, filtered, and the filtrate was blown dry at 50° C. under a nitrogen flow, yielding 0.027 g of the compound identified as No. 2 in the following table F-1.

Compounds identified as No. 3 to No. 11 in the following table F-1 were similarly prepared while using the same experimental procedure and replacing fluorene-4-carboxylic acid by the appropriate reactive acid.

EXAMPLE B.3

Fluorene-4-carboxylic acid (0.00028 mole) in 1 ml of a 1/1 mixture of DCM/NMP was added to PyBOP (0.00028 mole) in DCM (1 ml). This mixture was stood for 30 minutes, then added to the resin of example A.22. DCM (5 ml) was added, followed by triethylamine (0.00057 mole). The reaction mixture was shaken for 20 hours at room temperature, then filtered, washed three times with DCM, three times with first methanol, followed by secondly DCM. 4 ml of a mixture of TFA/DCM/TIS (5/93/2) was added and the mixture was shaken for one hour at room temperature. The mixture was filtered, the filter residue was washed with a mixture of TFA/DCM/TIS (2 ml; 5/93/2) and with DCM (1 ml). The filtrate was blown dry at 50° C. under a gentle stream of nitrogen. This fraction was purified by high performance liquid chromatography over Hyperprep RP-C18 BDS (100 g, 100 Å, 8 μm; eluent: [(0.5% NH$_4$OAc in H$_2$O)/CH$_3$CN 90/10)]/CH$_3$OH/CH$_3$CN (0 minutes) 75/25/0, (10 minutes) /0/50/50, (16 minutes) 0/0/100, (18.10–20.00 minutes) 75/25/0). The pure fractions were collected and the organic solvent was evaporated. The aqueous concentrate was extracted with DCM/aqueous K$_2$CO$_3$ solution, then separated over Extrelut™. The organic phase was blown dry under nitrogen at 50° C. The residue was dried further under vacuum at 60° C., yielding 0.002 g of the compound identified as No.12 in the following table F-1.

Compounds identified as No.13 to No. 20 in the following table F-1 were similarly prepared while using the same experimental procedure and replacing fluorene-4-carboxylic acid by the appropriate reactive acid.

EXAMPLE B.4

Fluorene-4-carboxylic acid (0.00015 mole) in 1 ml of 1/1 mixture of DCM/NMP was added to PyBOP (0.0003 mole) in DCM (1 ml). This mixture was stood for 30 minutes, then added to the resin of example A.26. DCM (5 ml) was added, followed by DIPEA (0.00057 mole). The reaction mixture was shaken for 24 hours at room temperature, then filtered, washed three times with DCM, three times with first methanol, followed by secondly DCM. 4 ml of a mixture of TFA/DCM/TIS (5/93/2) was added and the mixture was shaken for one hour at room temperature. The mixture was filtered, the filter residue was washed with 2 ml of a mixture of TFA/DCM/TIS (5/93/2) and with DCM (1 ml). The filtrate was blown dry at 50° C. under a gentle stream of nitrogen. This fraction was purified by high performance liquid chromatography over Hyperprep C18 BDS (100 g, 100 Å, 8 μm; eluent: [(0.5% NH$_4$OAc in H$_2$O)/CH$_3$CN 90/10)]/CH$_3$OH/CH$_3$CN (0 minute) 75/25/0, (10 minute) 0/50/50, (16 minute) 0/0/100, (18.10–20.00 minute) 75/25/0). The pure fractions were collected and the organic solvent was evaporated. The aqueous concentrate was extracted with DCM/aqueous potassium carbonate solution, then separated over Extrelut™. The organic phase was blown dry under nitrogen at 50° C. The residue was dried further under vacuum at 60° C., yielding 0.002 g of the compound identified as No. 21 in the following table F-1.

Compounds identified as No. 22 to No. 28 in the following table F-1 were similarly prepared while using the same experimental procedure and replacing fluorene-4-carboxylic acid by the appropriate reactive acid.

EXAMPLE B.5

Fluorene-4-carboxylic acid (0.00023 mole) in 1 ml of 1/1 mixture of DCM/NMP was added to PyBOP (0.00046 mole) in DCM (1 ml). This mixture was stood for 30 minutes, then added to the resin of example A.30. DCM (5 ml) was added, followed by DIPEA (0.00057 mole). The reaction mixture was shaken for 24 hours at room temperature, then filtered, washed three times with DCM, three times with first methanol, followed by secondly DCM. A mixture of TFA/DCM/TIS (4 ml; 75/23/2) was added and the mixture was shaken for one hour at room temperature. The mixture was filtered, the filter residue was washed with 2 ml of a mixture of TFA/DCM/TIS (75/23/2) and with DCM (2 ml). The filtrate was blown dry at 50° C. under a gentle stream of nitrogen. The residue was dissolved in DCM (5 ml), then blown dry once more. This fraction was purified by high performance liquid chromatography over Hyperprep RP-C18 BDS (100 g, 100 Å, 8 μm; eluent: [(0.5% $NH_4OAc$ in $H_2O$)/$CH_3CN$ 90/10)]/$CH_3OH$/$CH_3CN$ (0 minute) 75/25/0, (10 minutes) 0/50/50, (16 minutes) 0/0/100, (18.10–20.00 minutes) 75/25/0). The pure fractions were collected and the organic solvent was evaporated. The aqueous concentrate was extracted with DCM/aqueous potassium carbonate solution, then separated over Extrelut™. The organic phase was blown dry under nitrogen at 50° C. The residue was dried further under vacuum at 60° C., yielding 0.0046 g of the compound identified as No. 29 in the following table F-1.

Compounds identified as No. 30 to No. 36 in the following table F-1 were similarly prepared while using the same experimental procedure and replacing fluorene-4-carboxylic acid by the appropriate reactive acid.

EXAMPLE B.6

A mixture of the Novabiochem 01-64-0261 commercial resin (0.00011 mole), intermediate (15) (0.00061 mole) and isopropyl titanate (0.18 ml) in DCM (5 ml) was shaken for one hour at room temperature. Triacetoxy borohydride (0.128 g) was added and the reaction mixture was shaken for 16 hours at room temperature. Methanol (1 ml) was added and the mixture was shaken for 5 minutes, then filtered, washed three times with DCM, methanol and dried under vacuum, yielding a residue (1).

Thionyl chloride (0.0020 mole) was added to 4'-(trifluoromethyl)-[1,1'-biphenyl]-2-carboxylic acid (0.00055 mole) in DCM (2 ml) and the mixture was refluxed for 30 minutes while stirring followed by evaporation of the solvent. The residue was dissolved in DCM (5 ml) and the solution was added to the above-prepared residue (1). DIPEA (0.0011 mole) was added, followed by the addition of N,N-dimethyl-4-pyridinamine (0.00008 mole). The reaction mixture was shaken for 21 hours at room temperature, then filtered, washed three times with DCM, then three times with first a 4% acetic acid/DCM mixture, secondly DCM and finally three times with first DCM and secondly methanol, then dried, and 4 ml of a mixture of TFA/DCM/TIS (49/49/2) was added. This mixture was shaken for one hour, filtered, washed with 2 ml of a mixture of TFA/DCM/TIS (49/49/2) and DCM (2 ml). The filtrate was blown dry with nitrogen at 50° C. bCM (5 ml) was added, then removed under a nitrogen stream at 50° C., yielding 0.080 g of methyl α-phenyl-1-[4-[[[4'-(trifluoromethyl)[1,1'-biphenyl]-2-yl]carbonyl]amino]phenyl]-4-piperidineacetate trifluoroacetate (1:1) identified as compound No. 37 in the following table. F-1.

EXAMPLE B.7

4'-(Trifluoromethyl)-[1,1'-biphenyl]-2-carboxylic acid (0.00033 mole) and PyBOP (0.171 g) were dissolved in DCM (5 ml). This mixture was added to the resin of example A.22 (0.00066 mole). DIPEA (0.00066 mole) was added and the reaction mixture was shaken for 48 hours at room temperature, filtered and the residue was washed three time with DMF, then three times with DCM and methanol, dried, yielding a residue. Said residue and a TFA/DCM/TIS (5:93:2) (4 ml) was shaken for 30 minutes at room temperature, then filtered, washed with a mixture of TFA/DCM/TIS (5/93/2) (2 ml) and DCM (2 ml), then the filtrates were blown dry with nitrogen gas at 50° C., then dried further under vacuum at 60° C., yielding 0.030 g of N-[4-[4-[2-oxo-1-phenyl-2-(propylamino)ethyl]-1-piperidinyl]phenyl]-4'-(trifluoromethyl)-[1,1'-biphenyl]-2-carboxamide trifluoroacetate (1:1) identified as compound No. 38 in the following table F-1.

EXAMPLE B.8

DMF (0.5 ml) was added to a solution of 4'-(trifluoromethyl)-[1,1'-biphenyl]-2-carboxylic acid (0.014 mole) in DCM (50 ml) and thionyl chloride (0.028 mole). The mixture was stirred and refluxed for one hour. The solvent was evaporated. DCM (50 ml) was added twice and the solvent was evaporated. The residue was dissolved in DCM (20 ml) and this solution was added to a mixture of intermediate (15) (0.014 mole) and DIPEA (0.028 mole) in DCM (80 ml). The mixture was stirred at room temperature for three hours and washed with water. The organic layer was dried and the solvent was evaporated. The residue was crystallized from 2-propanol. The precipitate was filtered off and dried, yielding 6.2 g of methyl α-phenyl-1-[4-[[[4'-(trifluoromethyl)-[1,1'-biphenyl]-2-yl]carbonyl]amino]phenyl]-4-piperidineacetate (melting point 151° C.) identified as compound No. 39 in the following table F-1.

EXAMPLE B.9

A mixture of intermediate (6) (0.023 mole) and $Na_2CO_3$ (0.023 mole) in DMF (150 ml) was stirred. Methyl α-bromo-α-phenylacetate (0.023 mole) was added dropwise. The mixture was stirred overnight. The solvent was evaporated. The residue was dissolved in DCM. The organic layer was separated, washed, dried, filtered and the solvent was evaporated. The residue was triturated in DIPE. The precipitate was filtered off and dried, yielding 11.4 g of methyl α-phenyl-4-[4-[[[4'-(trifluoromethyl)[1,1 '-biphenyl]-2-yl]carbonyl]amino]phenyl]-1-piperazineacetate identified as compound No. 40 in the following table F-1.

EXAMPLE B.10

A mixture of intermediate (8) (0.018 mole) and $Na_2CO_3$ (0.03 mole) in DMF (100 ml) was stirred. Methyl α-bromo-α-phenylacetate (0.025 mole) was added dropwise. The mixture was stirred overnight. The solvent was evaporated. The residue was dissolved in DCM. The organic layer was separated, washed, dried, filtered and the solvent was evaporated. The residue was purified by column chromatography over silica gel (eluent: $CH_2Cl_2$/$CH_3OH$ 99/1). The pure fractions were collected and the solvent was evaporated, yielding 7.2 g of methylphenyl-4-[4-[[[4'-(trifluoromethyl)[1,1'-biphenyl]-2-yl]carbonyl]amino]phenyl]-1-piperidineacetate (melting point 138° C.) identified as compound No. 41 in the following table F-1.

EXAMPLE B.11

Methyl α-bromo-α-phenylacetate (0.1 mole) was added dropwise to a stirring mixture of intermediate (10) (0.07 mole) and Na$_2$CO$_3$ (13 g) in DMF (300 ml). The mixture was stirred overnight. The solvent was evaporated. The residue was crystallized from methanol. The precipitate was filtered off and dried, yielding 30.2 g of methyl 4-[4-[([1, 1'-biphenyl]-2-ylcarbonyl)amino]phenyl]-α-phenyl-1-piperazineacetate (melting point 125° C.) identified as compound No. 52 in the following table F-1.

EXAMPLE B.12 a) A mixture of compound (40) (0.19 mole) in HCl (36%) (100 ml) was stirred and refluxed for five hours, then stirred overnight at room temperature. The precipitate was filtered off and triturated under 2-propanol, filtered off and dried, yielding 5 g of the intermediate compound α-phenyl-4-[4-[[[4'-(trifluoromethyl)[1,1'-biphenyl]-2-yl]carbonyl]amino] phenyl]piperazineacetic acid monohydrochloride.

b) A mixture of the intermediate compound obtained in step (a) (0.00016 mole), PyBOP (0.00032 mole) and triethylamine (0.1 ml) in DCM (5 ml) was stirred for 30 minutes. Ethylamine (0.0005 mole) was added and the reaction mixture was stirred overnight at 40° C. The reaction mixture was cooled. Water (2 ml) was added and the mixture was stirred for 15 minutes, then filtered through Extrelut™, and the desired compound was isolated by high performance liquid chromatography, yielding 0.046 g of N-[4-[4-[2-(ethylamino)-2-oxo-1-phenylethyl]-1-piperazinyl]phenyl]-4'-(trifluoromethyl)-[1,1'-biphenyl]-2-carboxamide (melting point 123° C.) identified as compound No. 54 in the following table F-1.

Compounds identified as No. 55 to No. 61 in the following table F-1 were similarly prepared while using the same experimental procedure and replacing ethylamine by the appropriate reactive amine.

EXAMPLE B.13

A mixture of α-phenyl-4-[4-[[[4'-(trifluoromethyl)[1,1'-biphenyl]-2-yl]carbonyl]amino]-phenyl]-1-piperazineacetic acid monohydrochloride (0.011 mole) in sulfuric acid (10 ml) and propanol (150 ml) was stirred and refluxed overnight. The solvent was evaporated. The residue was dissolved in DCM and washed with a solution of Na$_2$CO$_3$. The organic layer was separated, washed, dried, filtered and the solvent was evaporated. The residue was purified by column chromatography over silica gel (eluent: CH$_2$Cl$_2$/CH$_3$CN 95/5). The pure fractions were collected and the solvent was evaporated. The residue was triturated in DIPE. The precipitate was filtered off and dried, yielding 2.6 g of propyl-phenyl-4-[4-[[[4'-(trifluoromethyl)[1,1'-biphenyl]-2-yl]carbonyl]amino]phenyl]-1-piperazineacetate (melting point 151° C.) identified as compound No. 62 in the following table F-1.

EXAMPLE B.14

A mixture of intermediate (6) (0.017 mole) and ethyl 2-phenylacrylate (0.017 mole) in DMF (100 ml) was stirred for two days. Na$_2$CO$_3$ (1 g) was added. The mixture was stirred for two days. The solvent was evaporated. The residue was dissolved in DCM. The organic layer was separated, washed, dried, filtered and the solvent was evaporated. The residue was triturated in DIPE. The precipitate was filtered off and dried, yielding 10.6 g of ethylphenyl-4-[4-[[[4'-(trifluoromethyl)[1,1'-biphenyl]-2-yl]carbonyl] amino]-phenyl]-1-piperazine propanoate (melting point 195° C.) identified as compound No. 81 in the following table F-1.

EXAMPLE B.15 a) A mixture of compound No. 81 (0.016 mole) in HCl (36%) (100 ml) was stirred and refluxed for eight hours, then cooled and filtered. The residue was triturated in 2-propanol. The precipitate was filtered off and dried. A part (0.2 g) of this fraction was purified by high performance liquid chromatography over RP-18 eluent: (NH$_4$OAc 0.5%/CH$_3$CN 90/10)/CH$_3$OH/CH$_3$CN 75/25/0, 0/50/50 and 75/25/0; column: HYPERPREP 8 µm). The pure fractions were collected and the solvent was evaporated. The residue was triturated in DIPE. The precipitate was filtered off and dried, yielding 0.12 g of the intermediate compound 2-phenyl-4-[4-[[[4'-(trifluoromethyl)[1,1'-biphenyl]-2yl]carbonyl] amino]phenyl]-1-piperazinepropanoic acid (melting point 202° C.).

b) A mixture of the intermediate compound obtained in step (a) (0.00016 mole), PyBOP (0.00032 mole) and triethylamine (0.1 ml) in DCM (5 ml) was stirred for 30 minutes. Propylamine (0.0004 mole) was added and the reaction mixture was stirred overnight at 40° C. The reaction mixture was cooled, washed with water (2 ml), then filtered through Extrelut™, and the extract's solvent was evaporated. The desired compound was isolated by high performance liquid chromatography over Hyperprep RP-C18 BDS (100 g, 100 Å, 8 µm; eluent: [(0.5% NH$_4$OAc in H$_2$O)/CH$_3$CN 90/10)]/CH$_3$OH/CH$_3$CN (0 min) 75125/0, (10 min) 0/50/50, (16 min) 0/0/100, (18.10–20.00 min) 75/25/0). The pure fractions were collected and the solvent was evaporated, yielding of N-[4-[4-[3-oxo-2-phenyl-3-(propylamino)propyl]-1-piperazinyl]phenyl]-4'-(trifluoromethyl)-[1,1'-biphenyl]-2-carboxamide identified as compound No. 63 in the following table F-1.

Compounds identified as No. 64 to No. 67 in the following table F-1 were similarly prepared while using the same experimental procedure and replacing propylamine by the appropriate reactive amine.

EXAMPLE B.16 a) A mixture of compound No. 41 (0.012 mole) in HCl (36%) (100 ml) was stirred and refluxed for six hours, then stirred overnight at room temperature. The precipitate was filtered off and triturated under 2-propanol. The precipitate was filtered off and dried, yielding 6.2 g of the intermediate compound α-phenyl-4-[4-[[[4'-(trifluoromethyl)[1,1'-biphenyl]-2-yl]carbonyl]amino]phenyl]-1-piperidineacetic acid monohydrochloride.

b) A mixture of the intermediate compound obtained in step (a) (0.00017 mole), PyBOP (0.3 g) and triethylamine (0.1 ml) in DCM (5 ml) was stirred for 30 minutes. Ethylamine (0.00017 mole) was added. The reaction mixture was stirred overnight at 40° C., then cooled and water (2 ml) was added. The mixture was stirred for one hour, then filtered through Extrelut™, and the filtrate was evaporated. The residue was purified by column chromatography over silica gel (eluent: CH$_2$Cl$_2$/CH$_3$OH 90/10). The product fractions were collected and the solvent was evaporated, yielding 0.010 g of N-[4-[1-[2-(ethylamino)-2-oxo-1-phenylethyl]-4-piperidinyl]phenyl]-4'-(trifluoromethyl)-[1,1'-biphenyl]-2-carboxamide identified as compound No. 69 in the following table F-1.

Compounds identified as No. 70 to No. 80 in the following table F-1 were similarly prepared while using the same experimental procedure and replacing ethylamine by the appropriate reactive amine.

EXAMPLE B.17

The resin of example A.23 (0.000045 mole) was washed twice with dioxane. 1,4-Dioxane (1 ml) was added. 2,4-Difluorophenylboronic acid (0.0004 mole) in 1,4-dioxane (1 ml) was added. KOH (2 M) (0.25 ml) was added. The mixture was shaken for 30 minutes under an argon atmosphere. $PdCl_2(PPh_3)_2$ (0.00001 mole) in NMP (0.250 ml) was added. The mixture was stirred for 90 minutes at 98° C. Again, $PdCl_2(PPh_3)_2$ was added and the reaction mixture was warmed for 90 minutes at 98° C. The mixture was allowed to cool to room temperature, then filtered and the filter residue was washed three times with dioxane, three times with water and three times with methanol, then three times with DCM then methanol, finally three times with DCM. F (4 ml) was added. The mixture was shaken for 30 minutes, filtered, washed with TFA/DCM/TIS (2 ml, 5/93/2) and DCM (2 ml), and the filtrates were blown dry with a stream of nitrogen. The residue was purified by high performance liquid chromatography over Purospher Star RP-18 (20 g, 5 μm; eluent: ((0.5% $NH_4OAc$ in $H_2O$)/$CH_3CN$ 90/10)/$CH_3OH$/$CH_3CN$ (0 min) 75/25/0, (10.00 min) 0/50/50, (16.00 min) 0/0/100, (18.10–20 min) 75/25/0). The desired fractions were collected and the organic solvent was evaporated. The aqueous concentrate was extracted with $CH_2Cl_2/Na_2CO_3$ solution. The extract was purified through Extrelut™ and the organic phase was blown dry with a stream of nitrogen. The residue was dried under vacuum at 60° C., yielding 0.008 g of 2',4'-difluoro-N-[4-[4-[2-oxo-1-phenyl-2-(propylamino)ethyl]-1-piperidinyl]phenyl]-[1,1'-biphenyl]-2-carboxamide identified as compound No. 84 in the following table F-1.

Compound identified as No. 68 in the following table F-1 was similarly prepared while using the same experimental procedure.

EXAMPLE B.18

The resin of example A.19 (0.0001 mole) was washed three times with dioxane. 1,4-Dioxane (3 ml) was added. 2-Methylphenylboronic acid (0.0008 mole) in dioxane (1 ml) was added. KOH (2 M) (0.8 ml) was added. The mixture was shaken for 30 minutes under argon atmosphere. $PdCl_2(PPh_3)_2$ (0.00002 mole) in NMP (0.5 ml) was added. The mixture was shaken for two hours at 96° C. Again, $PdCl_2(PPh_3)_2$ in 0.5 ml of NMP was added and the mixture was warmed for two hours at 96° C. The mixture was allowed to cool to room temperature, then filtered and the filter residue was washed three times with DMF, three times with H2O, three times with DMF, three times with methanol, three times with DCM, three times with methanol, and three times with methanol. A mixture of TFA/DCM/TIS (4 ml) was added. The mixture was shaken for 60 minutes at room temperature, filtered, washed with a mixture of TFA/DCM/TIS (2 ml) and DCM (2 ml), and the filtrates were blown dry with a stream of nitrogen. The residue was purified by high performance liquid chromatography over Purospher Star RP-18 (20 g, 5 μm; eluent: ((0.5% $NH_4OAc$ in $H_2O$)/$CH_3CN$ 90/10)/$CH_3OH$/$CH_3CN$ (0 min) 75/25/0, (10.00 min) 0/50/50, (16.00 min) 0/0/100, (18.10–20 min) 75/25/0), yielding 0.004 g of N-[4-[4-[2-(ethylamino)-2-oxo-1-phenylethyl]-1-piperidinyl]phenyl]-2'-methyl-[1,1'-biphenyl]-2-carboxamide identified as compound No. 85 in the following table F-1.

Compounds identified as No. 86 to No. 96 in the following table F-1 were similarly prepared while using the same experimental procedure.

EXAMPLE B.19

Argon gas was bubbled through a mixture of the resin of example A.23 (0.0001 mole) and 3,5-dichlorobenzeneboronic acid (0.0008 mole) in $K_2CO_3$ (2M in $H_2O$) (0.0008 mole) and 1,4-dioxane (5 ml) for five minutes. Palladium (II) acetate (0.00001 mole) in dioxane (0.5 ml) was added and the reaction mixture was warmed and shaken for sixteen hours at 97° C., then cooled, filtered, washed with DMF (three times), water (three times), DMF (three times), then three times with firstly methanol and secondly DCM. A mixture of TFA/DCM/TIS (4 ml, 5/93/2) was added and the mixture was shaken for one hour then filtered. A mixture of TFA/DCM/TIS (2 ml, 5/93/2) was added. The mixture was shaken for 10 minutes, then filtered, washed with DCM (3 ml) and the filtrate was blown dry under nitrogen at 50° C. The residue was purified by HPLC over Purospher Star RP-18-e (20 g, 5 μm; eluent: ((0.5% $NH_4OAc$ in $H_2O$)/$CH_3CN$ 90/10)/$CH_3OH$/$CH_3CN$ (0 min) 75/25/0, (10.00 min) 0/50/50, (16.00 min) 0/0/100, (18.10–20 min) 75/25/0). The desired fractions were collected and the organic solvent was evaporated. The aqueous concentrate was extracted with $CH_2Cl_2$/aqueous $K_2CO_3$ solution. The extract was purified through Extrelut™ and the organic phase was blown dry with a stream of nitrogen. The residue was dried under vacuum at 60° C., yielding 0.008 g of 3',5'-dichloro-N-[4-[4-[2-oxo-1-phenyl-2-(propylamino)ethyl]-1-piperidinyl]phenyl]-[1,1'-biphenyl]-2-carboxamide identified as compound No. 97 in the following table F-1.

Compounds identified as No. 42 to 51, 53, 82, 83, and 98 to 118 in the following table F-1 were similarly prepared while using the same experimental procedure.

EXAMPLE B.20 a) A suspension of 2,2'-bis(diphenylphosphino)-1,1'-binaphtyl (0.086 g, 0.00014 mole) in NMP (1 ml) was added to the resin of example A.38 (0.2 g, 0.00014 mole) and sodium terbutoxide (0.242 g, 0.00252 mole). Homopiperazine (0.126 g, 0.0021 mole) in NMP (2 ml) was added and the mixture was stirred under argon. Tris(dibenzylidene acetone) di-palladium (0.026 g, 0.000028 mole) in NMP (1 ml) was added and the reaction mixture was shaken for 19 hours at 105° C. The mixture was cooled, filtered and the filter residue was washed with DMF, water, DMF (three times), $H_2O$ (three times), DMF (three times), $CH_3OH$ (three times), CH₂Cl₂ (three times), CH₃OH (three times) and NMP (two times). NMP (3 ml) was added.

b) Methyl-bromophenylacetate (0.16 g, 0.0007 mole) in NMP (1 ml) was added to the product obtained in step (a). DIPEA (0.3 ml) was added and the mixture was shaken for 18 hours at room temperature. The mixture was filtered, washed with DMF and water, then with DMF.(three times), water (three times), DMF (three times), methanol (three times), DCM (three times), methanol (three times) DCM (three times).

TFA/TIS/CH₂Cl₂ (49/2/49) (4 ml) was added and the mixture was shaken for one hour at room temperature. The mixture was filtered and more TFA/TIS/CH₂Cl₂ (49/2/49) (1.5 ml) was added. The mixture was shaken for 15 minutes, filtered, washed with DCM (2 ml), then the filtrates were blown dry under nitrogen. The residue was purified by high performance liquid chromatography over Purospher Star RP-18 (20 g, 5 µm; eluent: ((0.5% NH₄OAc in H₂O)/ CH₃CN 90/10)/CH₃CN/CH₃OH (0 min) 75/25/0, (10.00 min) 0/50/50, (16.00 min) 0/0/100, (18.10–20 min) 75/25/0). The desired fractions were collected and the organic solvent was evaporated. The aqueous concentrate was treated with an aqueous sodium carbonate solution, then extracted with DCM. The extract was separated through Extrelut™ and the filtrates were blown dry under nitrogen at 50° C., yielding 0.021 g of the compound identified as compound 119 in the following table F-1.

Compounds identified as No.120 to No.128 in the following table F-1 were similarly prepared while using the same experimental procedure.

EXAMPLE B.21

A mixture of intermediate (17) (0.019 mol) and Na₂CO₃ (0.019 mol) in DMF (125 ml) was stirred at room temperature. Methyl α-bromo-α-phenylacetate (0.01907 mol) was added dropwise. The mixture was stirred for 3 hours. The solvent was evaporated. The residue was taken up in water and DCM. The separated organic layer was dried, filtered and the solvent was evaporated. The residue was purified by column chromatography over silica gel (eluent: CH₂Cl₂/ CH₃OH 100/0; 99.5/0.5). The pure fractions were collected and the solvent was evaporated yielding a residue that separated in its enantiomers by high performance liquid chromatography over Chiralpak AD (eluent: hexane/ethanol 70/30). The desired fractions were collected and the solvent was evaporated, yielding, after crystallisation from 2-propanol, compound (229), mp. 158° C., $[\alpha]_D^{20}$=−28.86° (c=24.95 mg/5 ml in CH₃OH); and compound (230), mp. 160° C., $[\alpha]_D^{20}$ =+27.69° (c=24.95 mg/5 ml in CH₃OH).

EXAMPLE B.22

Methyl α-bromo-α-phenylacetate (0.0010 mole) in NMP (1 ml) was added to resin (IX-a) (0.0002 mol) in NMP (3 ml). N,N-diisopropylethylamine (0.0023 mol) was added and the reaction mixture was shaken for 48 hours at room temperature, then filtered and the filter residue was washed with DMF (3 times), water (3 times), DMF (3 times), methanol (3 times), DCM (3 times), methanol (3 times) and DCM (3 times). A mixture of TFA/TIS/CH₂Cl₂ (49/2/49) (4 ml) was added. the reaction mixture was shaken for 2 hours at room temperature, then filtered and again a mixture of TFA/TIS/CH₂Cl₂ (49/2/49) (4 ml) was added. The reaction mixture was shaken for another 15 minutes, then filtered and the filtrates were blown dry under nitrogen. The residue was purified by high performance liquid chromatography over Purospher Star RP-18 (20 g, 5 µm; eluent: ((0.5% NH₄OAc in H₂O)/CH₃CN 90/10)/CH₃CN/CH₃OH (0 min) 75/25/0, (10.00 min) 0/50/50, (16.00 min) 0/0/100, (18.10–20 min) 75/25/0). The desired fractions were collected and the organic solvent was evaporated. The aqueous concentrate was treated with an aqueous sodium carbonate solution, then extracted with DCM. The extract was separated through Extrelut™ and the filtrates were blown dry under nitrogen at 50° C., yielding compound (184) in the following table F-1.

EXAMPLE B.23

Dimethylallyl alcohol (0.00017 mol) was added to a mixture of α-phenyl-4-[4-[[[4'-(trifluoromethyl)[1,1'-biphenyl]-2-yl]carbonyl]amino]phenyl]-1-piperidineacetic acid monohydrochloride (as prepared in Example B.16.a) (0.000084 mol) in DCM (4 ml) and N,N-diisopropylethylamine (0.00010 mol) stirred under nitrogen at −20° C. and the mixture was stirred for 10 minutes. 1-[Bis(dimethylamino)methylene]-tetrafluoroborate(1-)-1H-benzotriazolium 3-oxide (TBTU) (0.00013 mol) was added and the reaction mixture was stirred for 30 minutes at −20° C. The mixture was allowed to gradually warm to room temperature and the reaction mixture was stirred for 75 hours at room temperature. The reaction mixture was washed with water (1 ml), then filtered through Extrelut™ and the filter residue was rinsed three times with 3 ml of DCM. The filtrate was evaporated and the residue was purified by HPLC (Waters column, with Xterra MS C18; eluent: [(0.5% NH₄OAc in H₂O)/CH₃CN 90/10)]/CH₃OH/CH₃CN (0 min) 75/25/0, (10 min) 0/50/50, (16 min) 0/0/100, (18.10–20.00 min) 75/25/0). The product fractions were collected and the organic solvent was evaporated. The aqueous concentrates were partitioned between DCM and an aqueous Na₂CO₃ solution. The combined organic layers were separated, dried, filtered and the filtrate was blown dry under nitrogen at 50° C. The residue was dried (vacuum, 60° C.), yielding compound (220).

EXAMPLE B.24

N,N-diisopropylethylamine (0.0010 mol) was added to a mixture of α-phenyl-4-[4-[[[4'-(trifluoromethyl)[1,1'-biphenyl]-2-yl]carbonyl]amino]phenyl]-1-piperidine-acetic acid monohydrochloride (as prepared in Example B.16.a) (0.000084 mol) in DCM (4 ml). Ethanol (0.00017 mol) and 1-[bis(dimethylamino)methylene]-tetrafluoroborate(1-)-1H-benzotriazolium 3-oxide (TBTU) (0.00013 mol) were added. The reaction mixture was stirred for 75 hours at room temperature. Water (1 ml) was added. The mixture was stirred for 30 minutes, then filtered through Extrelut™, rinsed 3 times with DCM (3 ml each time) and the filtrate was evaporated. The residue was dissolved in DCM, washed with 1 ml of 1 N HCl, filtered through Extrelut™ and the filtrate was washed with a saturated aqueous NaHCO₃ solution (1 ml). This mixture was filtered through Extrelut™. The filtrate was collected, and the filter residue was washed with DCM (2×4 ml). The filtrate was evaporated. Each residue was purified by HPLC (Waters column, with Xterra MS C18; eluent: [(0.5% NH$_4$OAc in H$_2$O)/CH$_3$CN 90/10)]/CH$_3$OH/CH$_3$CN (0 min) 75/25/0, (10 min) 0/50/50, (16 min) 0/0/100, (18.10–20.00 min) 75/25/0). The product fractions were collected and the organic solvent was evaporated. The aqueous concentrates were partitioned between DCM and an aqueous Na$_2$CO$_3$ solution. The combined organic layers were separated, dried, filtered and the filtrate was blown dry under nitrogen at 50° C. The residue was dried (vacuum, 60° C.), yielding compound (222).

EXAMPLE B.25 a) A mixture of compound (39) (0.0014 mol) in concentrated HCl (25 ml) and dioxane (20 ml) was stirred and refluxed for 4 hours, cooled and poured out into water. The mixture was extracted with DCM. The organic layer was separated, dried, filtered and the solvent was evaporated. The residue was triturated in DIPE. The precipitate was filtered off and dried, yielding 0.48 g of α-phenyl-1-[4-[[[4'-(trifluoromethyl)[1,1'-biphenyl]-2-yl]carbonyl]amino]phenyl]-4-piperidineacetic acid (intermediate 26) (mp. 196° C.).
b) Ethylbromide (1.2 equivalent, 0.00010 mol) was added to a mixture of intermediate (26) (0.000084 mol) in DMF (5 ml) and Cs$_2$CO$_3$ (0.00018 mol) and the reaction mixture was stirred for 3 hours at 70° C. The solvent was evaporated. The residue was partitioned between water and DCM. The extract's solvent was evaporated. The residue was purified by HPLC (Waters column, with Xterra MS C18; eluent: [(0.5% NH$_4$OAc in H$_2$O)/CH$_3$CN 90/10)]/CH$_3$CN (0 min) 85/15, (10 min) 10/90, (16 min) 0/100, (18.10–20.00 min) 85/15). The product fractions were collected and the organic solvent was evaporated. The aqueous concentrates were extracted and the extract's solvent was evaporated, yielding compound (243).

EXAMPLE B.26

Acetyl chloride (0.0007 mol) was added to resin (XI) (0.00011 mol) in DCM (4 ml). N,N-dimethyl-4-pyridinamine (0.00011 mol) was added. N,N-diisopropyl-ethylamine (0.0011 mol) was added and the reaction mixture was shaken overnight at room temperature. The mixture was filtered and the filter residue was washed with DCM, methanol, DCM, methanol, CHDCM2Cl2, methanol, and DCM. TFA/TIS/CH$_2$Cl$_2$ (49/2/49) (4 ml) was added and the mixture was shaken for 2 hours at room temperature. The mixture was filtered, More TFA/TIS/CH$_2$Cl$_2$ (49/2/49) (2 ml) was added and the mixture was shaken for 15 minutes, then filtered and the filter residue was washed with DCM (2 ml). The filtrates were blown dry under nitrogen. The residue was purified by HPLC over Purospher Star RP-18 (20 g, 5 μm; eluent: ((0.5% NH$_4$OAc in H$_2$O)/CH$_3$CN 90/10)/CH$_3$OH/CH$_3$CN (0 min) 75/25/0, (10.00 min) 0/50/50, (16.00 min) 0/0/100, (18.10–20 min) 75/25/0). The desired fractions were collected and the organic solvent was evaporated. The aqueous concentrate was extracted and the extract's solvent was evaporated, yielding 0.001 g of compound (253).

EXAMPLE B.27

Methanol (0.5 ml) was added to resin (XII) (0.0002 mol) in DCM (4 ml). N,N-dimethyl-4-pyridinamine (0.0002 mol) was added. DIPEA (0.002 mol) was added and the reaction mixture was shaken for 18 hours at room temperature. The mixture was filtered and the filter residue was washed with DCM (3×), methanol (3×), DCM (3×), methanol (3×), DCM (3×), methanol (3×), DCM (3×). TFA/TIS/CH$_2$Cl$_2$ (49/2/49) (4 ml) was added and the mixture was shaken for 2 hours at room temperature. The mixture was filtered, More TFA/TIS/CH$_2$Cl$_2$ (49/2/49) (2 ml) was added and the mixture was shaken for 15 minutes, then filtered and the filter residue was washed with DCM (2 ml). The filtrates were blown dry under nitrogen. The residue was purified by HPLC over Purospher Star RP-18 (20 g, 5 μm; eluent: ((0.5% NH$_4$OAc in H$_2$O)/CH$_3$CN 90/10)/CH$_3$OH/CH$_3$CN (0 min) 75/25/0, (10.00 min) 0/50/50, (16.00 min) 0/0/100, (18.10–20 min) 75/25/0). The desired fractions were collected and the organic solvent was evaporated. The aqueous concentrate was extracted and the extract's solvent was evaporated, yielding 0.002 g of compound (251).

EXAMPLE B.28

A mixture of intermediate (31) (0.0006 mol), ethylamine hydrochloride (0.0015 mol), EDCI (0.0007 mol), HOBT (0.0007 mol) and triethylamine (0.0015 mol) in DCM (10 ml) was stirred at room temperature overnight. Water was added. The mixture was extracted with DCM. The organic layer was separated, dried, filtered, and the solvent was evaporated. The residue was purified by column chromatography over kromasil (eluent: DCM). The pure fractions were collected and the solvent was evaporated, yielding 0.034 g of compound (276).

EXAMPLE B.29

A mixture of intermediate (29) (0.0045 mol), 3-thienyl boronic acid (0.036 mol), PdCl$_2$(PPh$_3$)$_2$ (0.0009 mol) and Na$_2$CO$_3$ (0.072 mol) in dioxane (50 ml) was stirred and refluxed for 30 minutes. Water was added. The mixture was extracted with ethyl acetate. The organic layer was separated, dried, filtered, and the solvent was evaporated. The residue was purified by column chromatography over silica gel (eluent: DCM/ethyl acetate 90/10). The pure fractions were collected and the solvent was evaporated, yielding compound (267) (mp. 150° C.).

EXAMPLE B.30

A mixture of intermediate (29) (0.0025 mol), 3-pyridinyl boronic acid (0.02 mol), PdCl$_2$(PPh$_3$)$_2$ (0.005 mol) and Na$_2$CO$_3$ (0.04 mol) in dioxane (30 ml) was stirred and refluxed for 3 hours. Water was added. The mixture was extracted with ethyl acetate. The organic layer was separated, dried, filtered, and the solvent was evaporated. The residue was purified by column chromatography over silica gel (eluent: CH$_2$Cl$_2$/CH$_3$OH/NH$_4$OH 97/3/0.1), yielding compound (270) (mp. 194° C.).

Table F-1 lists the polyarylcarboxamide compounds of the present invention, together with their detailed formulae, that were prepared according to one of the above examples B.1 to B.20. In this table, the abbreviation ".C$_2$HF$_3$O$_2$" stands for the trifluoroacetate salt, ".C$_3$H$_8$O" stands for the 2-propanolate salt, and ".CH$_4$O" stands for the methanolate salt of the said compound.

TABLE F-1
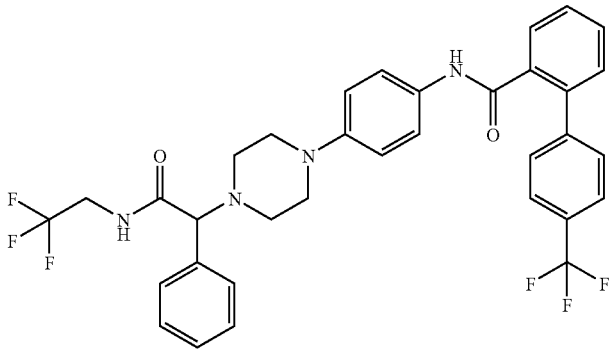
Co. No. 1; Ex. B.1; mp. 208° C.
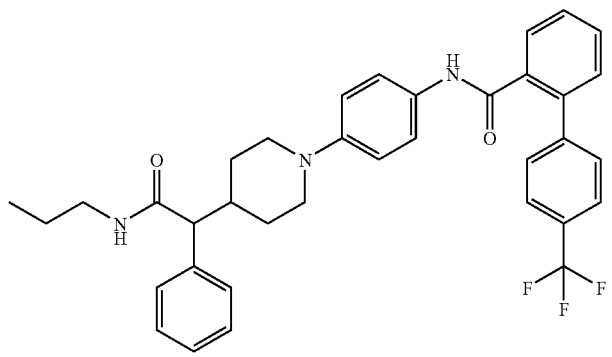
Co. No. 38; Ex. B.7; .C$_2$HF$_3$O$_2$
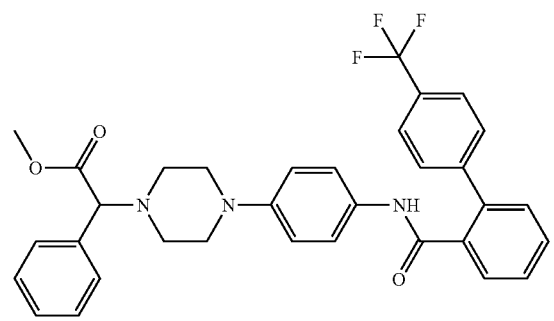
Co. No. 40; Ex. B.9; mp. 143° C.
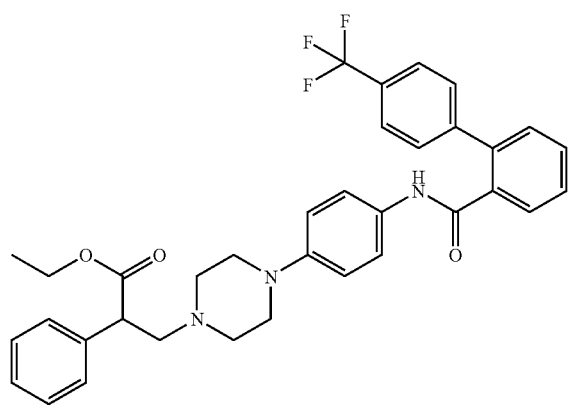
Co. No. 81; Ex. B14; mp. 195° C.

TABLE F-1-continued
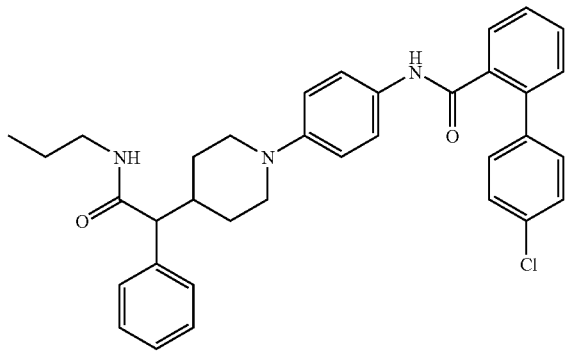
Co. No. 68; Ex. B.17
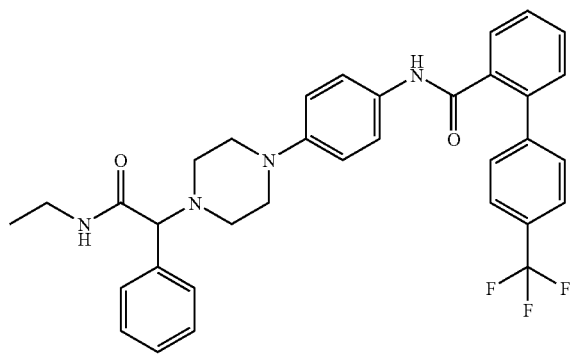
Co. No. 54; Ex. B.12; mp. 123° C.
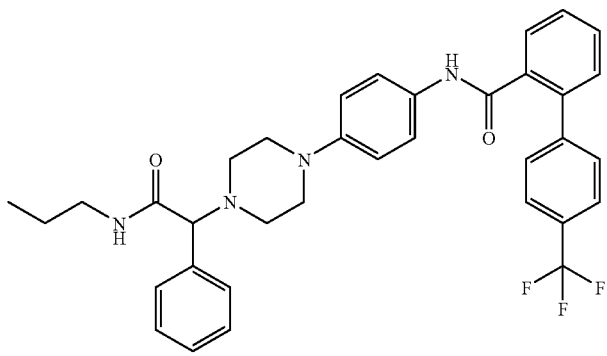
Co. No. 55; Ex. B.12
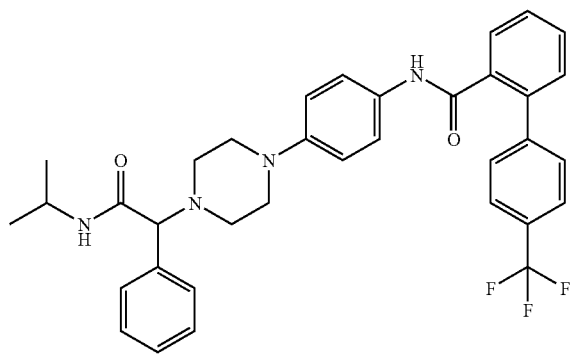
Co. No. 56; Ex. B.12

TABLE F-1-continued
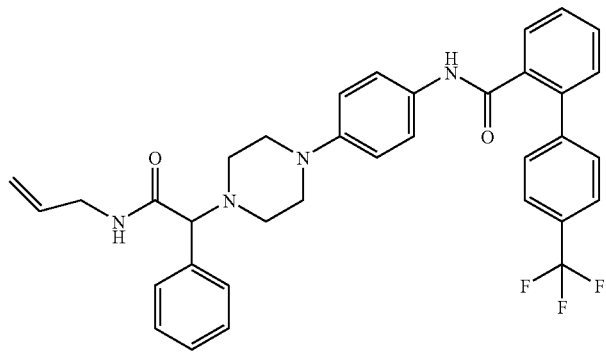
Co. No. 57; Ex. B.12
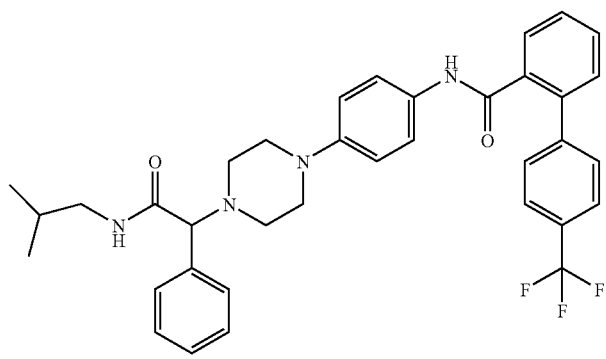
Co. No. 58; Ex. B.12
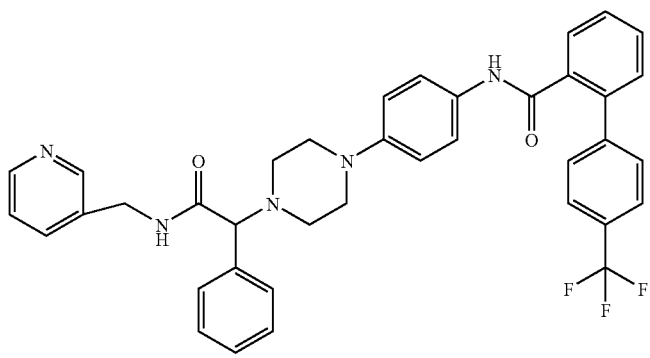
Co. No. 59; Ex. B.12
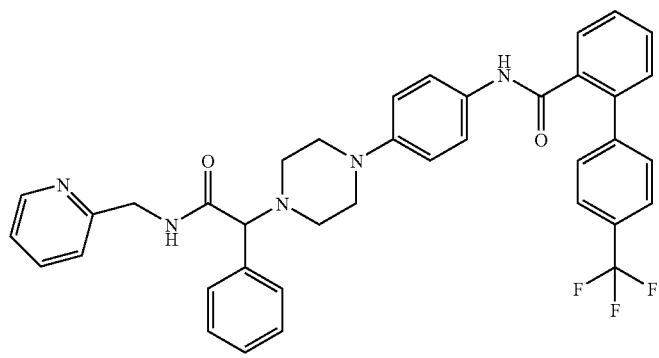
Co. No. 60; Ex. B.12

TABLE F-1-continued
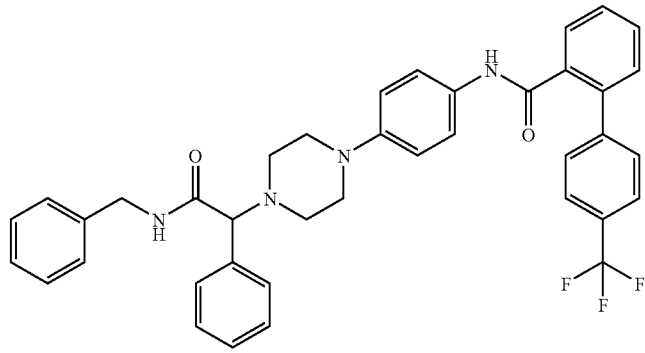
Co. No. 61; Ex. B.12; mp. 142° C.
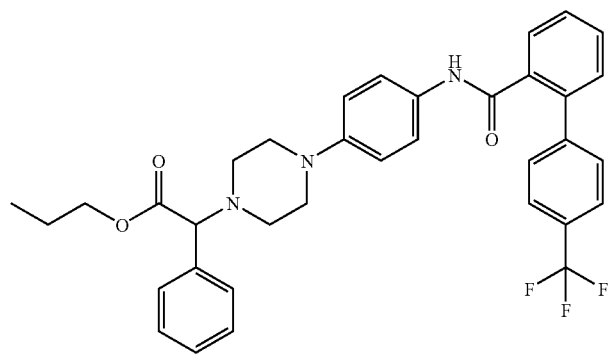
Co. No. 62; Ex. B.13; mp. 151° C.
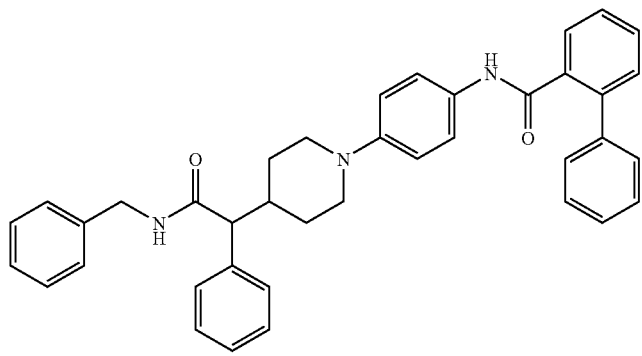
Co. No. 3; Ex. B.2
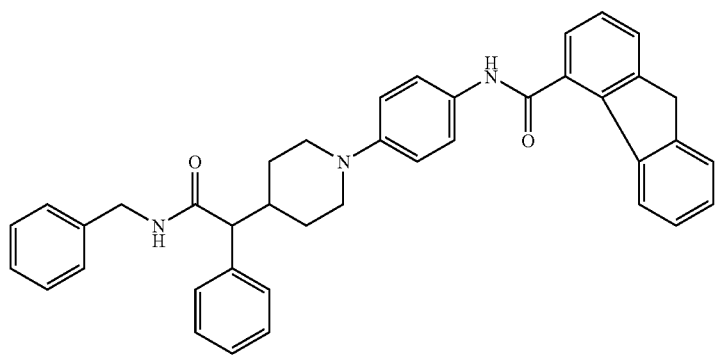
Co. No. 2; Ex. B.2

TABLE F-1-continued
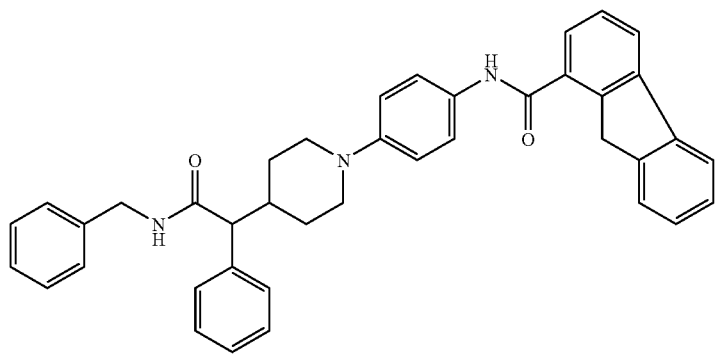
Co. No. 4; Ex. B.2
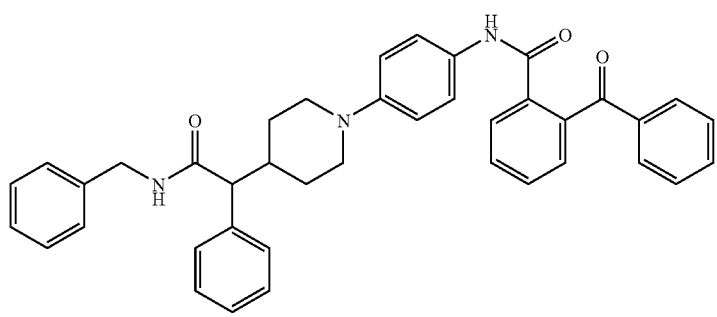
Co. No. 5; Ex. B.2
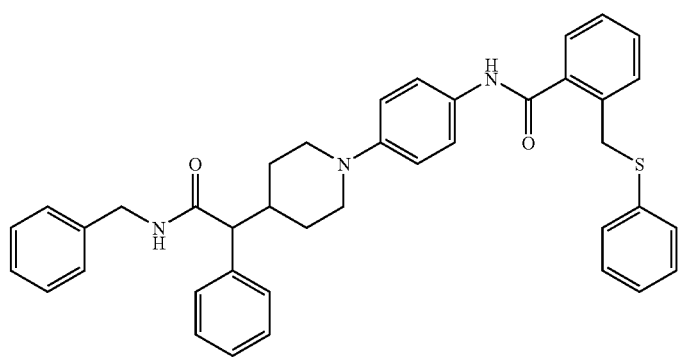
Co. No. 6; Ex. B.2
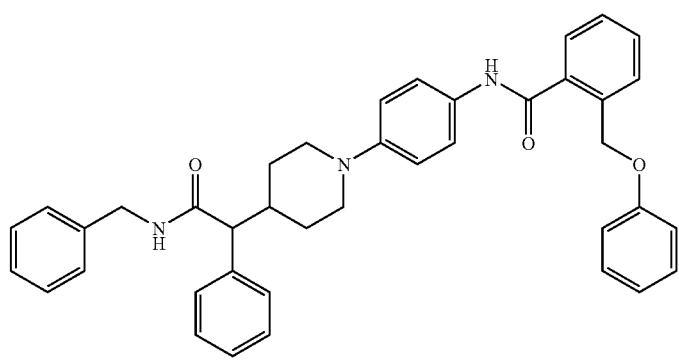
Co. No. 7; Ex. B.2

TABLE F-1-continued
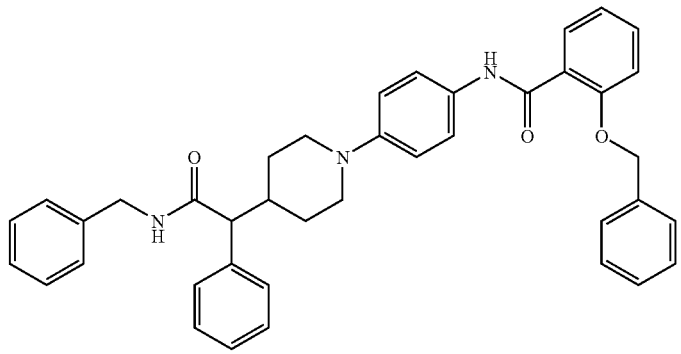
Co. No. 8; Ex. B.2
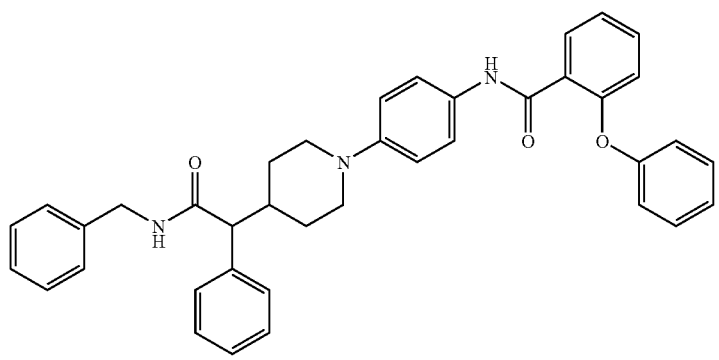
Co. No. 9; Ex. B.2
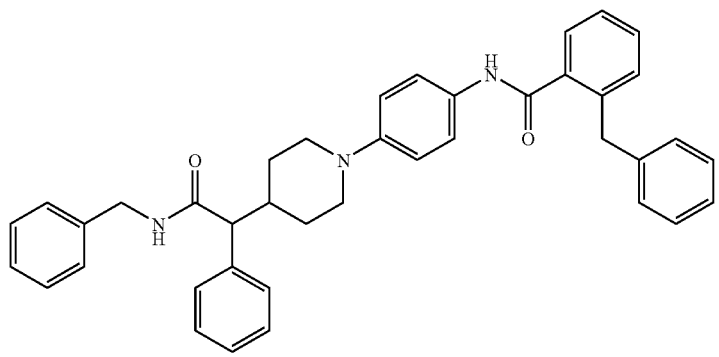
Co. No. 10; Ex. B.2
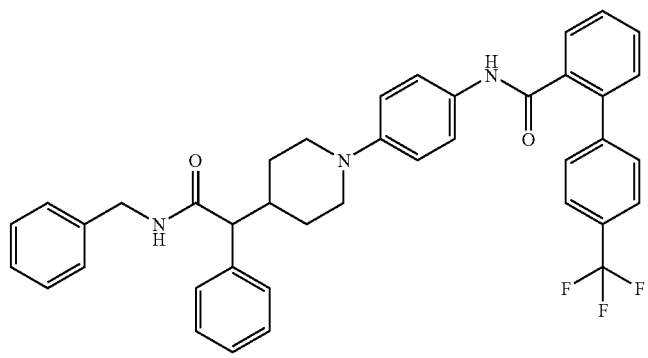
Co. No. 11; Ex. B.2; mp. 218° C.

TABLE F-1-continued
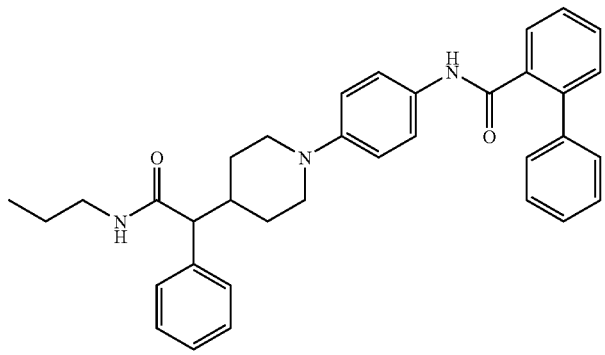
Co. No. 13; Ex. B.3
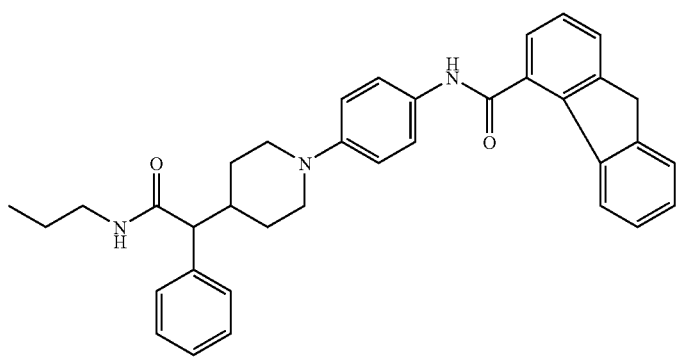
Co. No. 12; Ex. B.3
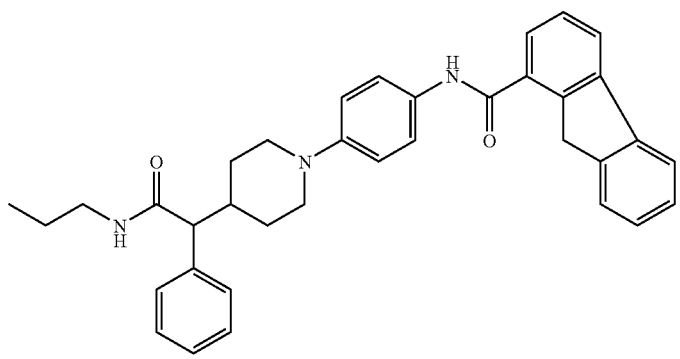
Co. No. 14; Ex. B.3
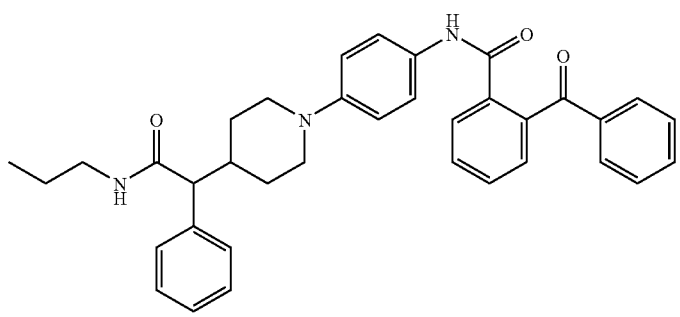
Co. No. 15; Ex. B.3

TABLE F-1-continued
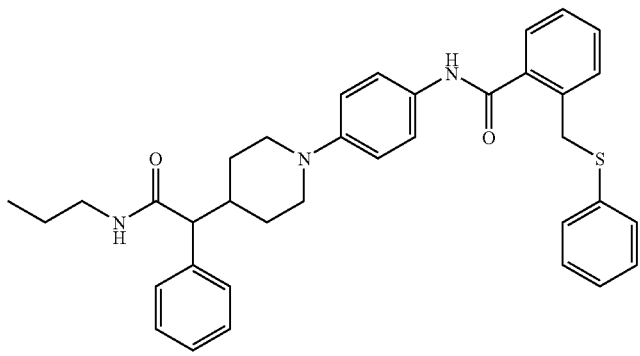
Co. No. 16; Ex. B.3
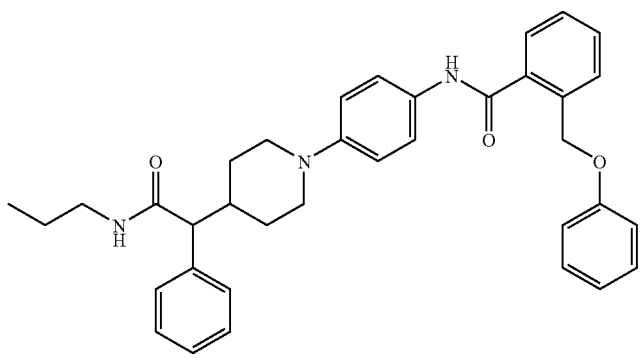
Co. No. 17; Ex. B.3
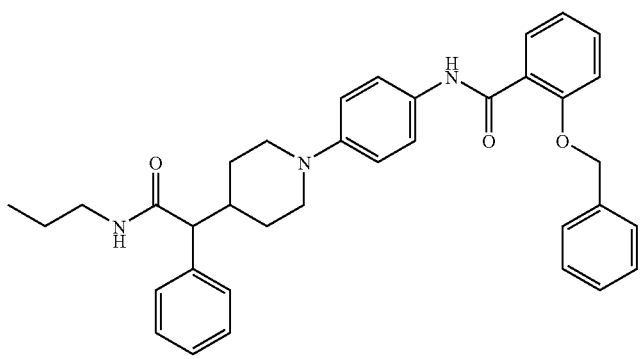
Co. No. 18; Ex. B.3
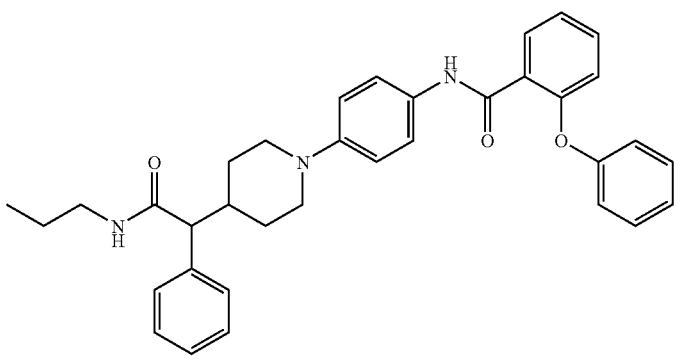
Co. No. 19; Ex. B.3

TABLE F-1-continued
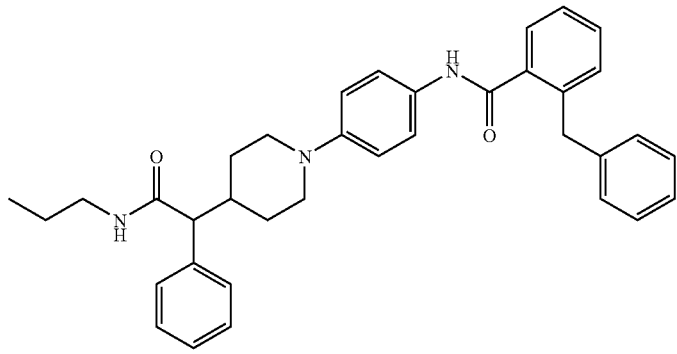
Co. No. 20; Ex. B.3
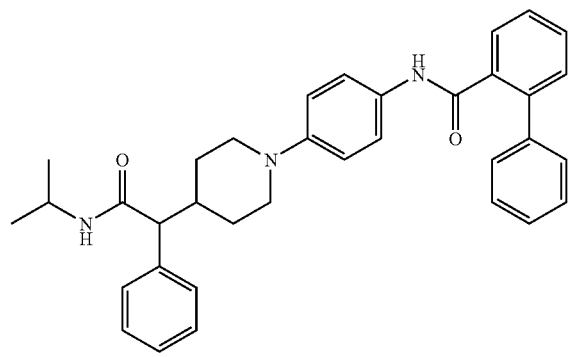
Co. No. 22; Ex. B.4
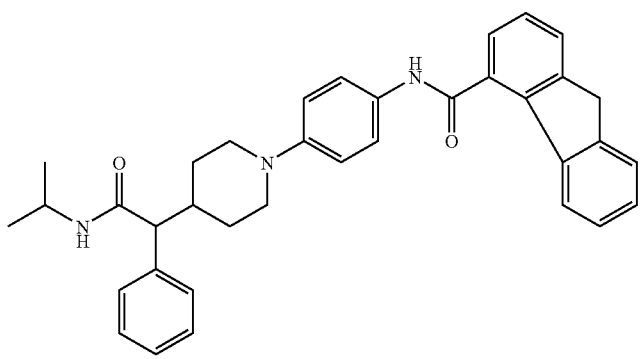
Co. No. 21; Ex. B.4
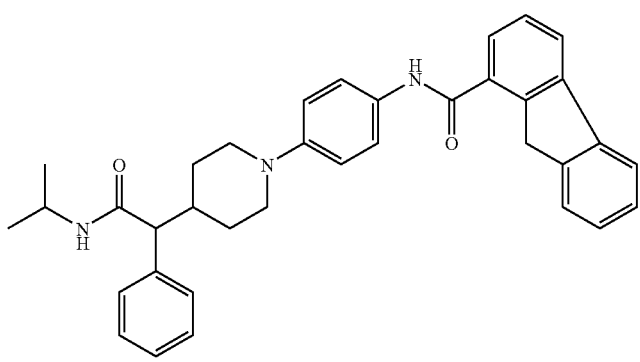
Co. No. 23; Ex. B.4

TABLE F-1-continued
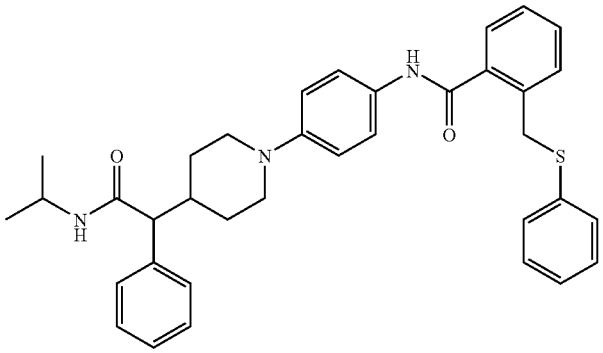
Co. No. 24; Ex. B.4
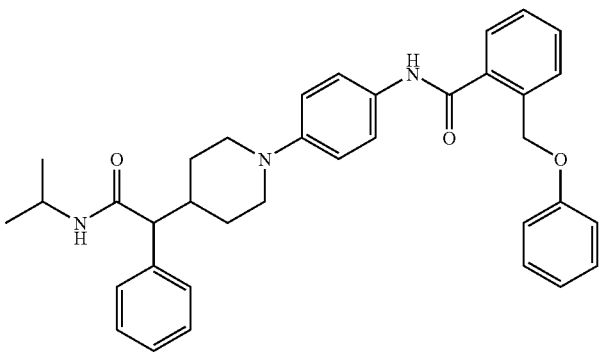
Co. No. 25; Ex. B.4
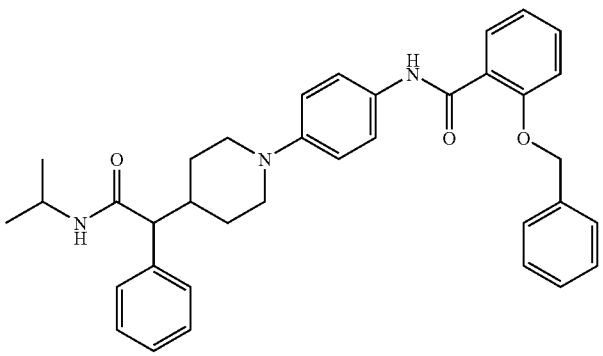
Co. No. 26; Ex. B.4
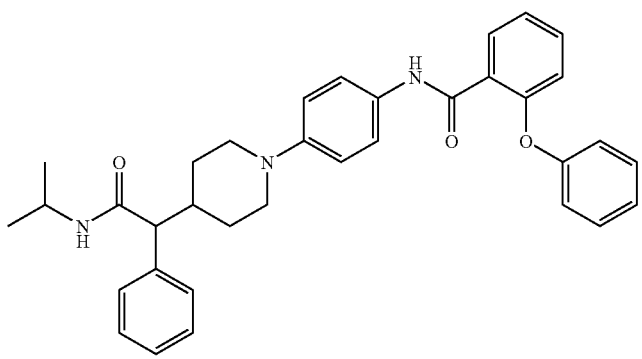
Co. No. 27; Ex. B.4

TABLE F-1-continued
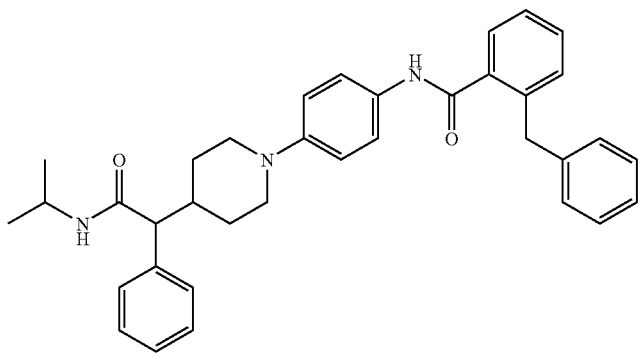
Co. No. 28; Ex. B.4
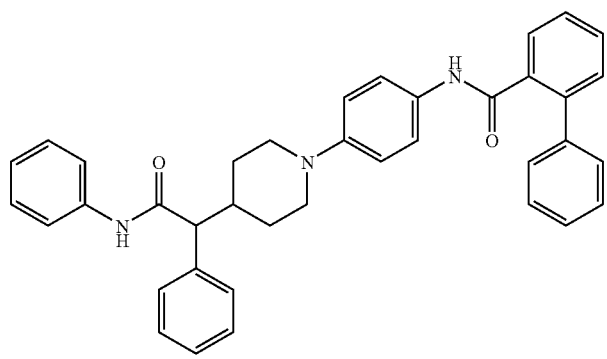
Co. No. 30; Ex. B.5
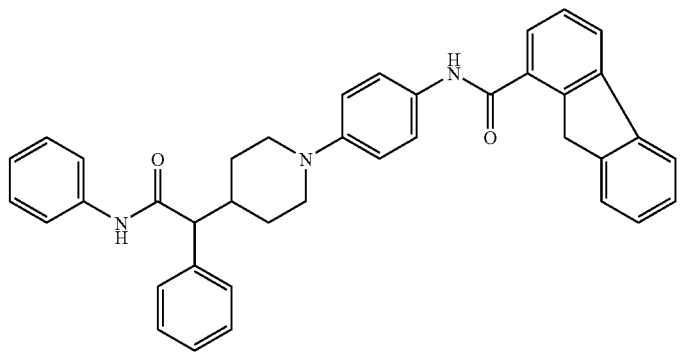
Co. No. 29; Ex. B.5
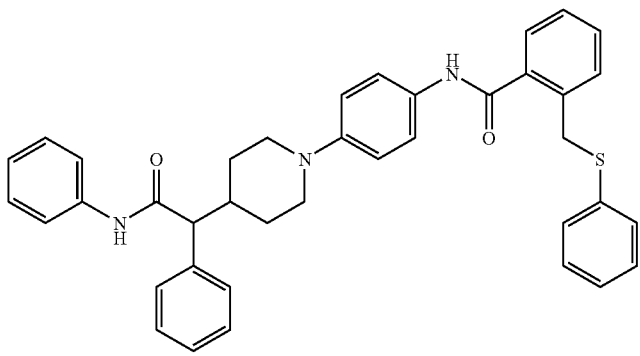
Co. No. 31; Ex. B.5

TABLE F-1-continued
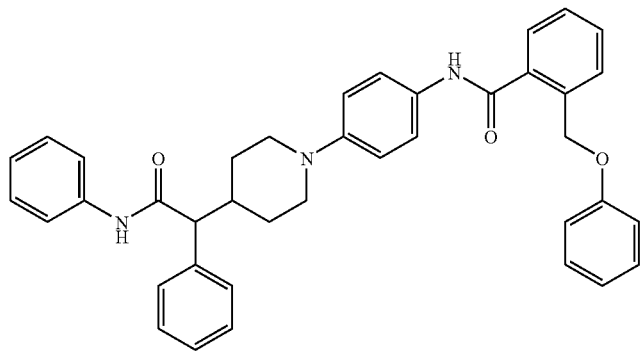
Co. No. 32; Ex. B.5
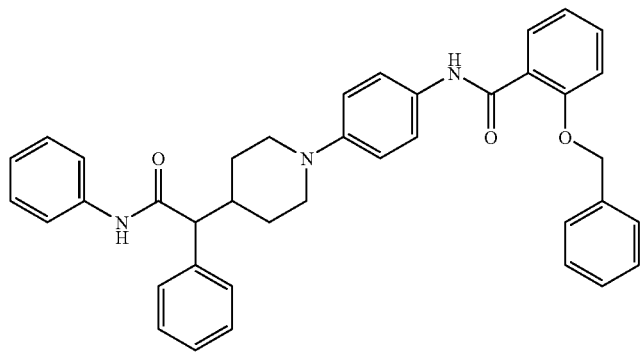
Co. No. 33; Ex. B.5
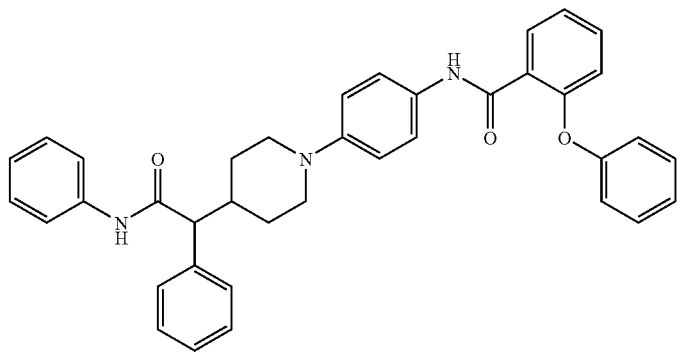
Co. No. 34; Ex. B.5
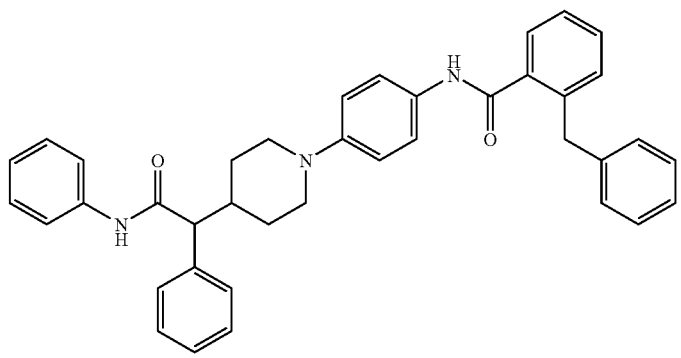
Co. No. 35; Ex. B.5

TABLE F-1-continued
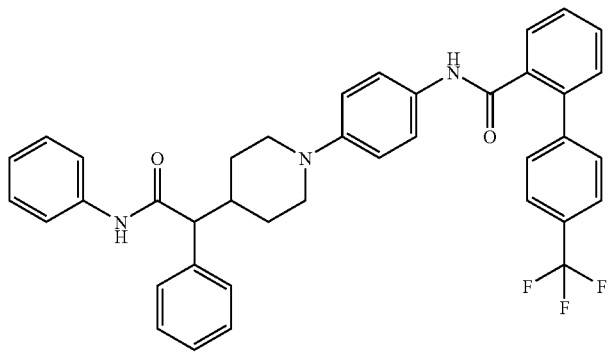
Co. No. 36; Ex. B.5
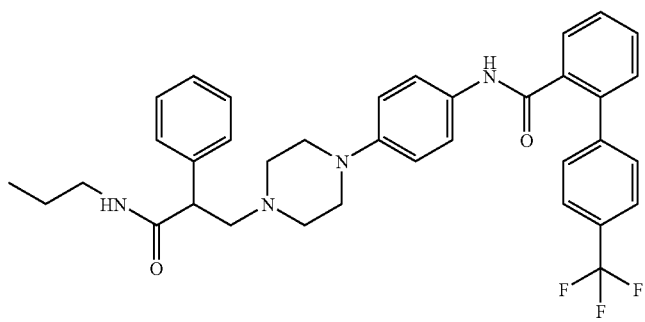
Co. No. 63; Ex. B.15
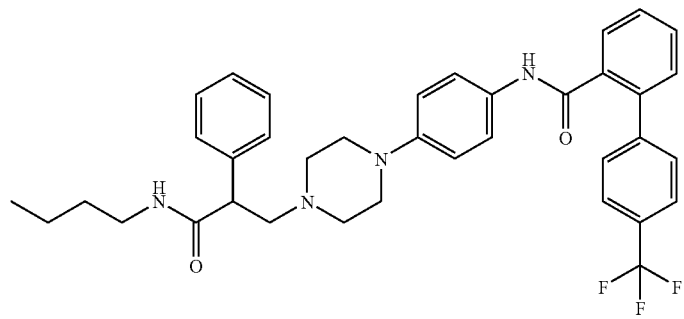
Co. No. 64; Ex. B.15
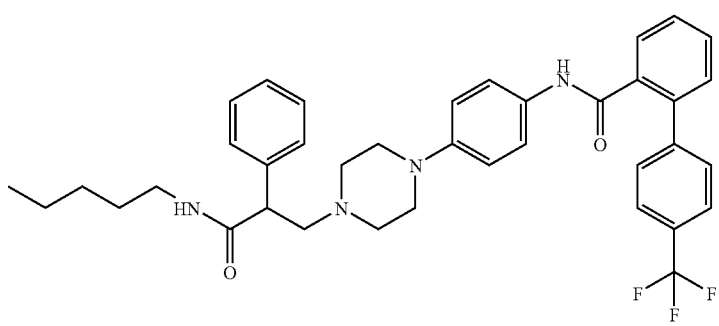
Co. No. 65; Ex. B.15

TABLE F-1-continued
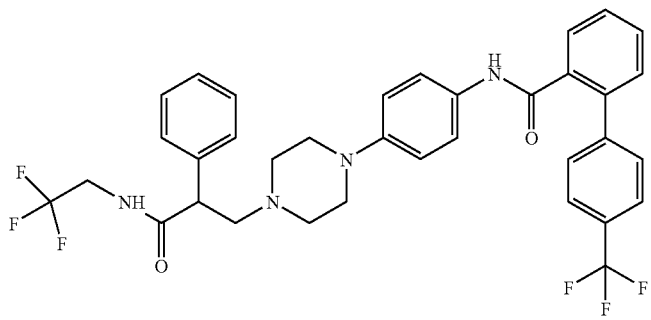
Co. No. 66; Ex. B.15
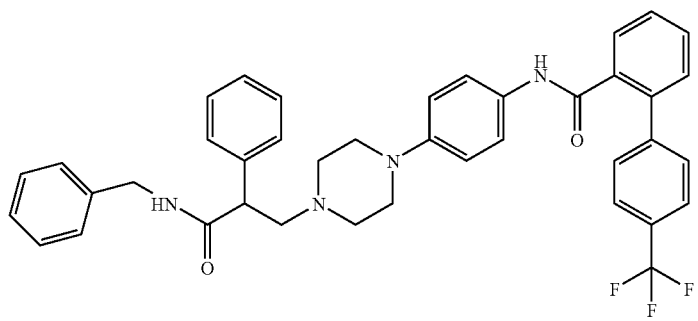
Co. No. 67; Ex. B.15
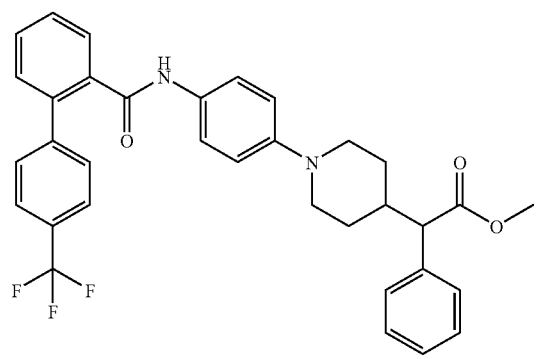
Co. No. 37; Ex. B.6; .C$_2$HF$_3$O$_2$
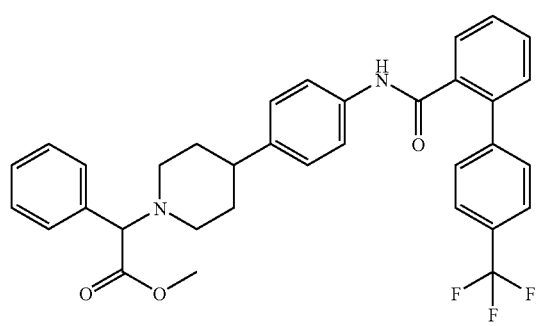
Co. No. 41; Ex. B.10; mp. 138° C.

TABLE F-1-continued
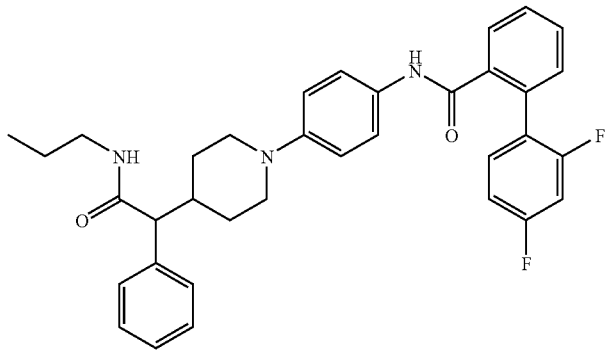
Co. No. 84; Ex. B.17
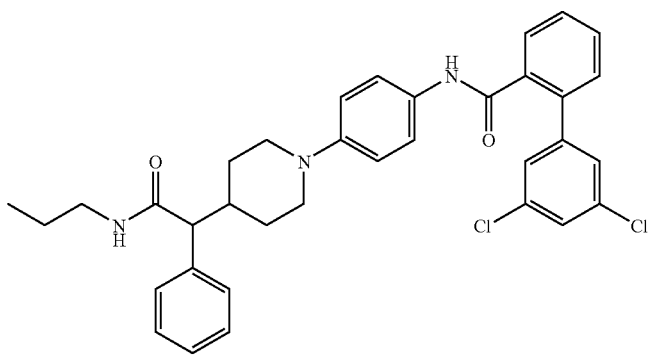
Co. No. 97; Ex. B.19
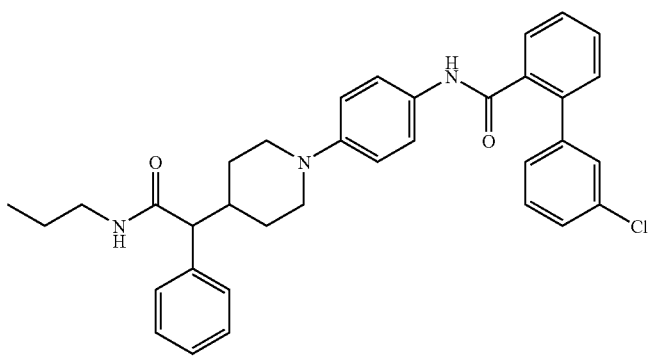
Co. No. 82; Ex. B.19
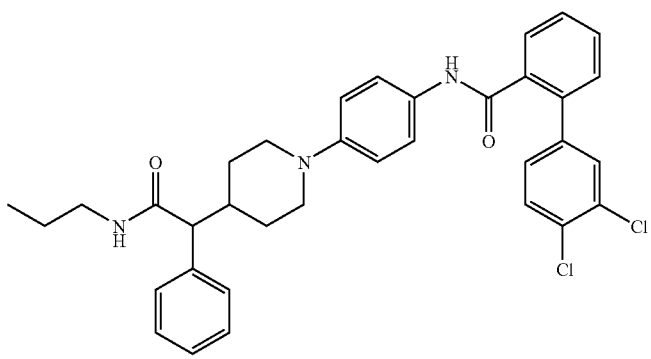
Co. No. 83; Ex. B.19

TABLE F-1-continued
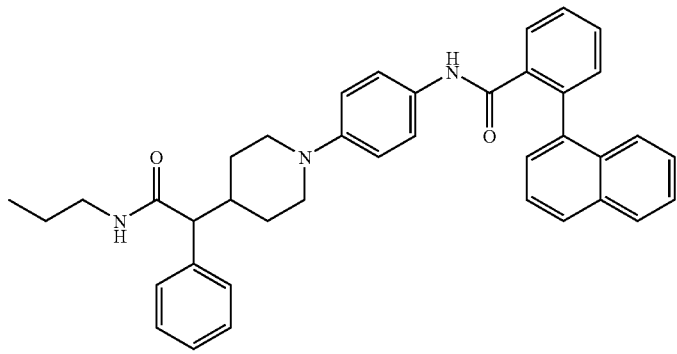
Co. No. 42; Ex. B.19
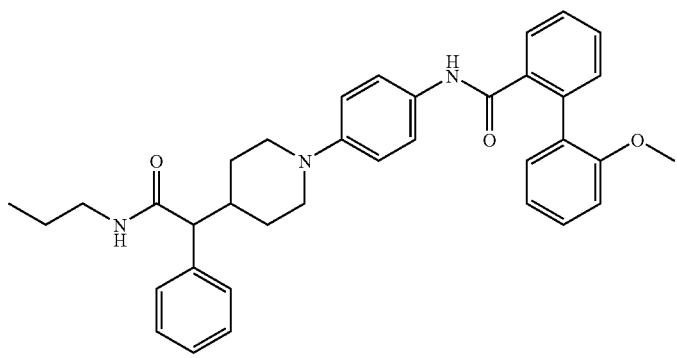
Co. No. 43; Ex. B.19
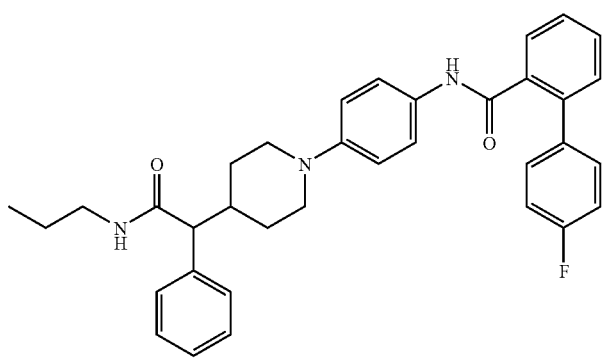
Co. No. 44; Ex. B.19
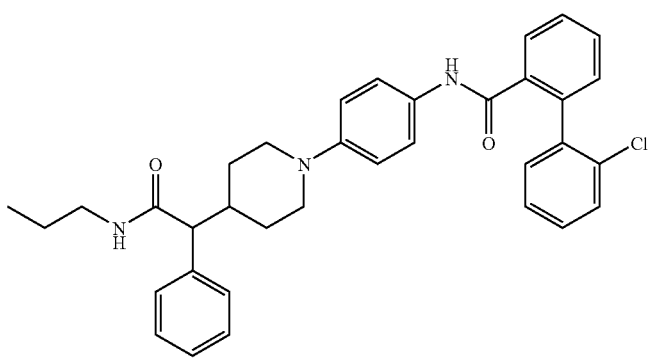
Co. No. 45; Ex. B.19

TABLE F-1-continued
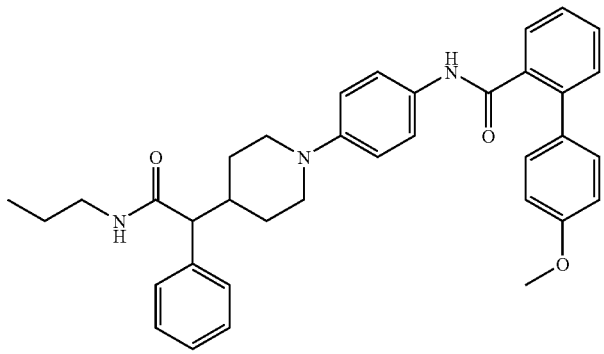
Co. No. 46; Ex. B.19
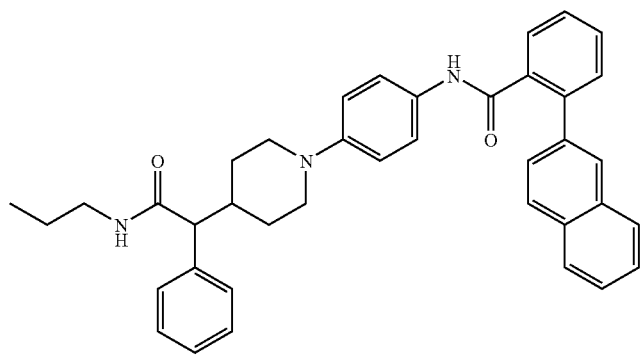
Co. No. 47; Ex. B.19
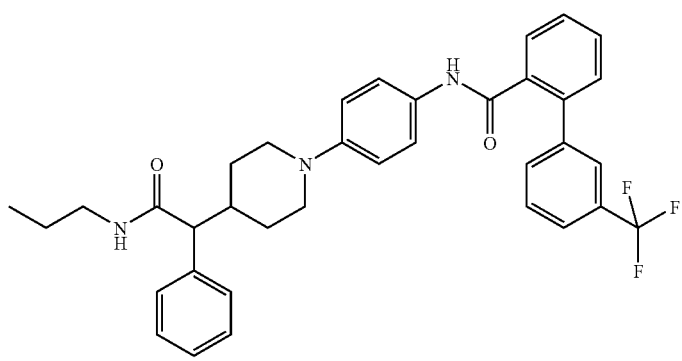
Co. No. 48; Ex. B.19
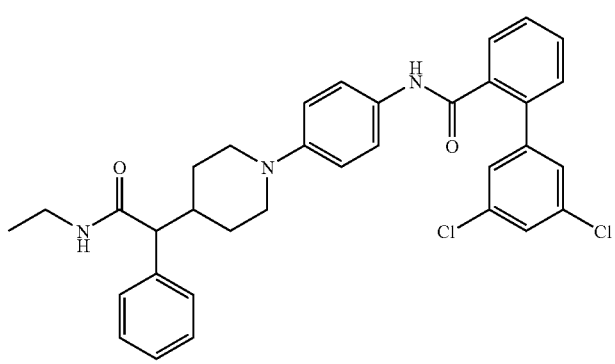
Co. No. 49; Ex. B.19

TABLE F-1-continued
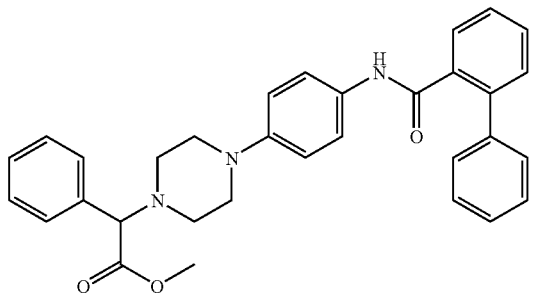
Co. No. 52; Ex. B.11
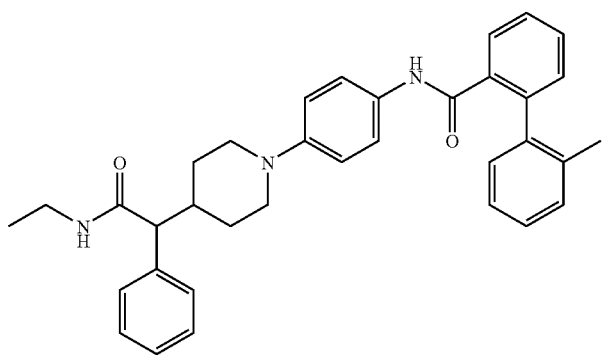
Co. No. 85; Ex. B.18
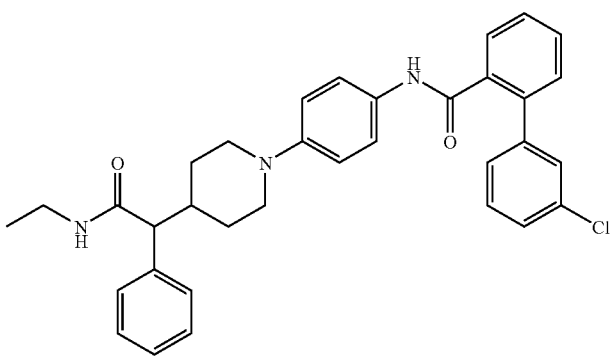
Co. No. 86; Ex. B.18
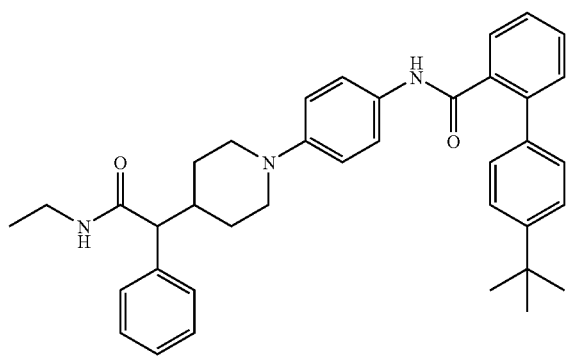
Co. No. 87; Ex. B.18

TABLE F-1-continued
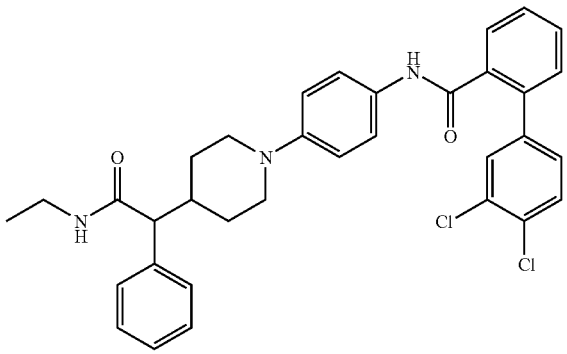
Co. No. 88; Ex. B.18
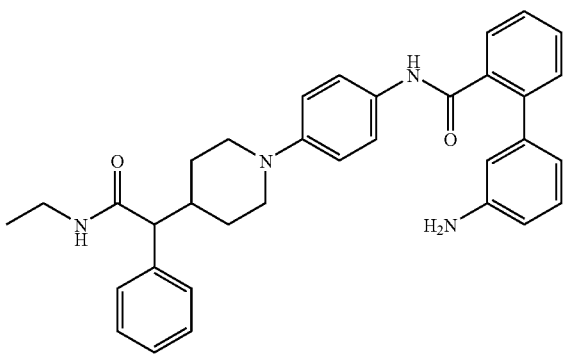
Co. No. 89; Ex. B.18
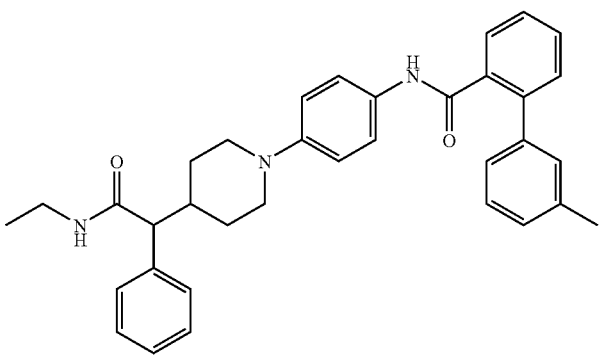
Co. No. 90; Ex. B.18
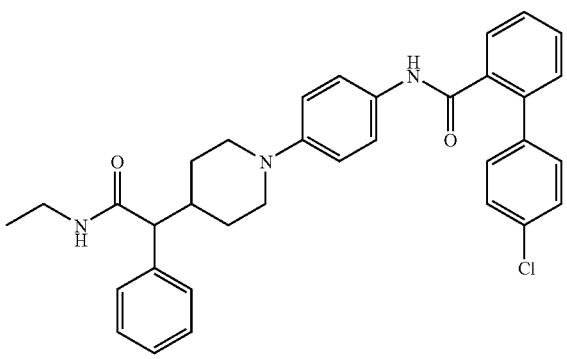
Co. No. 91; Ex. B.18

TABLE F-1-continued
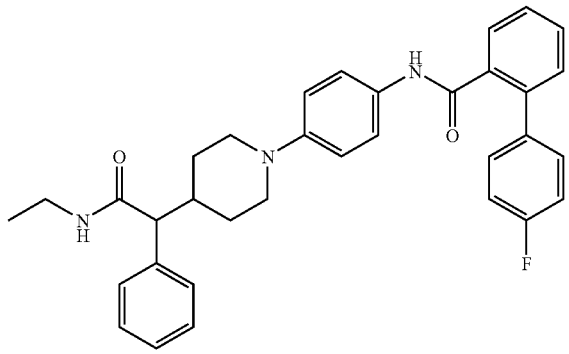
Co. No. 92; Ex. B.18
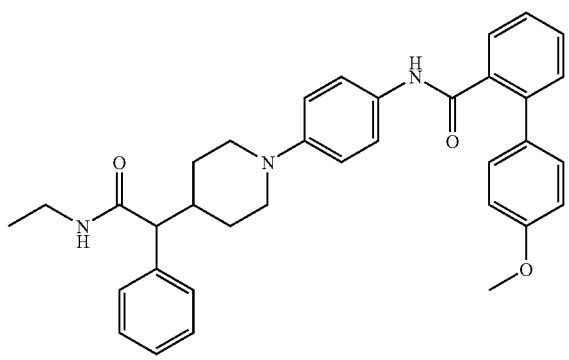
Co. No. 93; Ex. B.18
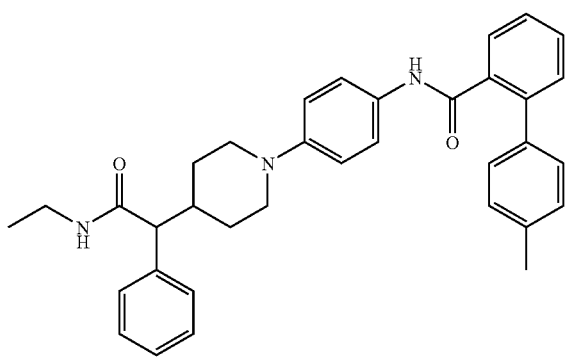
Co. No. 94; Ex. B.18
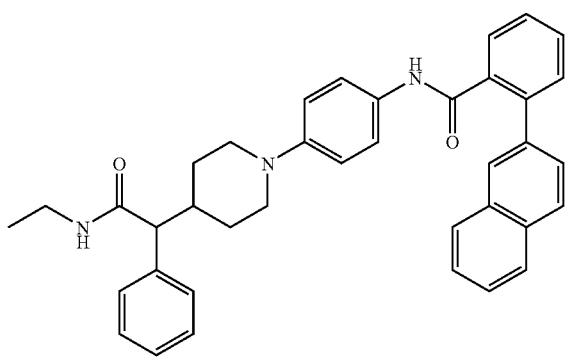
Co. No. 95; Ex. B.18

TABLE F-1-continued
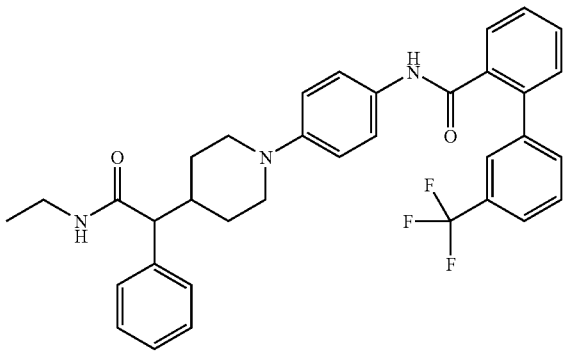
Co. No. 96; Ex. B.18
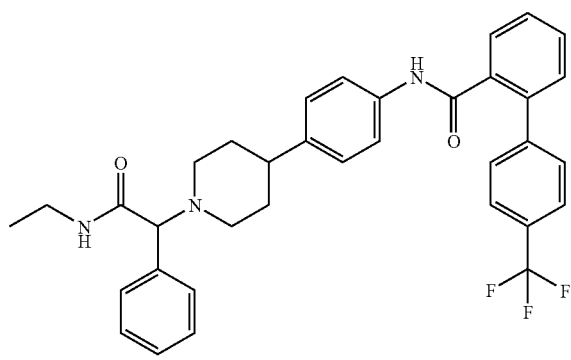
Co. No. 69; Ex. B.16
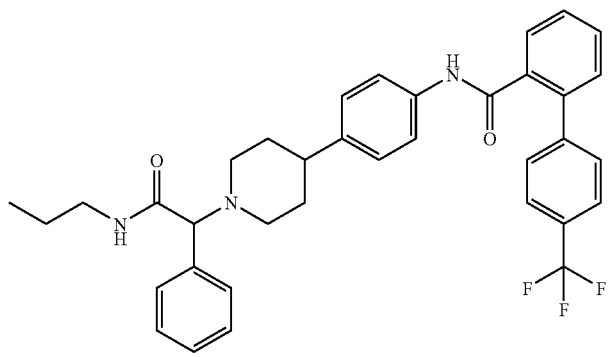
Co. No. 70; Ex. B.16
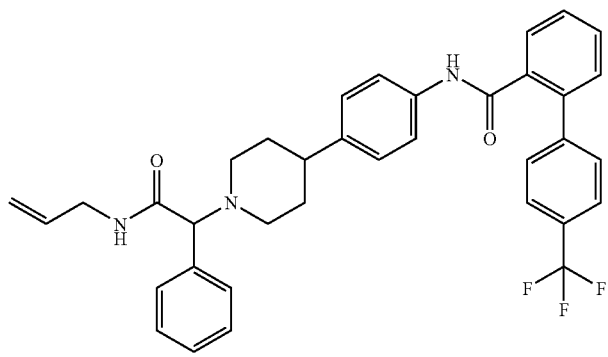
Co. No. 71; Ex. B.16

TABLE F-1-continued
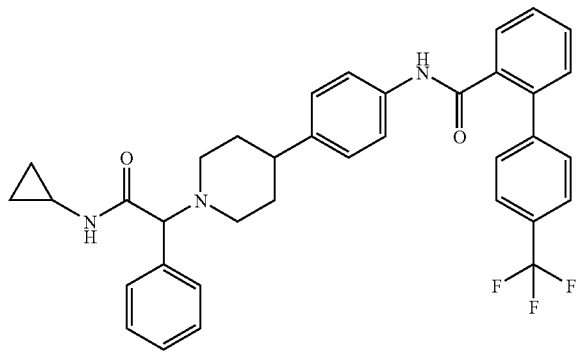
Co. No. 72; Ex. B.16
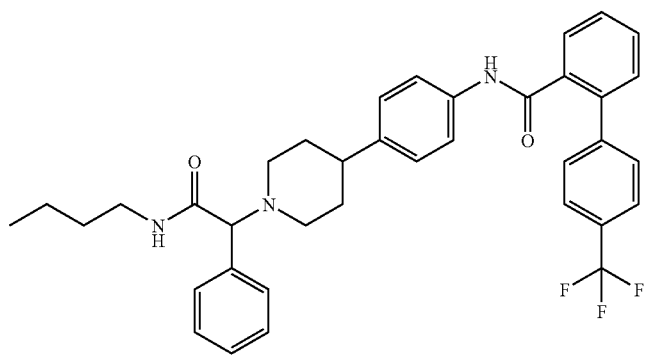
Co. No. 73; Ex. B.16
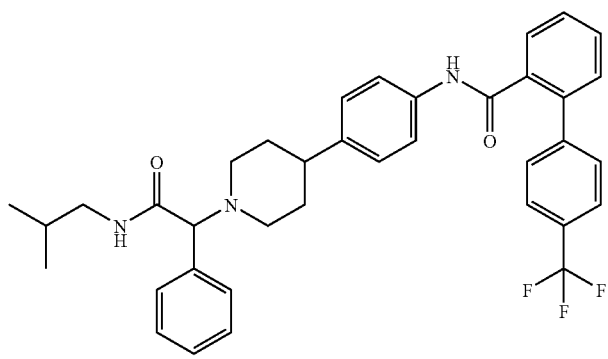
Co. No. 74; Ex. B.16
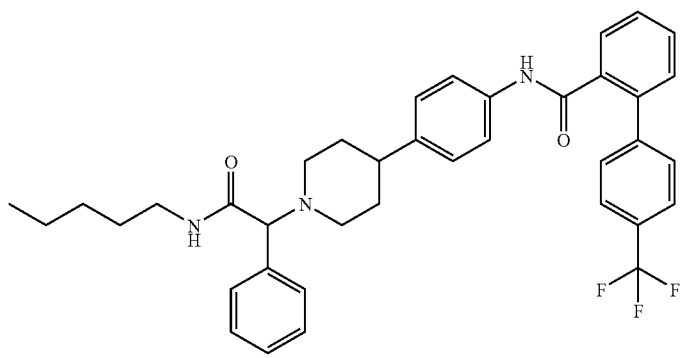
Co. No. 75; Ex. B.16

TABLE F-1-continued
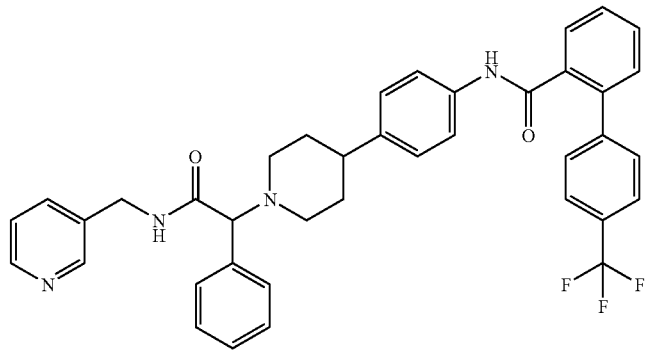
Co. No. 76; Ex. B.16
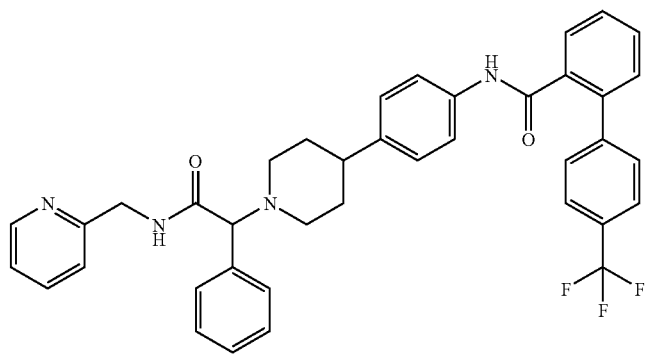
Co. No. 77; Ex. B.16
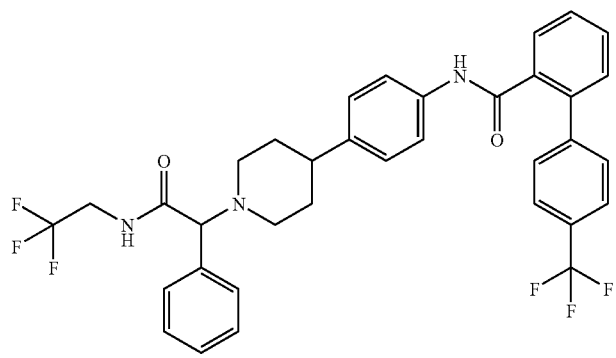
Co. No. 78; Ex. B.16
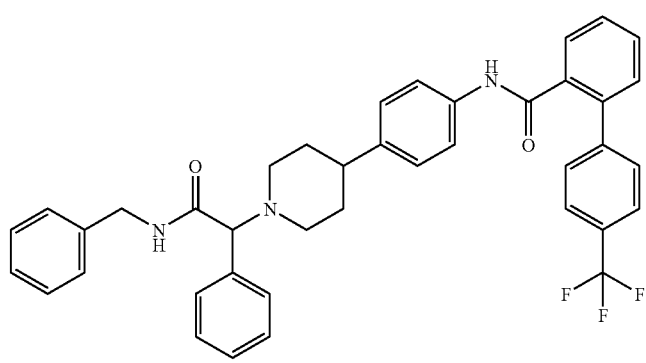
Co. No. 79; Ex. B.16

TABLE F-1-continued
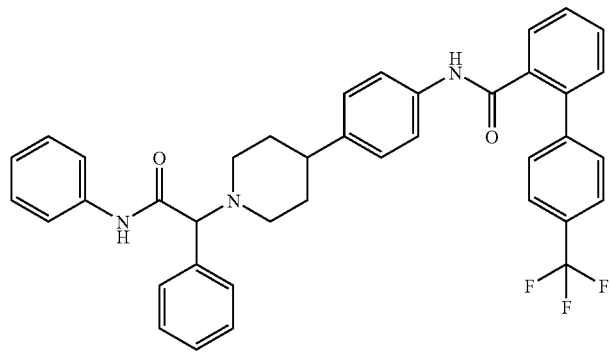
Co. No. 80; Ex. B.16
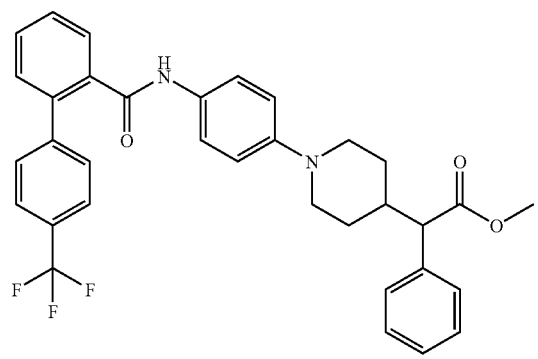
Co. No. 39; Ex. B.8
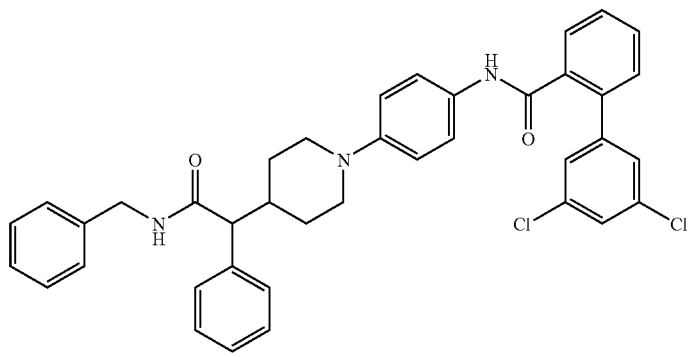
Co. No. 50; Ex. B.19
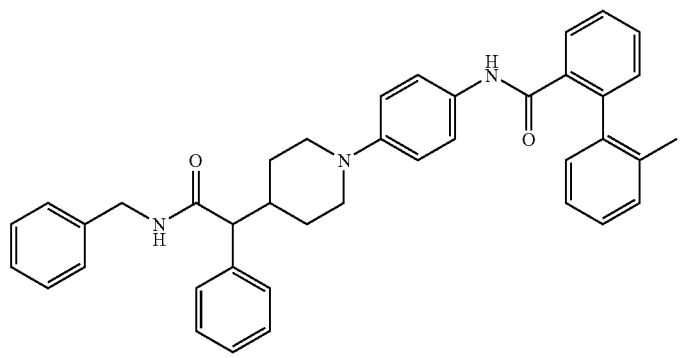
Co. No. 51; Ex. B.19

TABLE F-1-continued
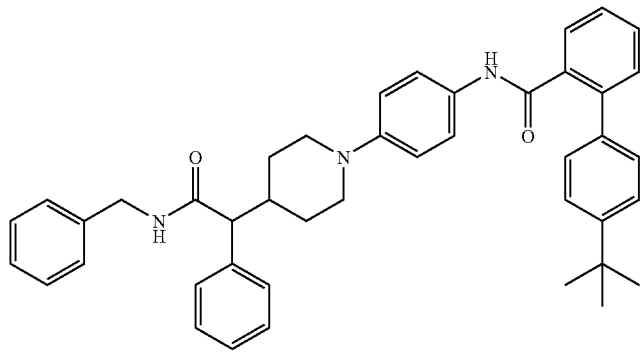
Co. No. 53; Ex. B.19
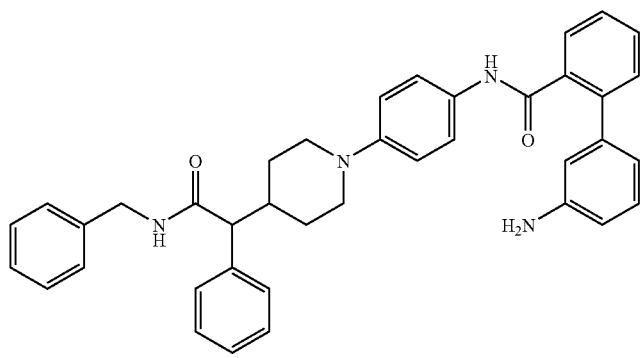
Co. No. 98; Ex. B.19
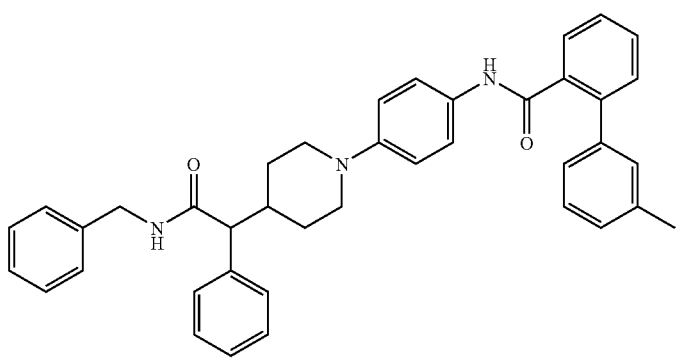
Co. No. 99; Ex. B.19
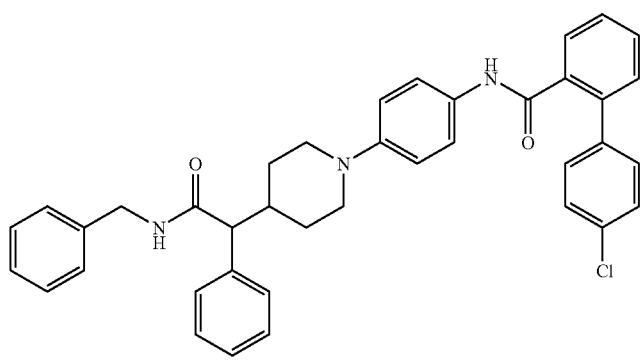
Co. No. 100; Ex. B.19

TABLE F-1-continued
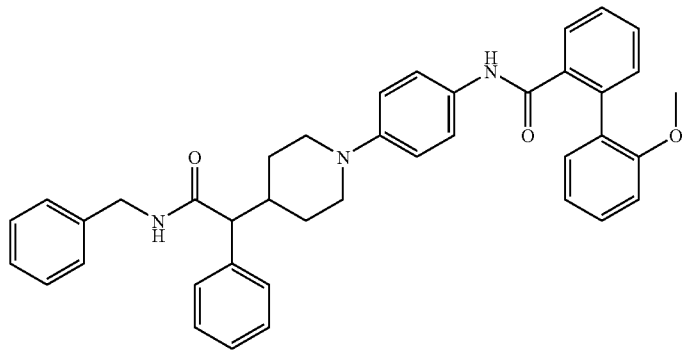
Co. No. 101; Ex. B.19
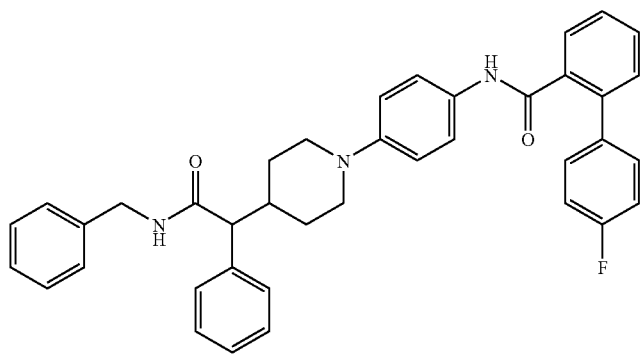
Co. No. 102; Ex. B.19
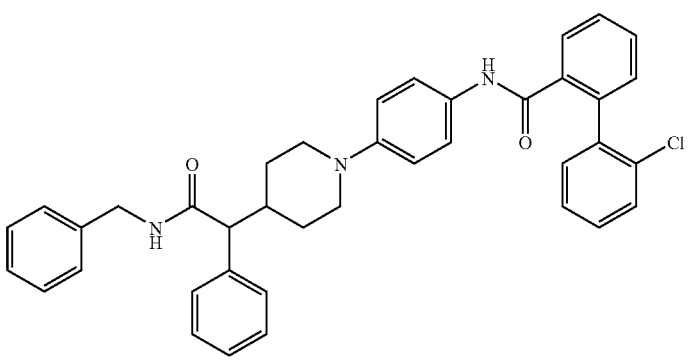
Co. No. 103; Ex. B.19
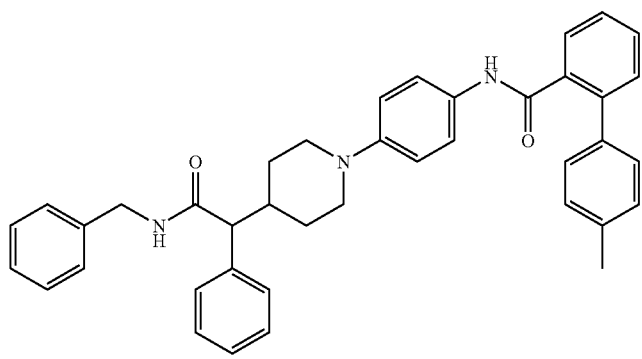
Co. No. 104; Ex. B.19

TABLE F-1-continued
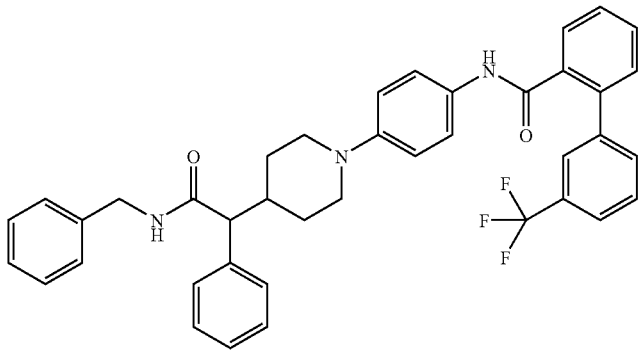
Co. No. 105; Ex. B.19
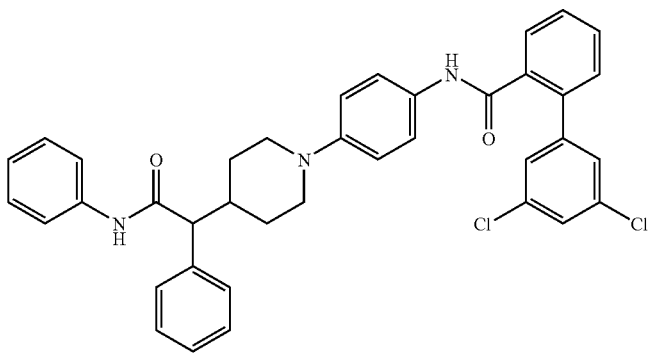
Co. No. 106; Ex. B.19
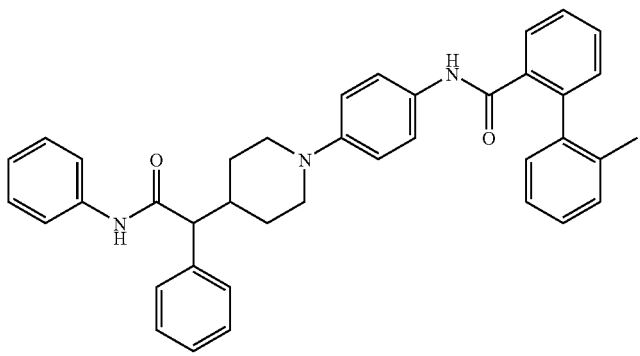
Co. No. 107; Ex. B.19
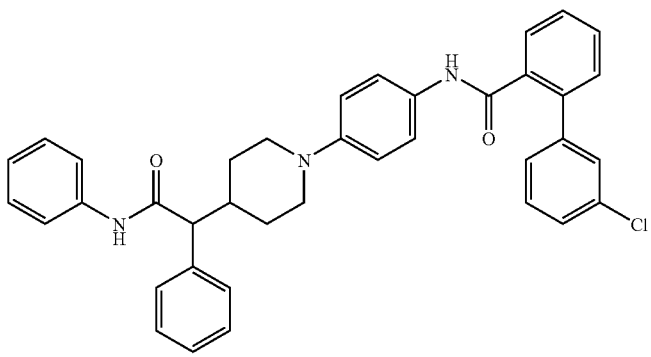
Co. No. 108; Ex. B.19

TABLE F-1-continued
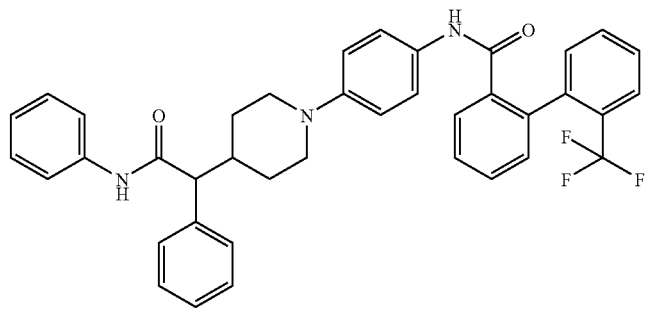
Co. No. 109; Ex. B.19
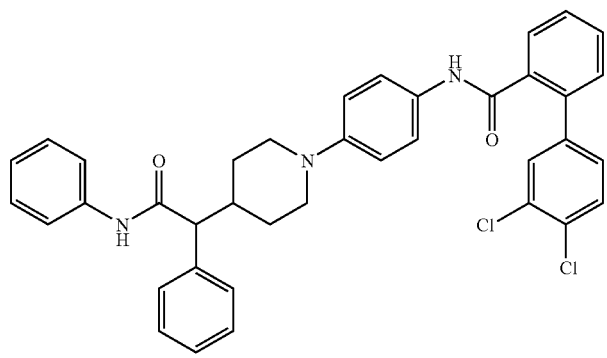
Co. No. 110; Ex. B.19
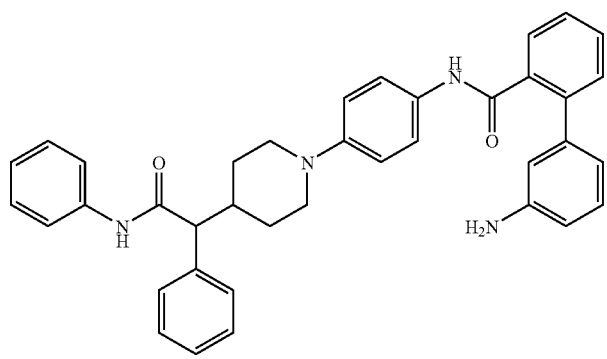
Co. No. 111; Ex. B.19
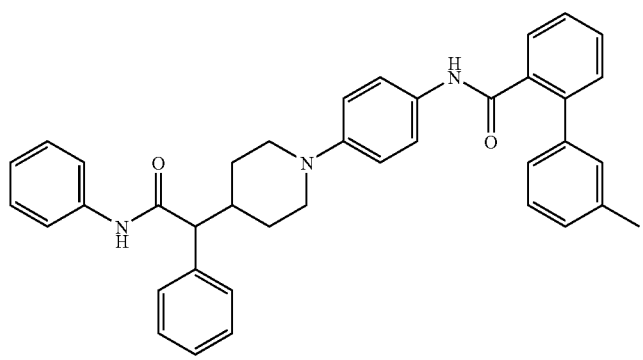
Co. No. 112; Ex. B.19

TABLE F-1-continued
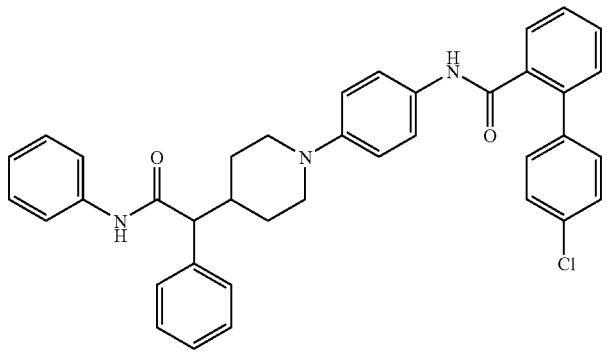
Co. No. 113; Ex. B.19
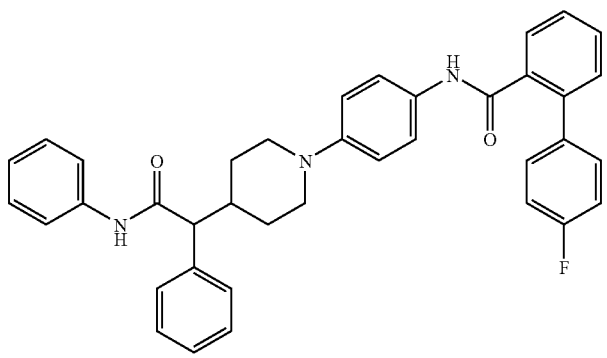
Co. No. 114; Ex. B.19
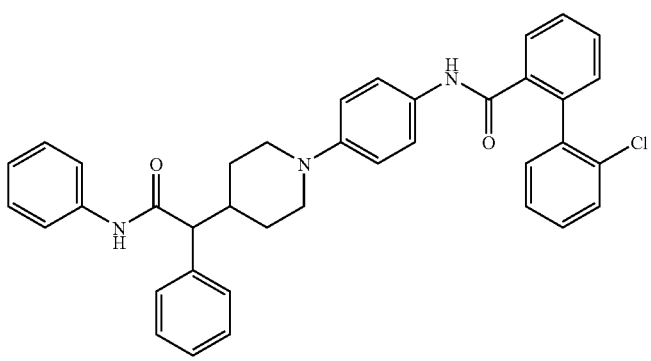
Co. No. 115; Ex. B.19
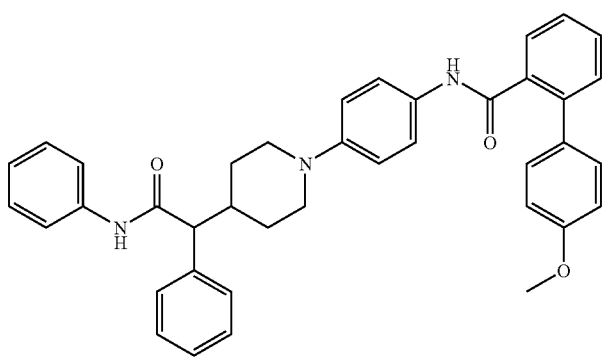
Co. No. 116; Ex. B.19

TABLE F-1-continued
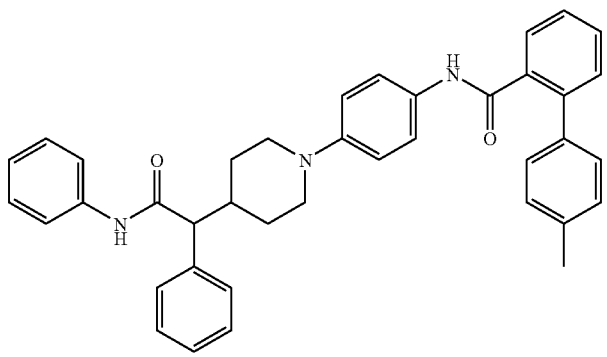
Co. No. 117; Ex. B.19
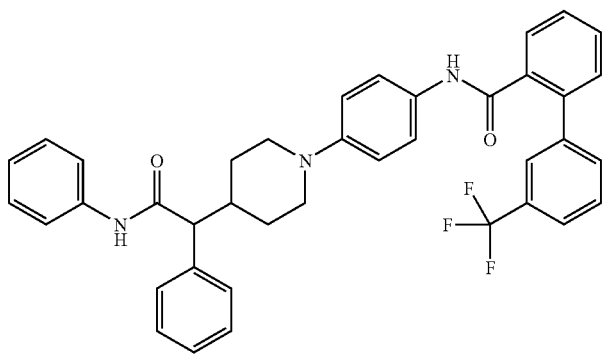
Co. No. 118; Ex. B.19
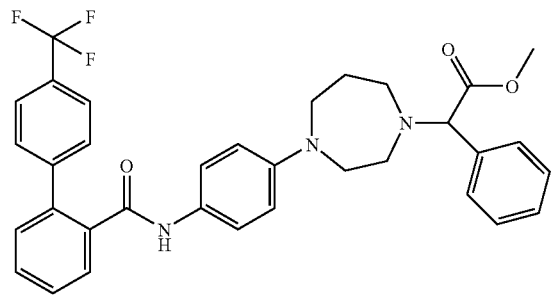
Co. No. 119; Ex. B.20
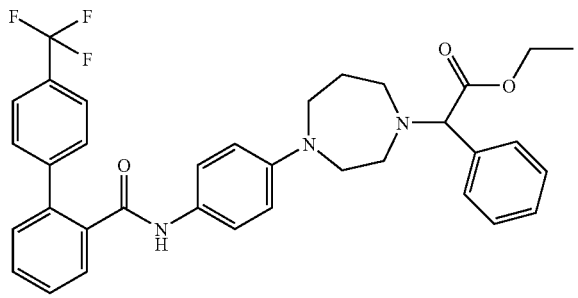
Co. No. 120; Ex. B.20

TABLE F-1-continued
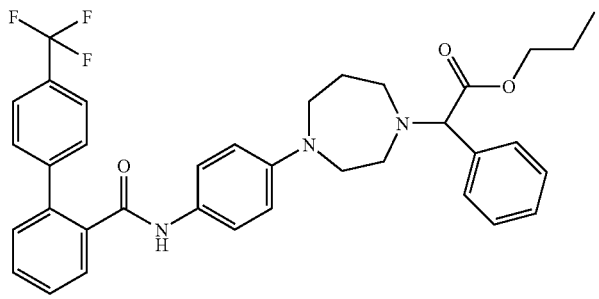
Co. No. 121; Ex. B.20
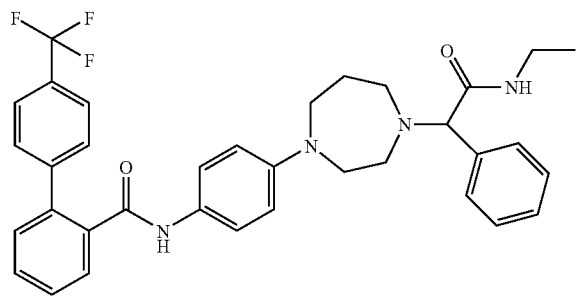
Co. No. 122; Ex. B.20
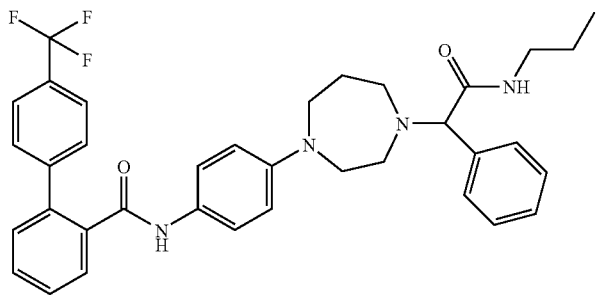
Co. No. 123; Ex. B.20
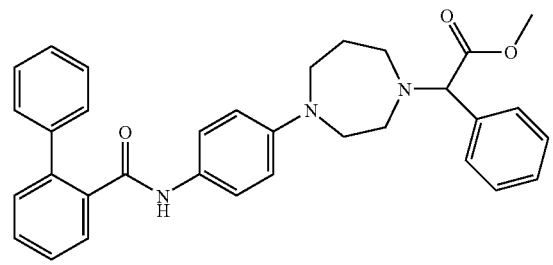
Co. No. 124; Ex. B.20
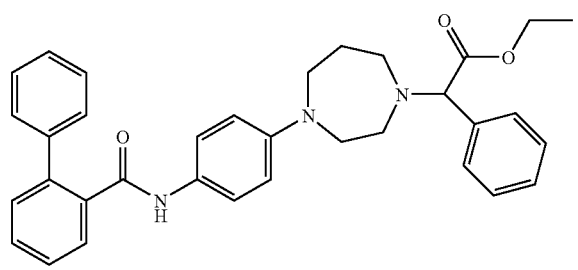

TABLE F-1-continued
Co. No. 125; Ex. B.20
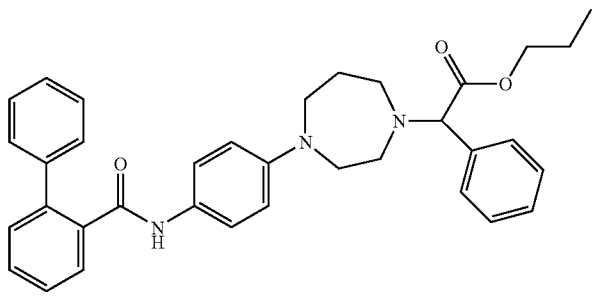
Co. No. 126; Ex. B.20
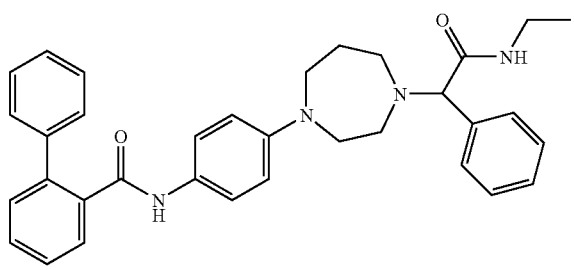
Co. No. 127; Ex. B.20
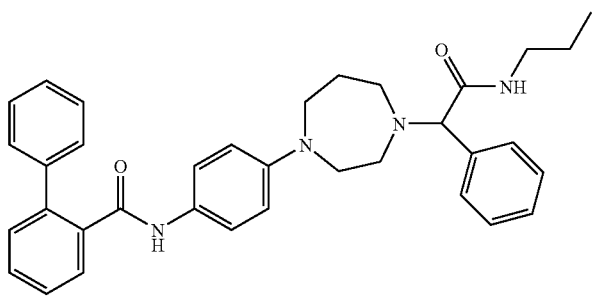
Co. No. 128; Ex. B.20
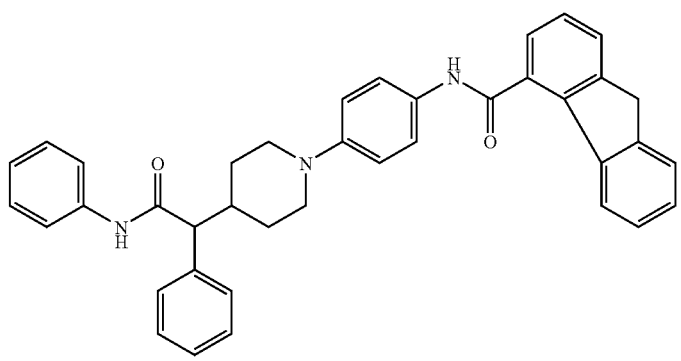
Co. No. 129; Ex. B.3

TABLE F-1-continued
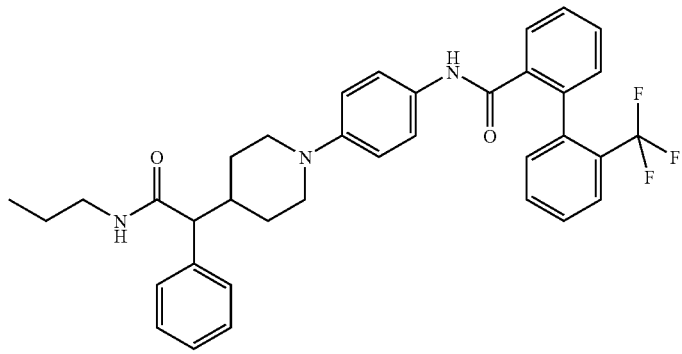
Co. No. 130; Ex. B.19
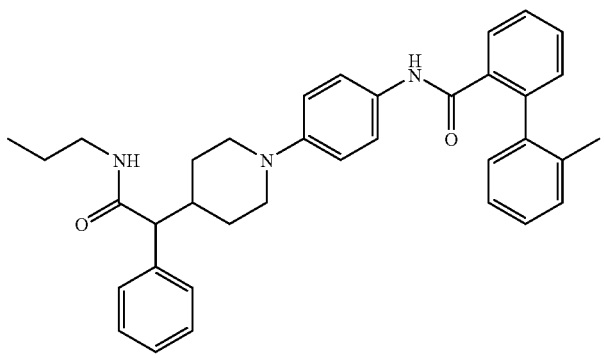
Co. No. 131; Ex. B.17
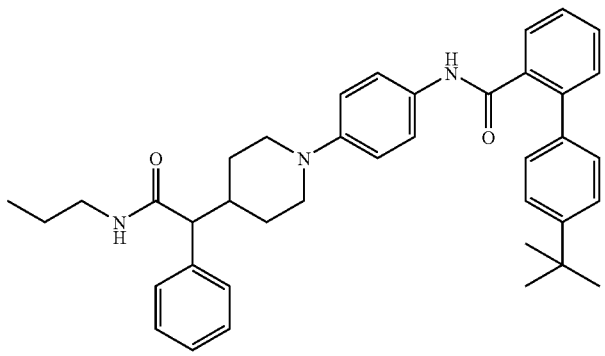
Co. No. 132; Ex. B.17
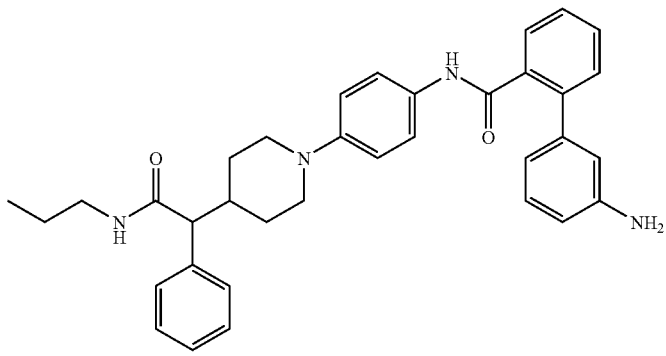
Co. No. 133; Ex. B.17

TABLE F-1-continued
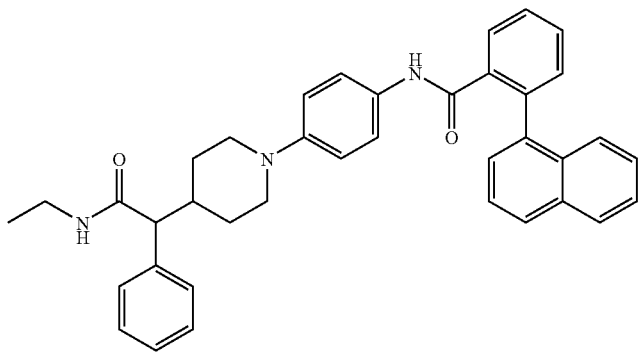
Co. No. 134; Ex. B.18
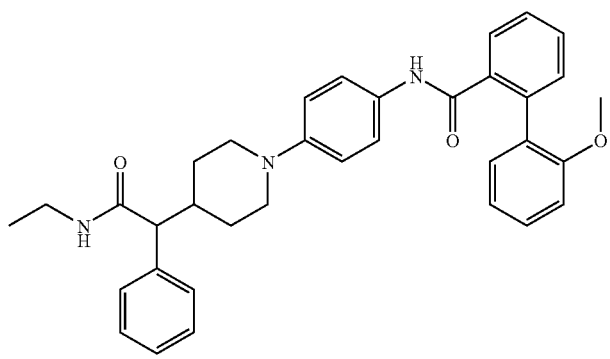
Co. No. 135; Ex. B.18
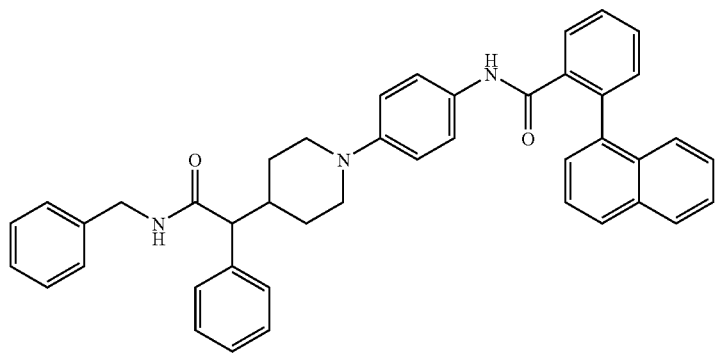
Co. No. 136; Ex. B.17
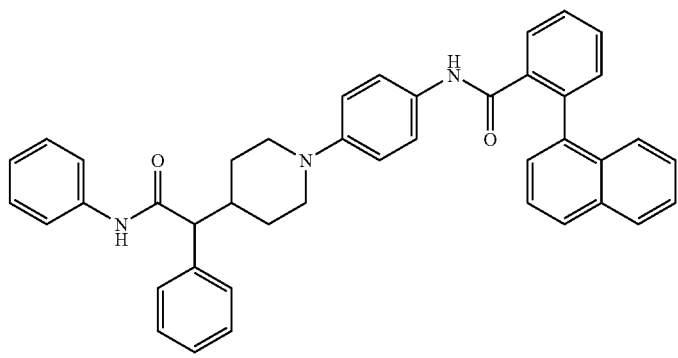
Co. No. 137; Ex. B.17

TABLE F-1-continued
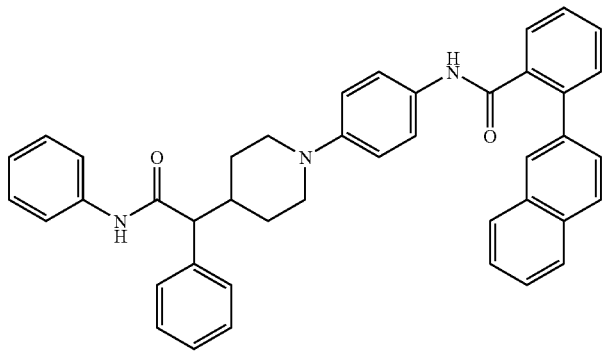
Co. No. 138; Ex. B.17
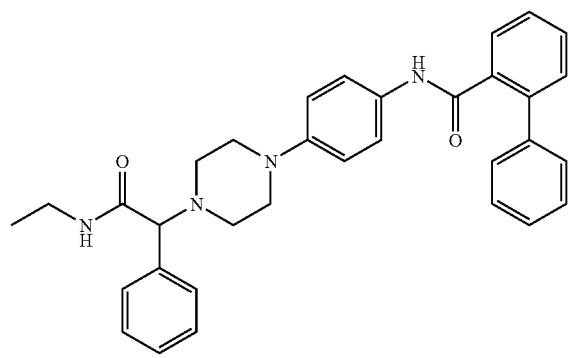
.CH₄O(1:1); Co. No. 139; Ex. B.9;
mp. 152° C.
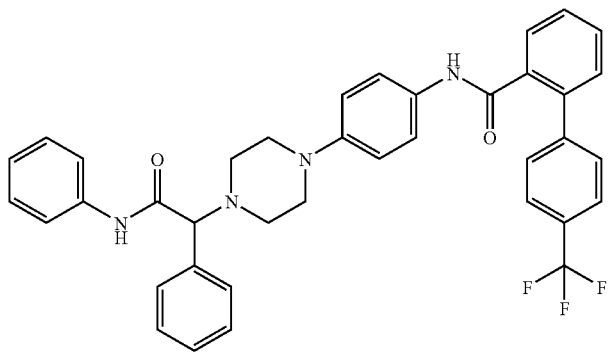
Co. No. 140; Ex. B.9; mp. 231° C.
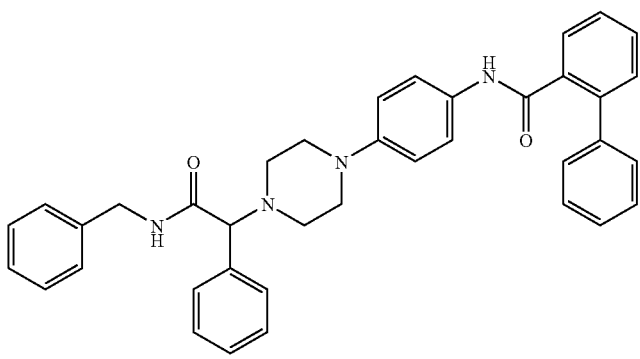
Co. No. 141; Ex. B.9

TABLE F-1-continued
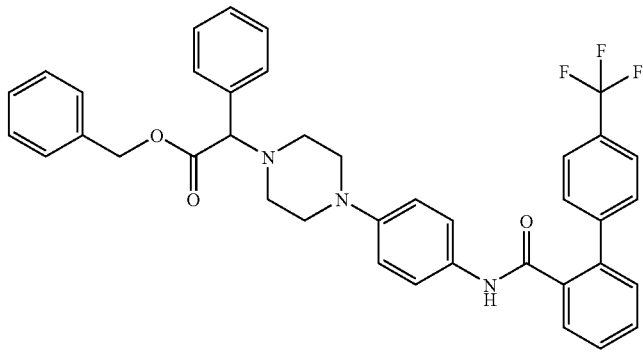
Co. No. 142; Ex. B.9
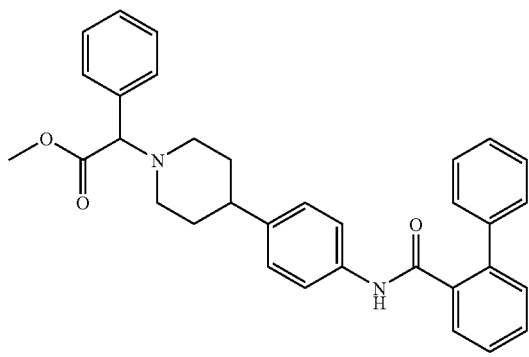
Co. No. 143; Ex. B.9
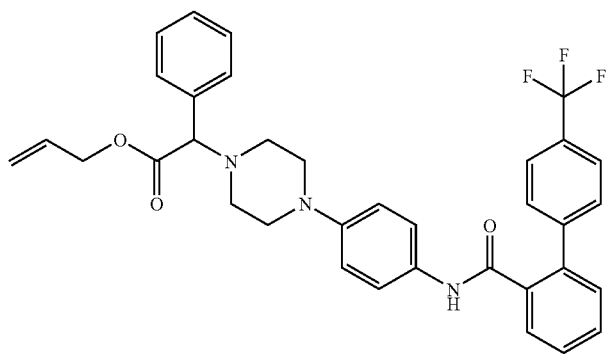
Co. No. 144; Ex. B.9; mp. 138° C.
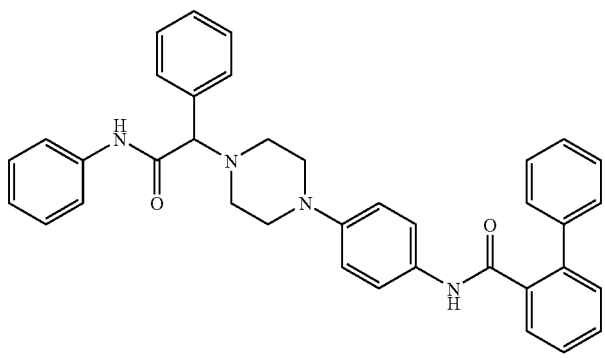
Co. No. 145; Ex. B.9; mp. 217° C.

TABLE F-1-continued
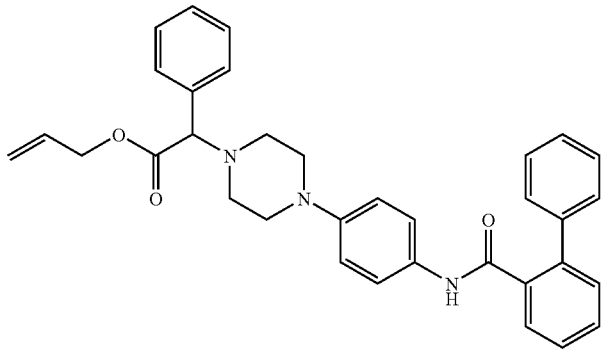
Co. No. 146; Ex. B.9; mp. 136° C.
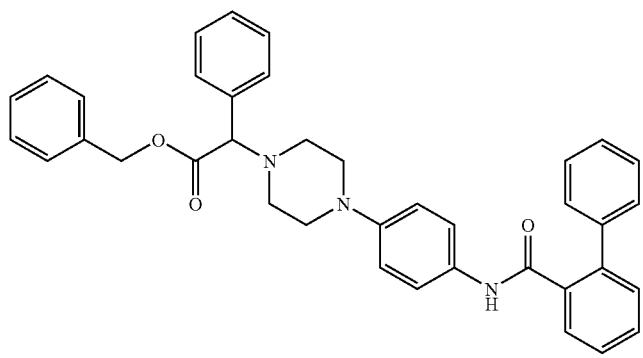
Co. No. 147; Ex. B.9; mp. 132° C.
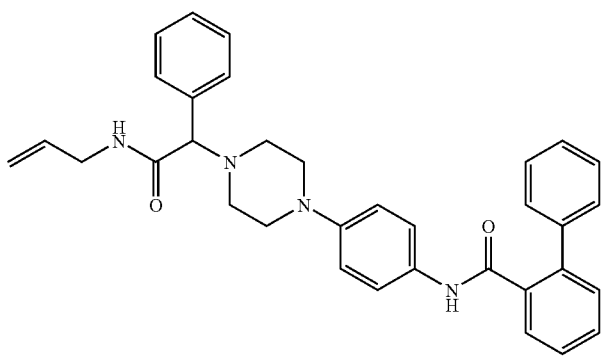
.C$_3$H$_8$O(1:1); Co. No. 148; Ex. B.9
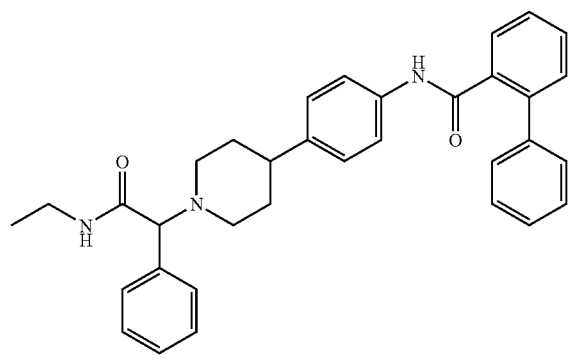
Co. No. 149; Ex. B.9; mp. 125° C.

TABLE F-1-continued
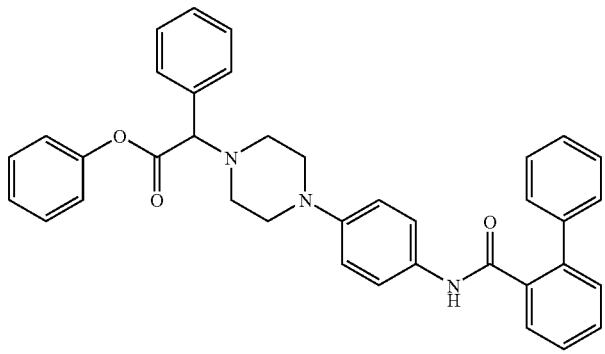
.HCl(1:2); Co. No. 150; Ex. B.9;
mp. 151° C.
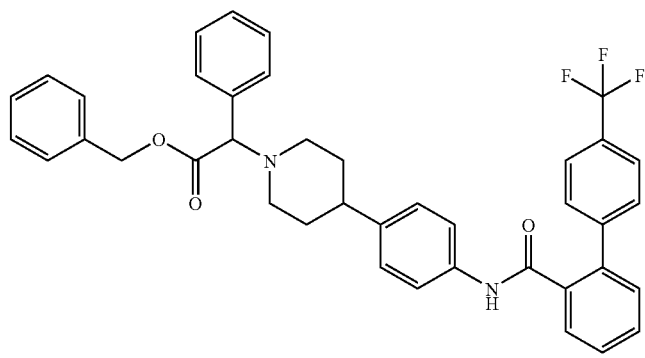
Co. No. 151; Ex. B.9
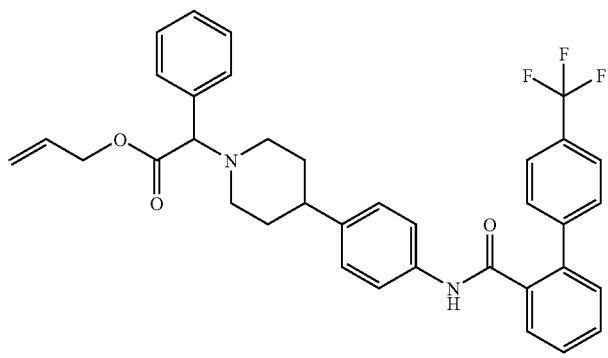
Co. No. 152; Ex. B.9
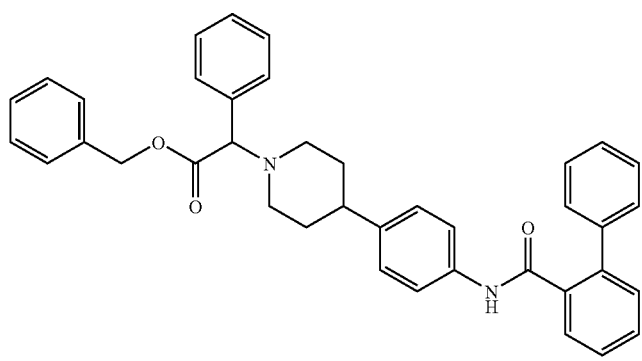
Co. No. 153; Ex. B.9

TABLE F-1-continued
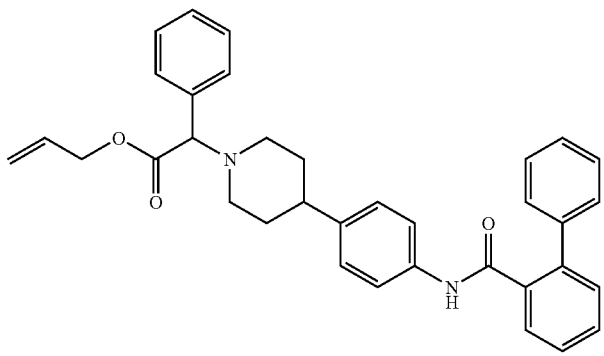
Co. No. 154; Ex. B.9
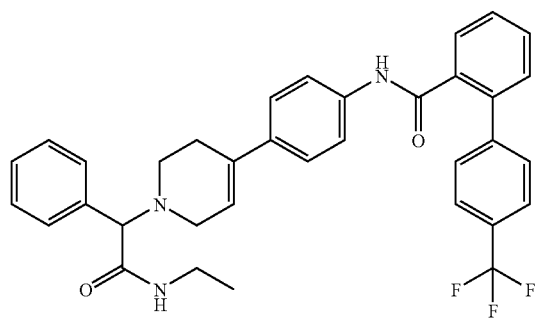
Co. No. 155; Ex. B.9
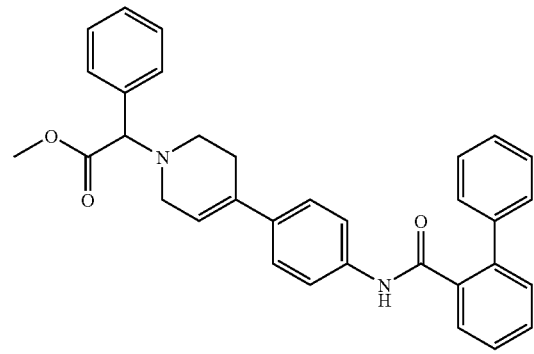
Co. No. 156; Ex. B.9
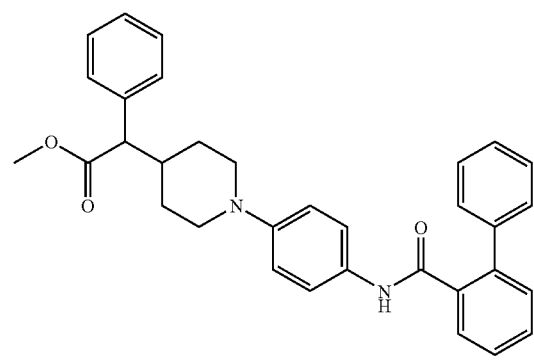
Co. No. 157; Ex. B.8; mp. 174° C.

TABLE F-1-continued
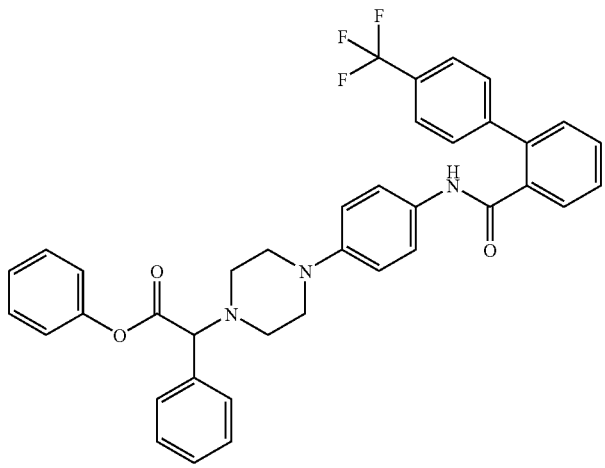
.HCl(1:2).H₂O(1:1); Co. No. 158; Ex. B.9
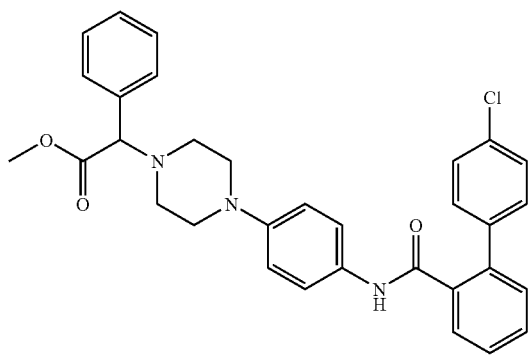
Co. No. 159; Ex. B.22
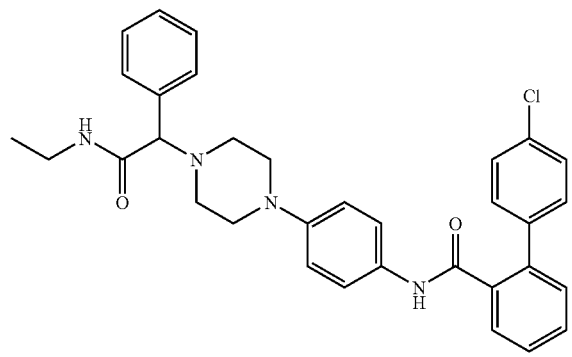
Co. No. 160; Ex. B.22

TABLE F-1-continued
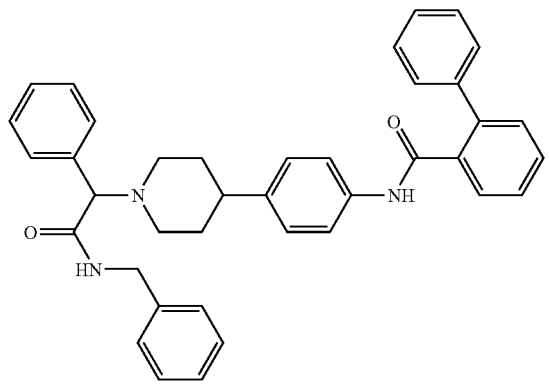
Co. No. 161; Ex. B.9
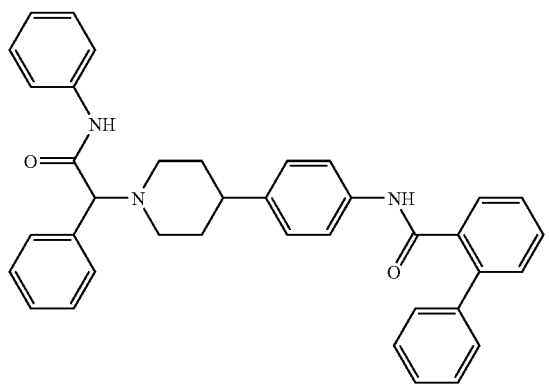
Co. No. 162; Ex. B.9
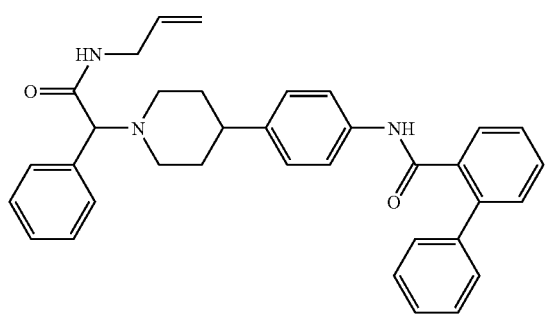
Co. No. 163; Ex. B.9

TABLE F-1-continued
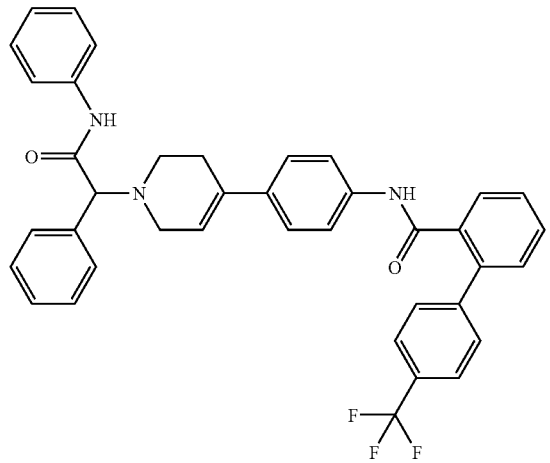
Co. No. 164; Ex. B.9
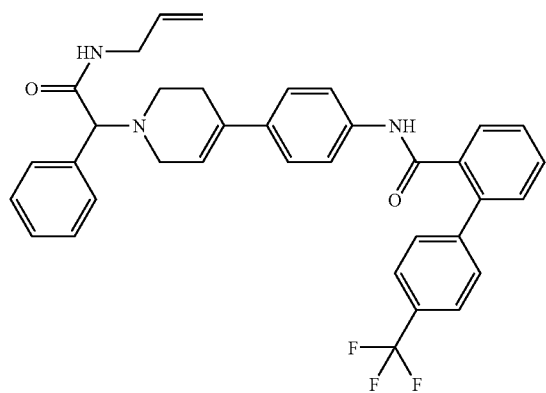
Co. No. 165; Ex. B.9
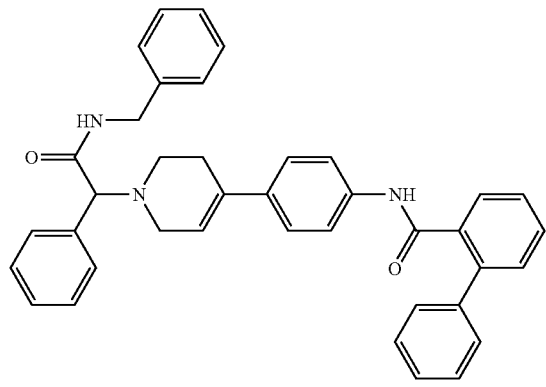
Co. No. 166; Ex. B.9

TABLE F-1-continued
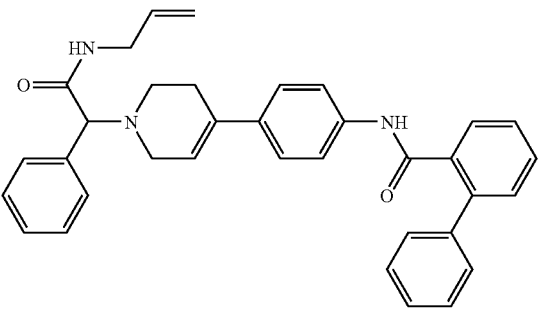
Co. No. 167; Ex. B.9
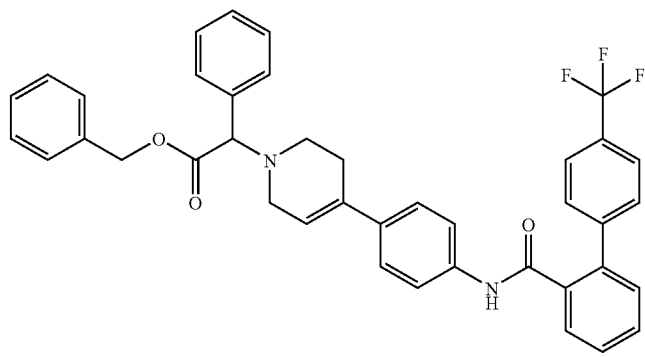
Co. No. 168; Ex. B.9
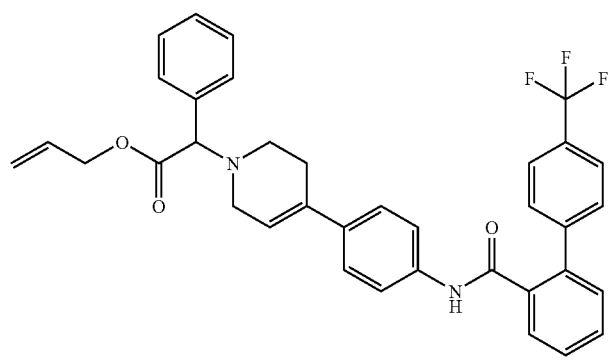
Co. No. 169; Ex. B.9
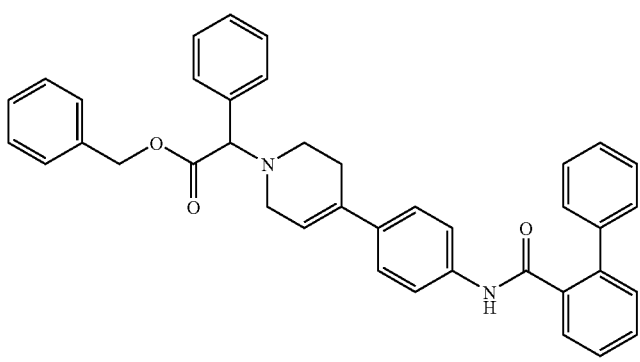
Co. No. 170; Ex. B.9

TABLE F-1-continued
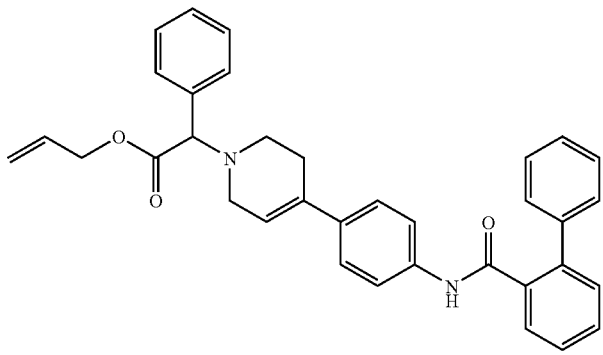
Co. No. 171; Ex. B.9
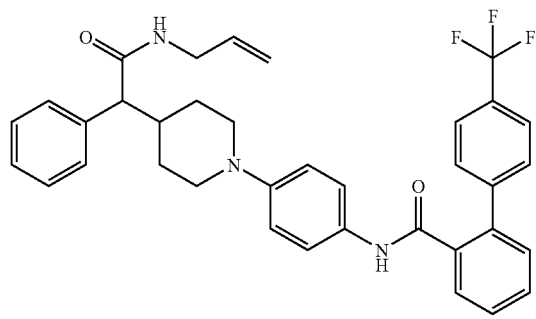
Co. No. 172; Ex. B.12
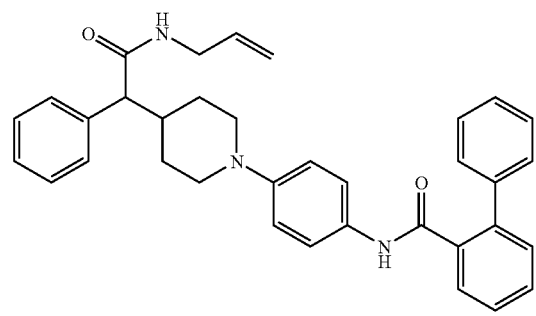
Co. No. 173; Ex. B.12
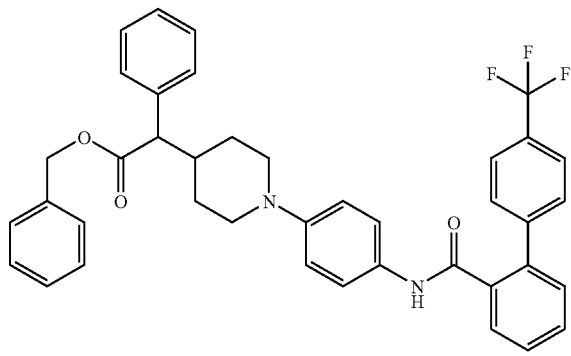
Co. No. 174; Ex. B.12

TABLE F-1-continued
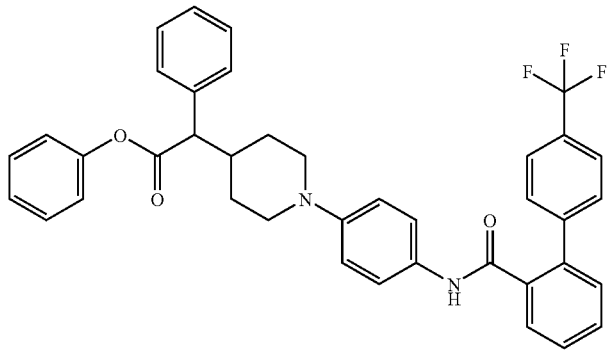
Co. No. 175; Ex. B.12
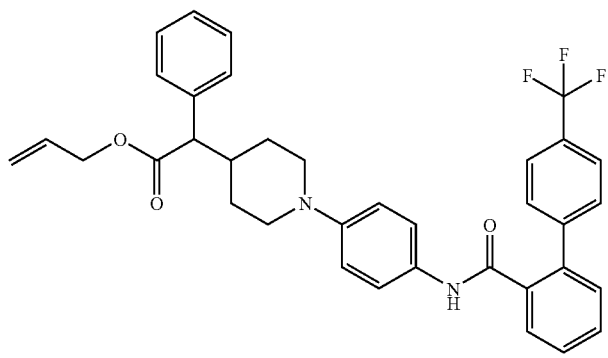
Co. No. 176; Ex. B.12
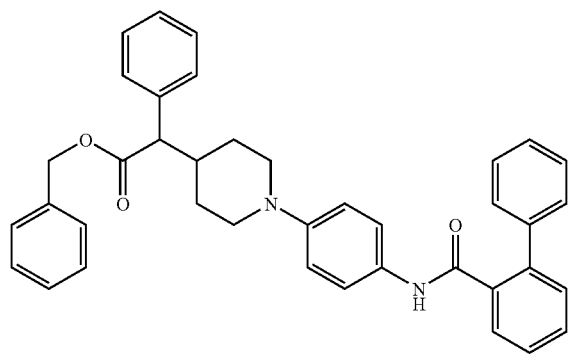
Co. No. 177; Ex. B.12
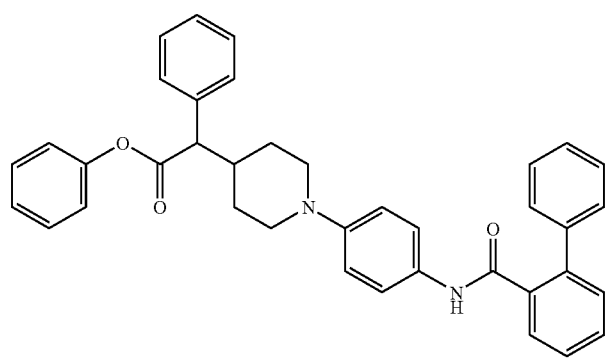
Co. No. 178; Ex. B.12

TABLE F-1-continued
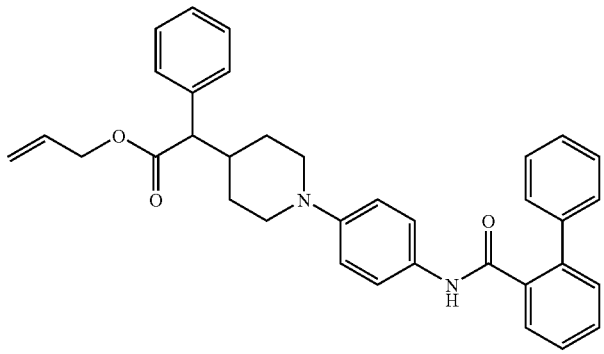
Co. No. 179; Ex. B.12
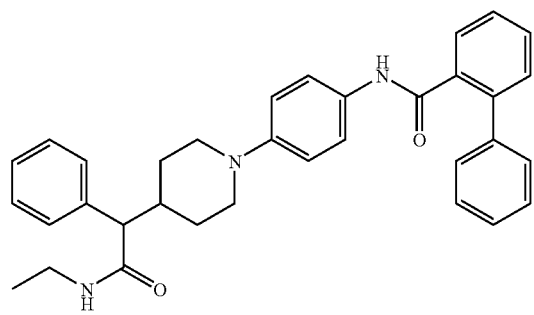
Co. No. 180; Ex. B.16; mp. 192° C.
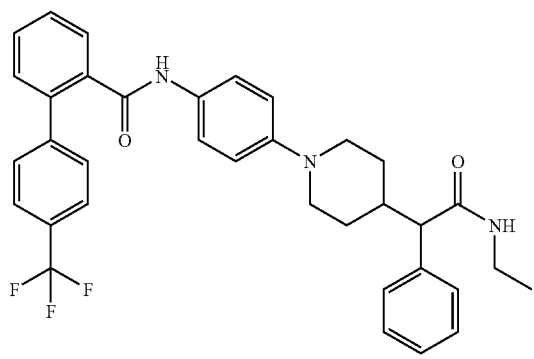
Co. No. 181; Ex. B.16; mp. 142° C.
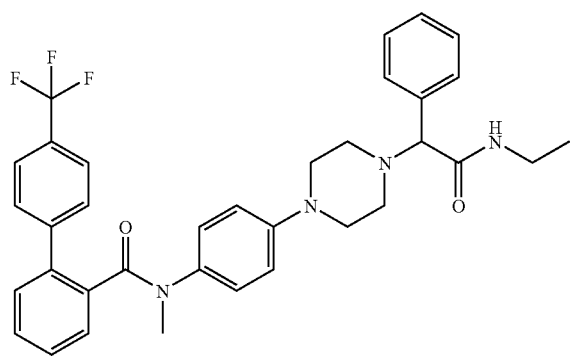
.HCl(1:1); Co. No. 182; Ex. B.9

TABLE F-1-continued
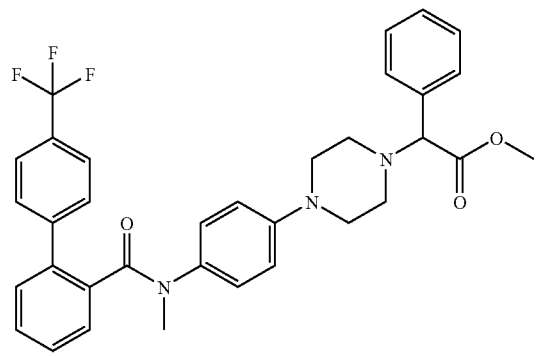
.HCl(1:1); Co. No. 183; Ex. B.9
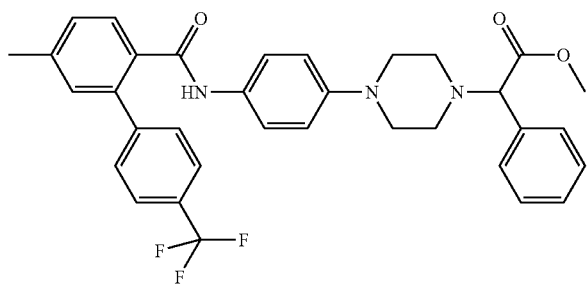
Co. No. 184; Ex. B.22
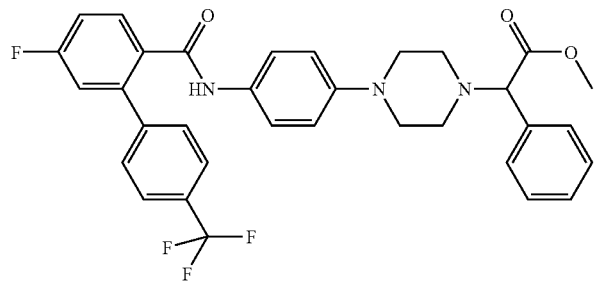
Co. No. 185; Ex. B.22
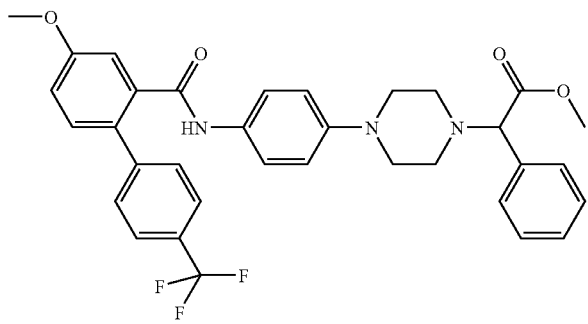
Co. No. 186; Ex. B.22

TABLE F-1-continued
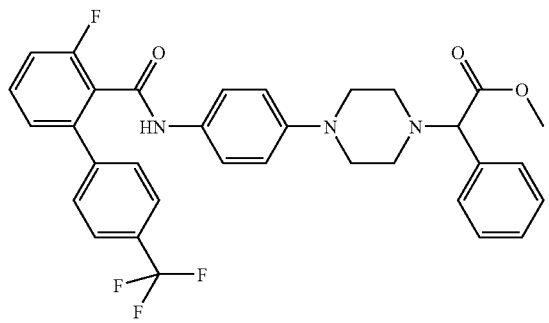
Co. No. 187; Ex. B.22
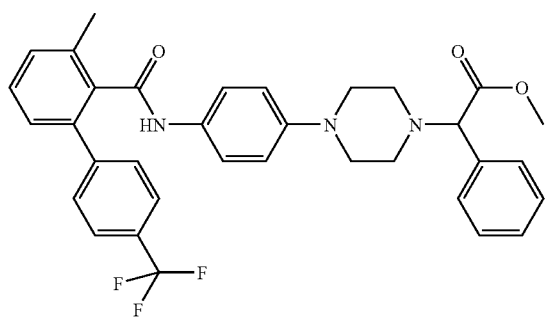
Co. No. 188; Ex. B.22
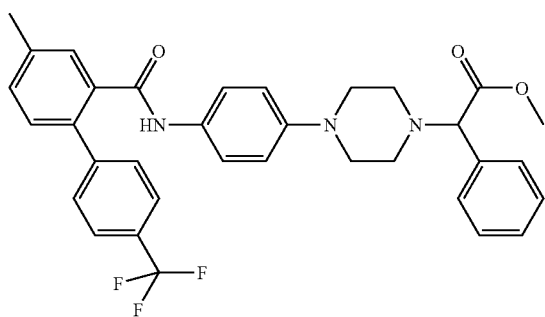
Co. No. 189; Ex. B.22
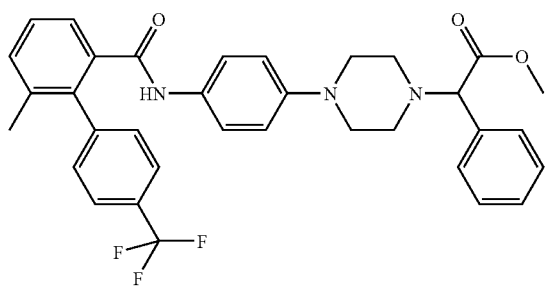
Co. No. 190; Ex. B.22

TABLE F-1-continued
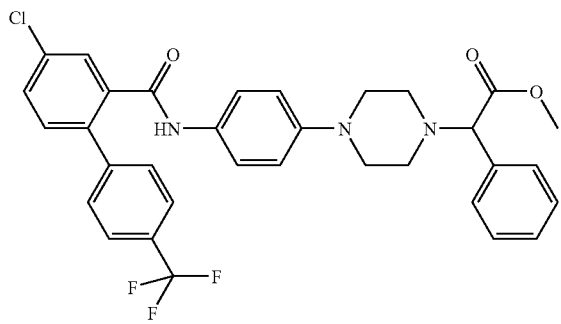
Co. No. 191; Ex. B.22
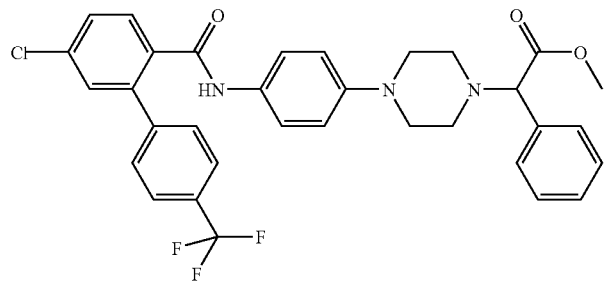
Co. No. 192; Ex. B.22
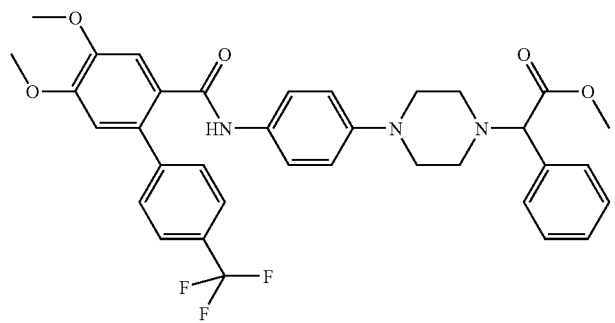
Co. No. 193; Ex. B.22
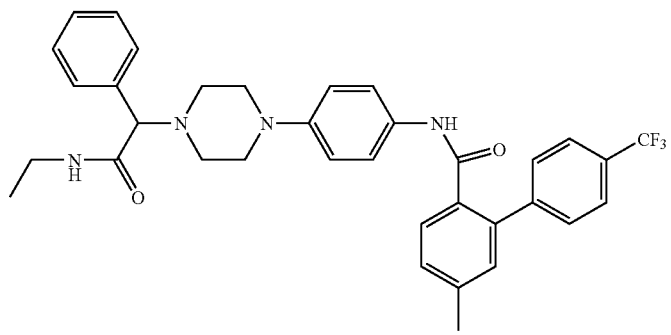
Co. No. 194; Ex. B.22

TABLE F-1-continued
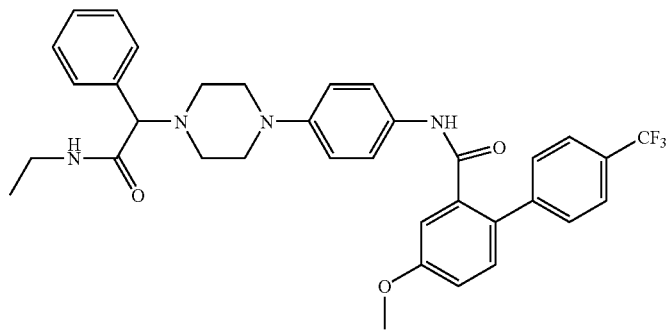
Co. No. 195; Ex. B.22
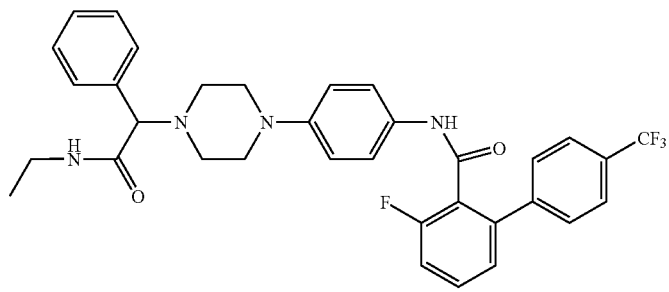
Co. No. 196; Ex. B.22
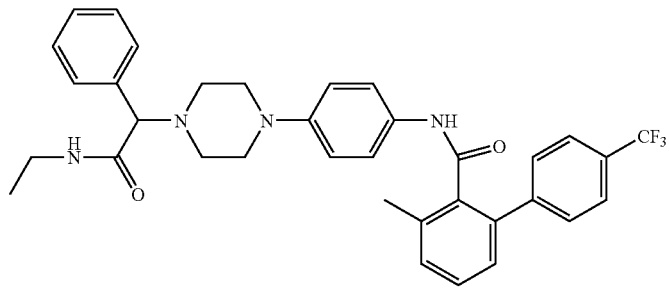
Co. No. 197; Ex. B.22
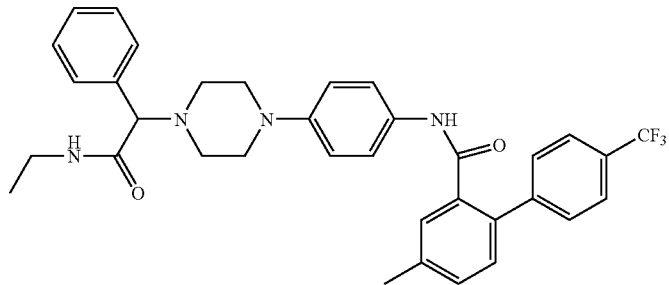
Co. No. 198; Ex. B.22

TABLE F-1-continued
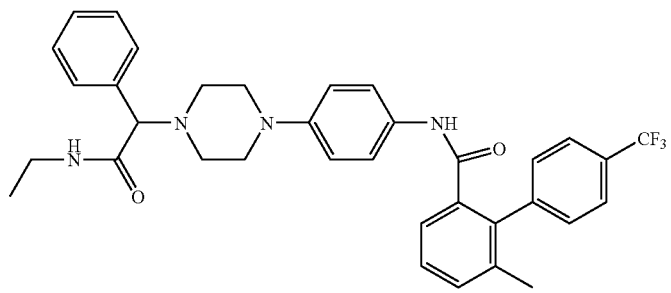
Co. No. 199; Ex. B.22
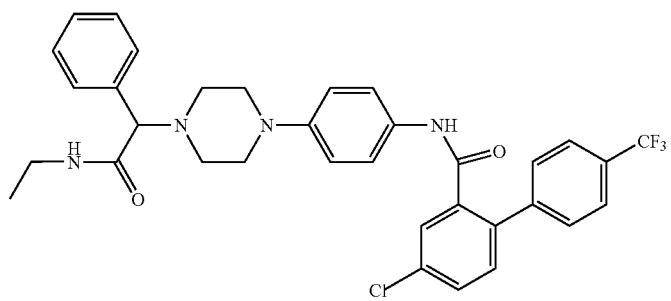
Co. No. 200; Ex. B.22
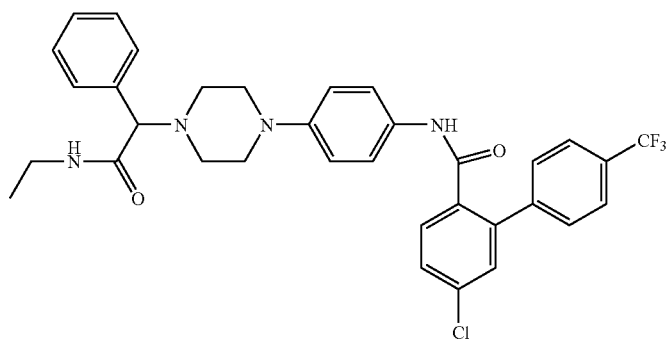
Co. No. 201; Ex. B.22
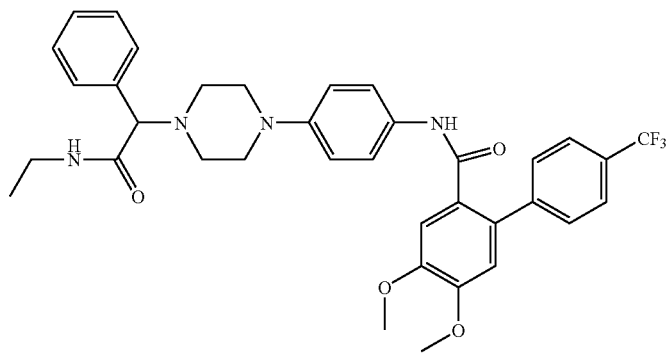
Co. No. 202; Ex. B.22

TABLE F-1-continued
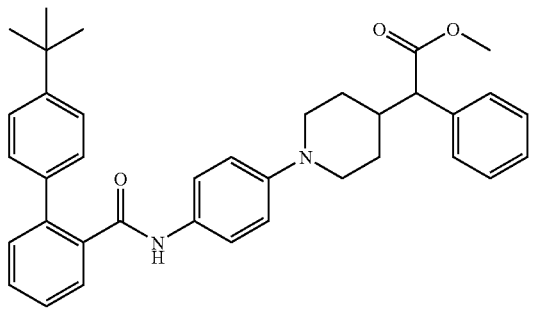
.HCl(1:1).C₃H₈O(1:1); Co. No. 203;
Ex. B.8
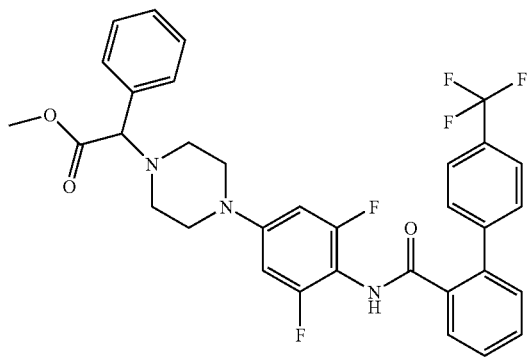
Co. No. 204; Ex. B.22
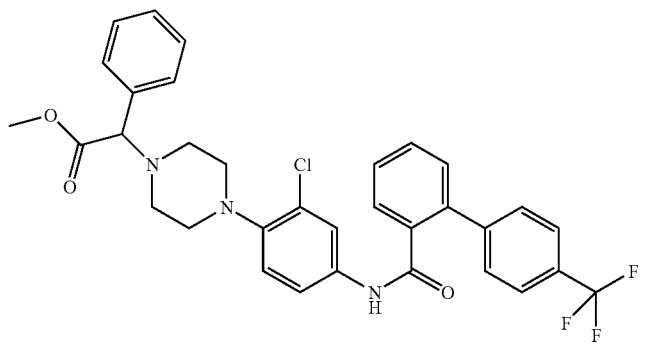
Co. No. 205; Ex. B.22
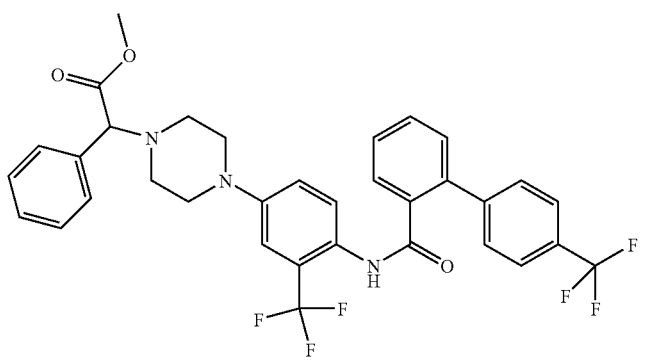
Co. No. 206; Ex. B.22

TABLE F-1-continued
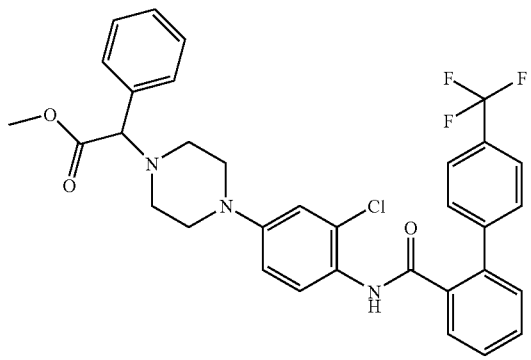
Co. No. 207; Ex. B.22
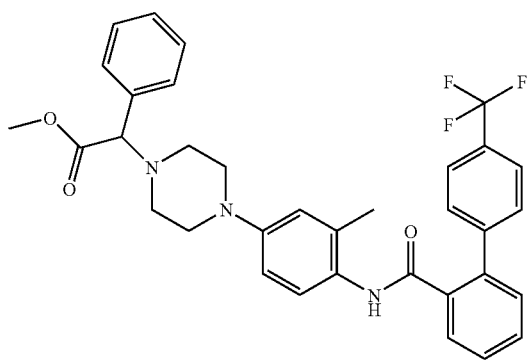
Co. No. 208; Ex. B.22
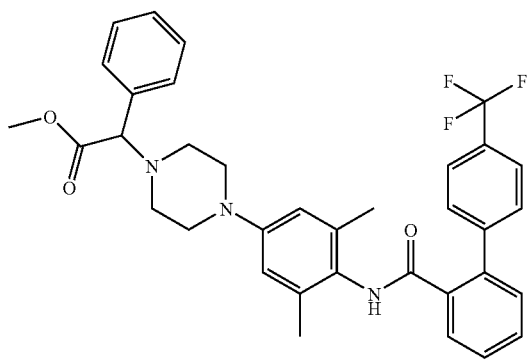
Co. No. 209; Ex. B.22
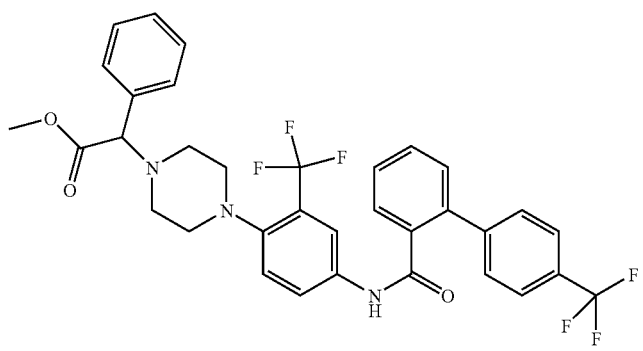
Co. No. 210; Ex. B.22

TABLE F-1-continued
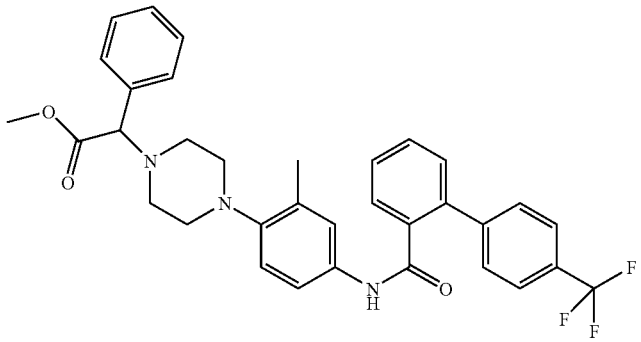
Co. No. 211; Ex. B.22
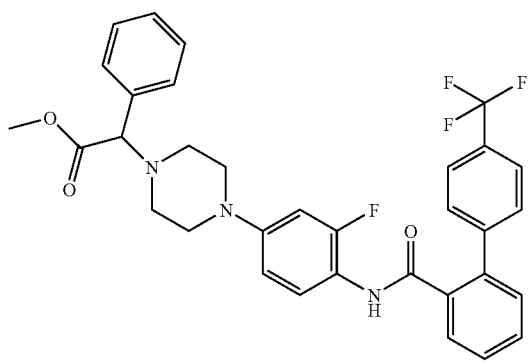
Co. No. 212; Ex. B.22
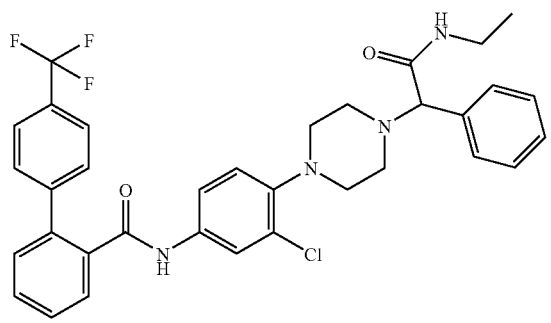
Co. No. 213; Ex. B.22
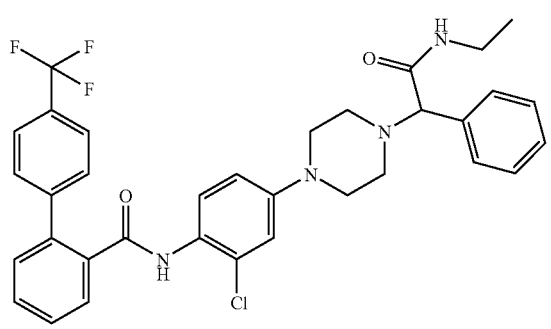
Co. No. 214; Ex. B.22

TABLE F-1-continued
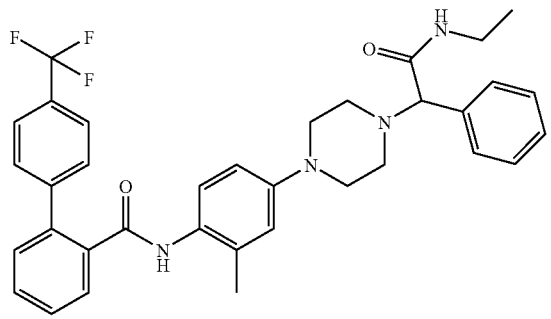
Co. No. 215; Ex. B.22
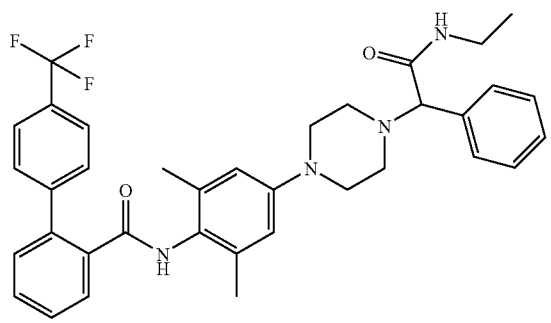
Co. No. 216; Ex. B.22
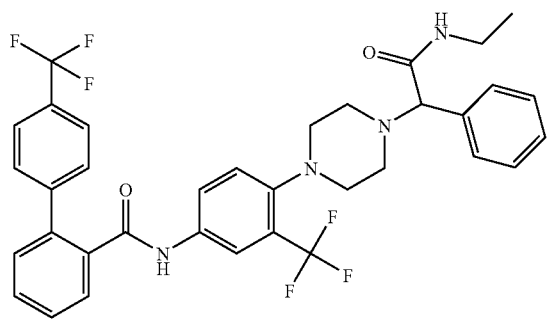
Co. No. 217; Ex. B.22
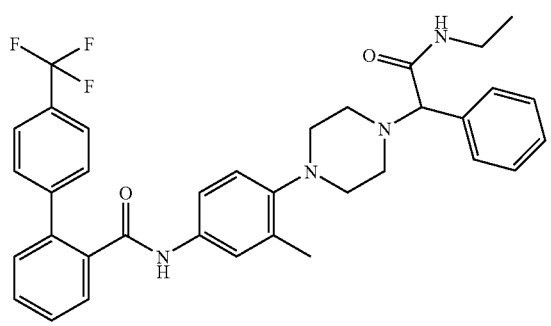
Co. No. 218; Ex. B.22

TABLE F-1-continued
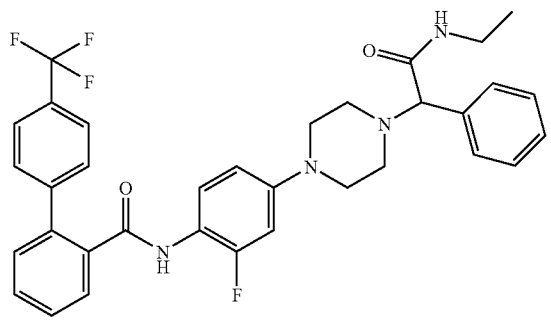
Co. No. 219; Ex. B.22
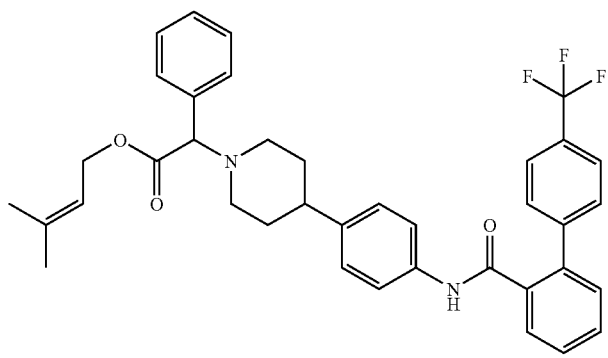
Co. No. 220; Ex. B.23
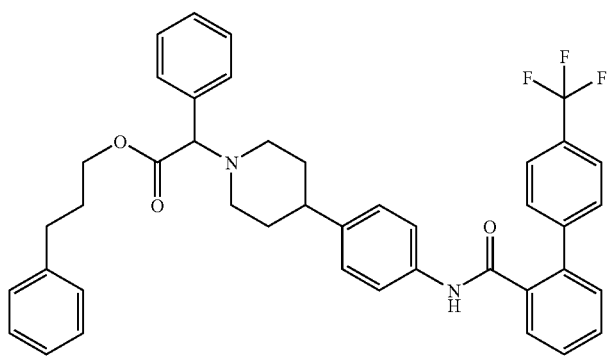
Co. No. 221; Ex. B.23
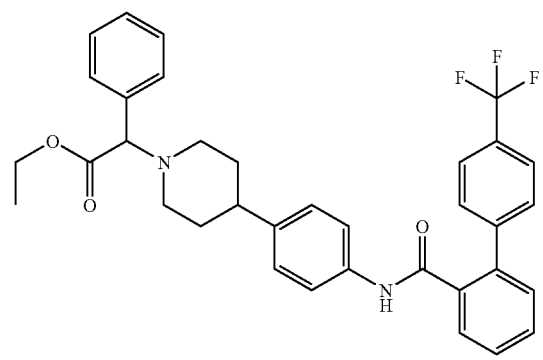
Co. No. 222; Ex. B.24

TABLE F-1-continued
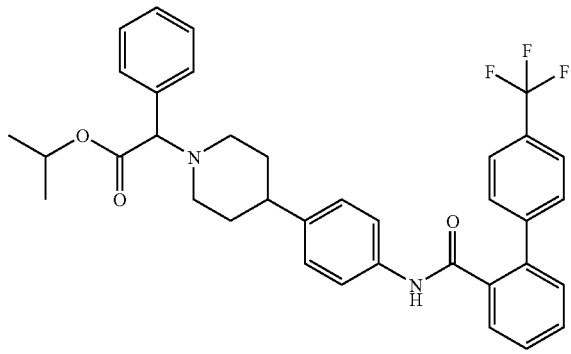
Co. No. 223; Ex. B.24
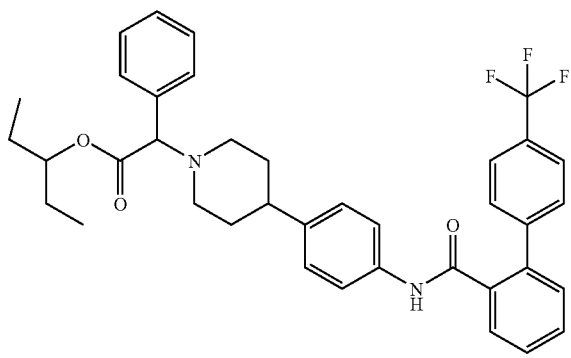
Co. No. 224; Ex. B.24
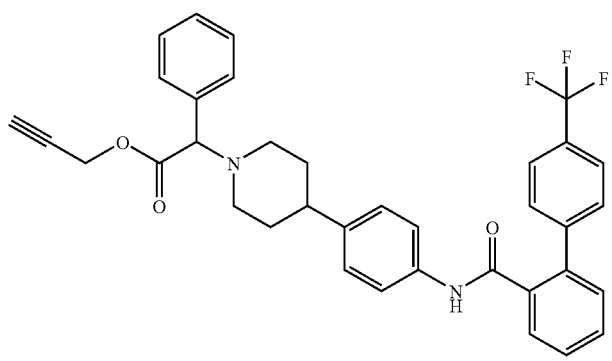
Co. No. 225; Ex. B.24
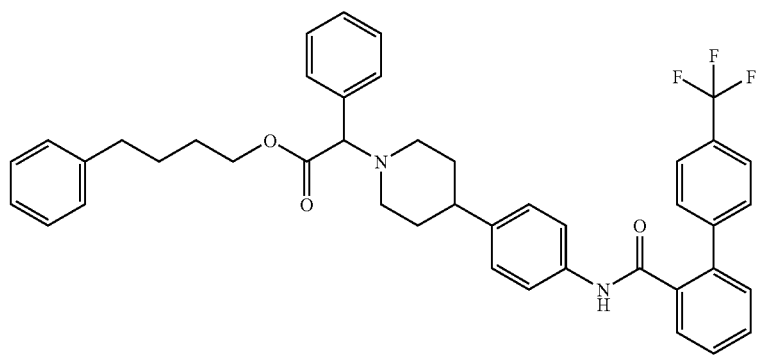
Co. No. 226; Ex. B.24

TABLE F-1-continued
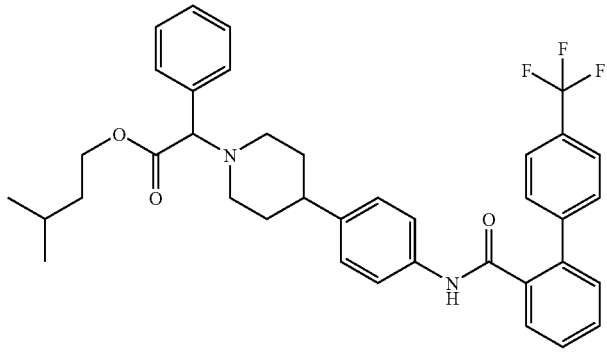
Co. No. 227; Ex. B.24
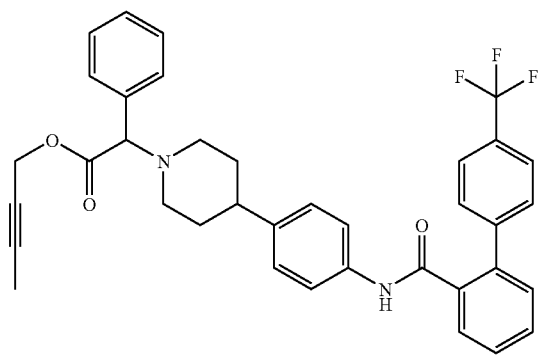
Co. No. 228; Ex. B.24
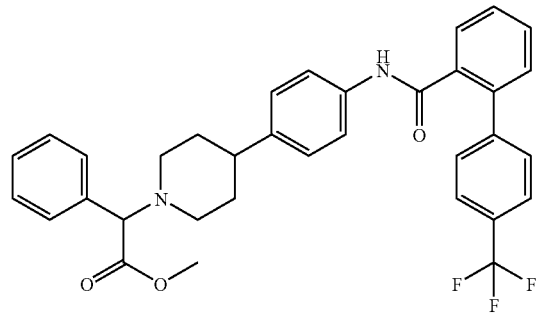
(−); Co. No. 229; Ex. B.21; mp. 158° C.;
$[\alpha]_D^{20} = -28.86°$ (c = 24.95 mg/5 ml in CH$_3$OH)
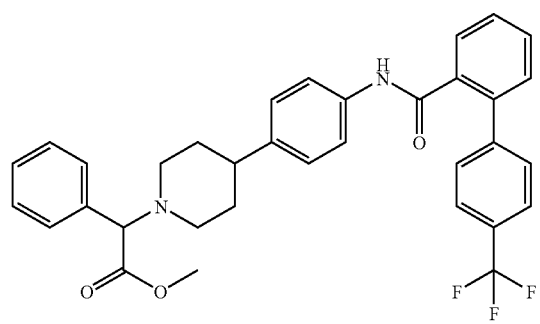
(+); Co. No. 230; Ex. B.21; mp. 160° C.;
$[\alpha]_D^{20} = +27.69°$ (c = 24.38 mg/5 ml in CH$_3$OH)

TABLE F-1-continued
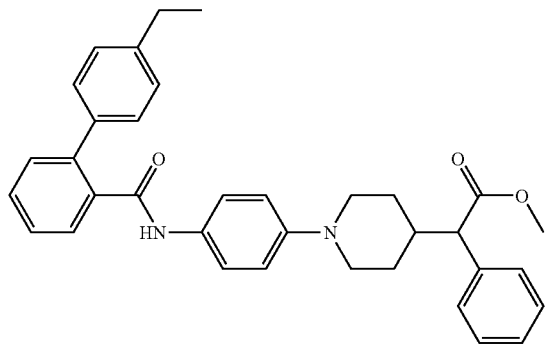
Co. No. 231; Ex. B.17
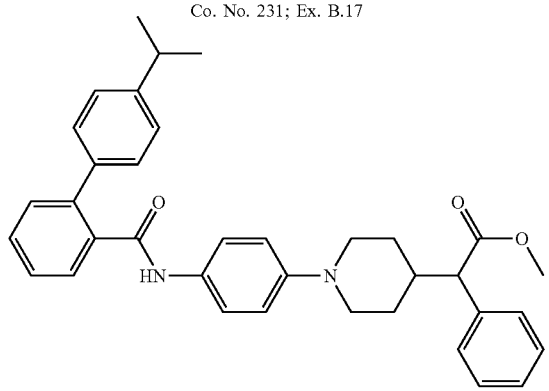
Co. No. 232; Ex. B.17
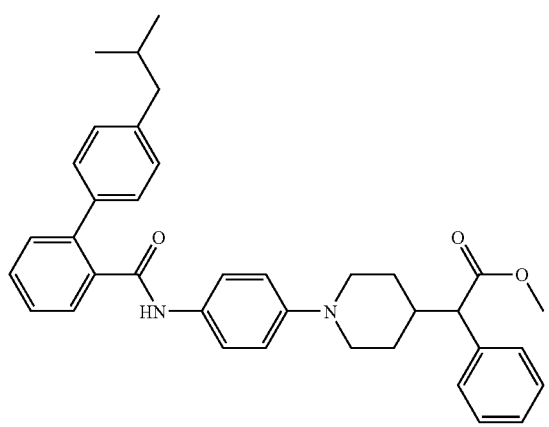
Co. No. 233; Ex. B.17
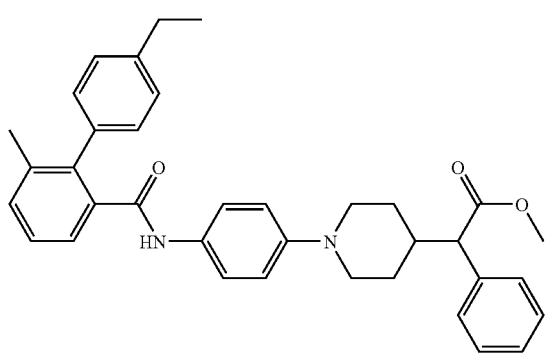
Co. No. 234; Ex. B.17

TABLE F-1-continued
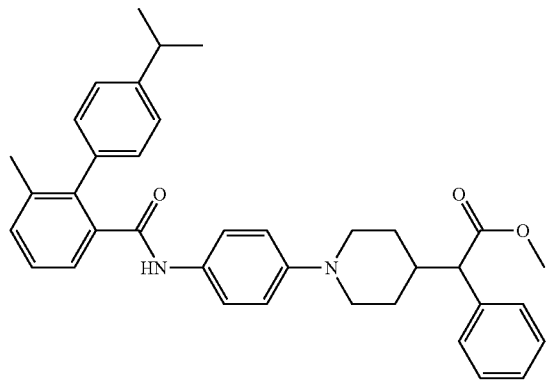
Co. No. 235; Ex. B.17
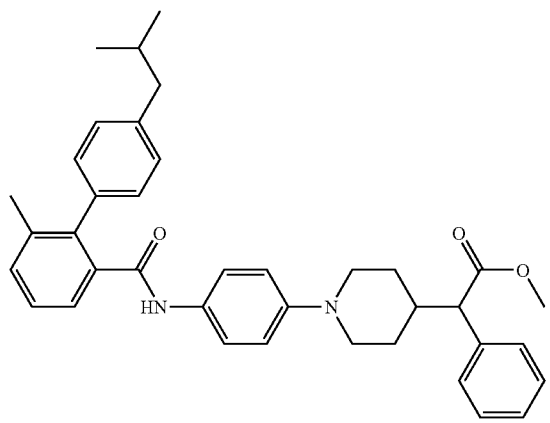
Co. No. 236; Ex. B.17
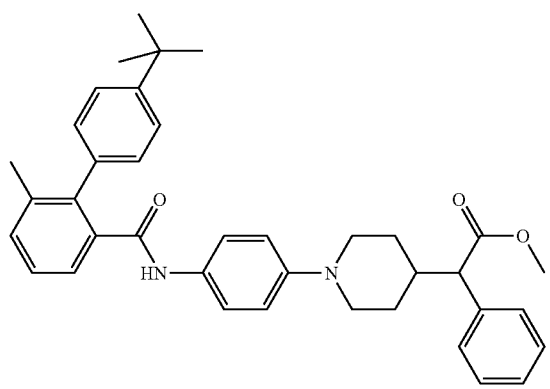
Co. No. 237; Ex. B.17

TABLE F-1-continued
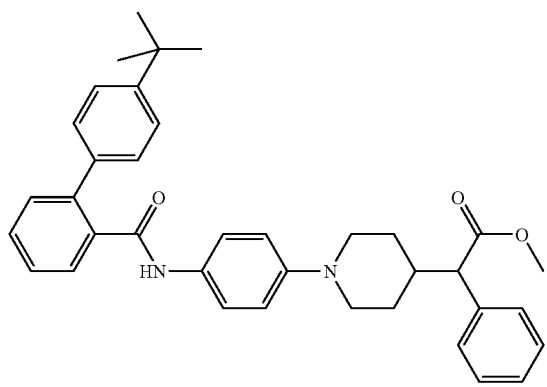
Co. No. 238; Ex. B.17
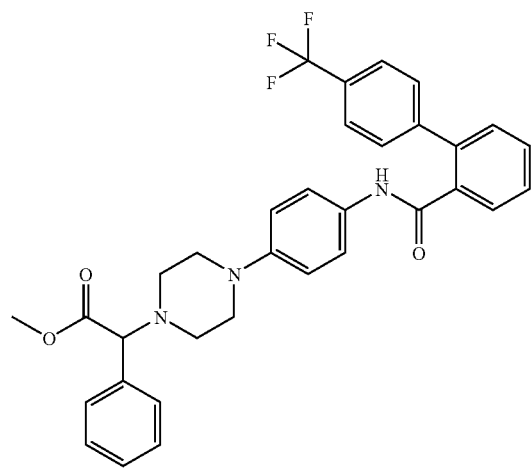
(A); CO. No. 239; Ex. B.9
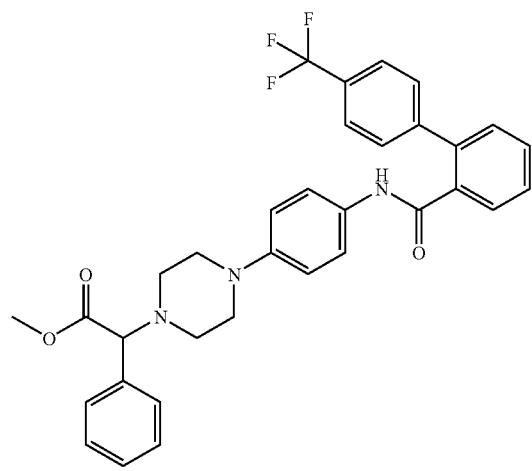
(B); Co. No. 240; Ex. B.9

TABLE F-1-continued
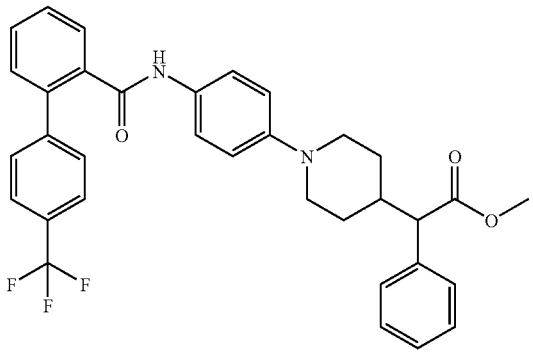
(A); Co. No. 241; Ex. B.8
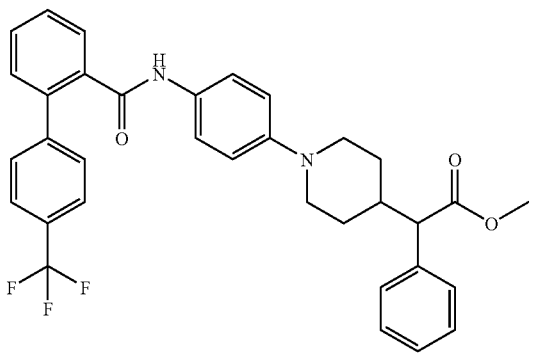
(B); Co. No. 242; Ex. B.8
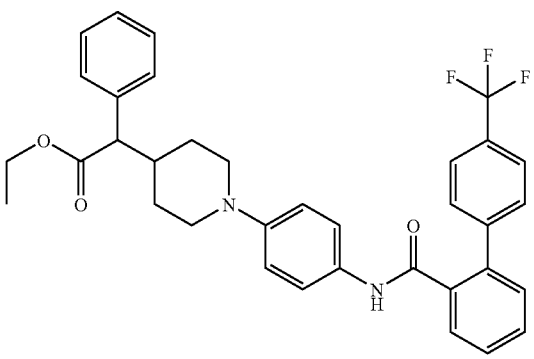
Co. No. 243; Ex. B.25
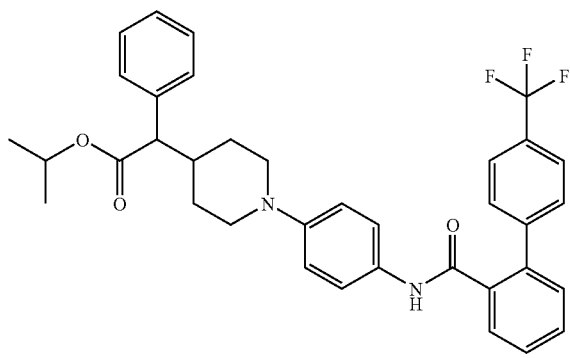
Co. No. 244; Ex. B.25

TABLE F-1-continued
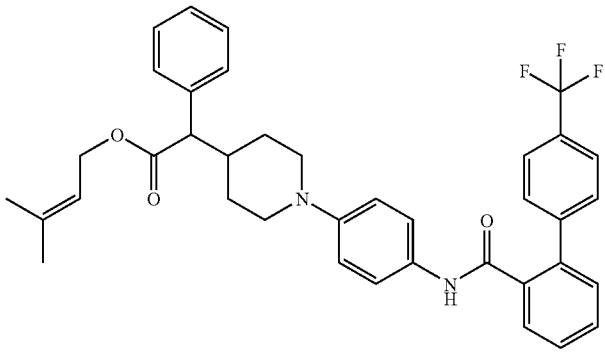
Co. No. 245; Ex. B.25
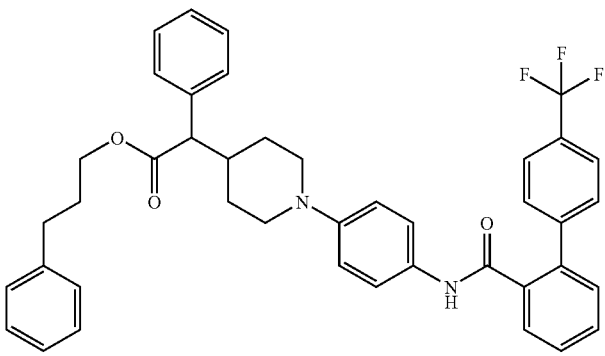
Co. No. 246; Ex. B.25
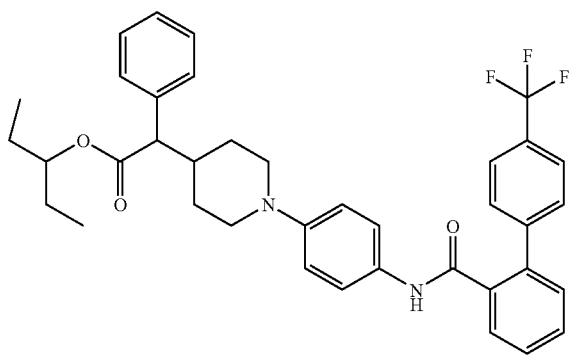
Co. No. 247; Ex. B.25
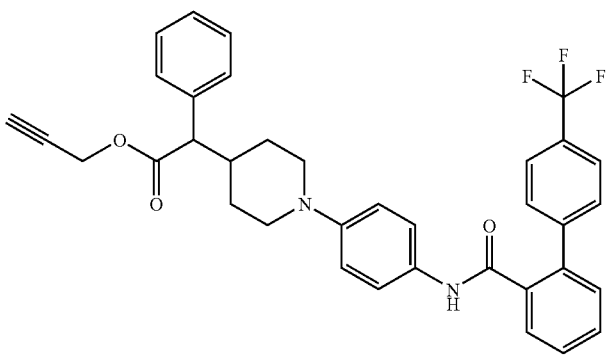
Co. No. 248; Ex. B.25

TABLE F-1-continued
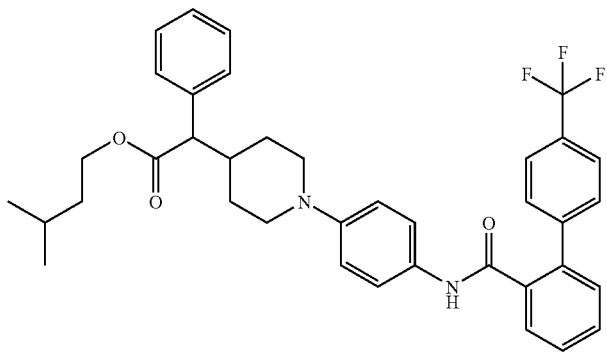
Co. No. 249; Ex. B.25
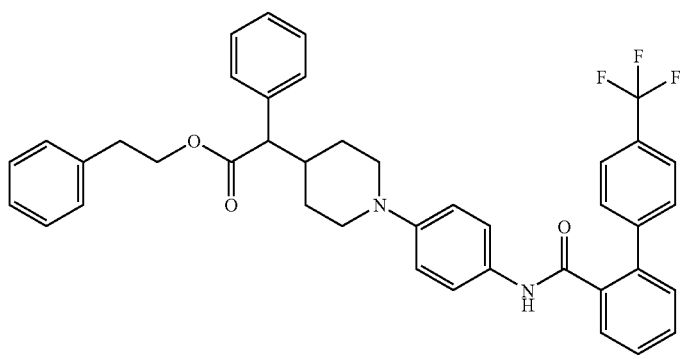
Co. No. 250; Ex. B.25
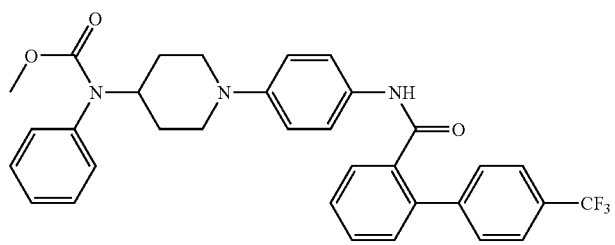
Co. No. 251; Ex. B.27
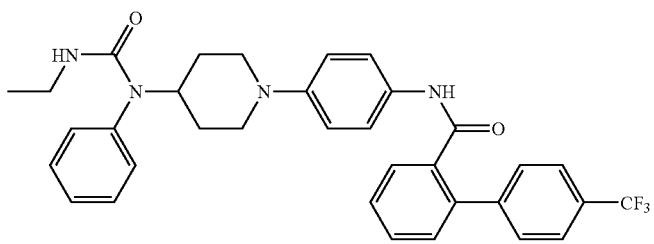
Co. No. 252; Ex. B.27

TABLE F-1-continued
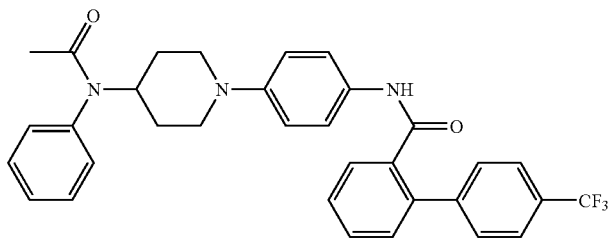
Co. No. 253; Ex. B.26
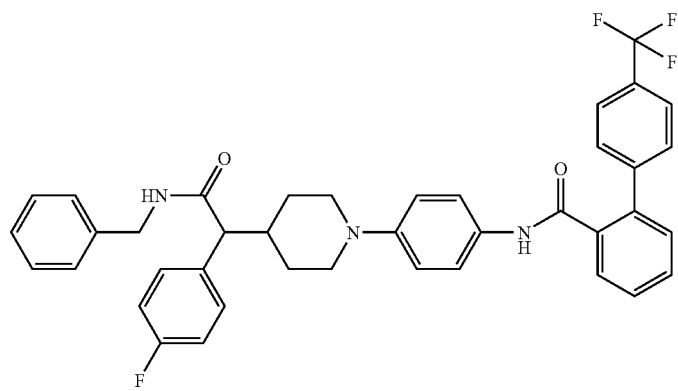
Co. No. 254; Ex. B.2
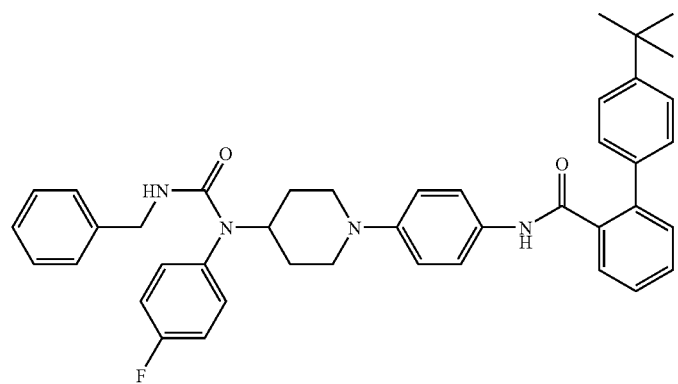
Co. No. 255; Ex. B.2
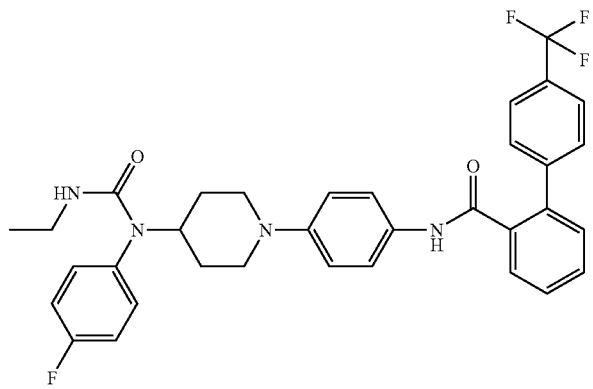
Co. No. 256; Ex. B.2

TABLE F-1-continued
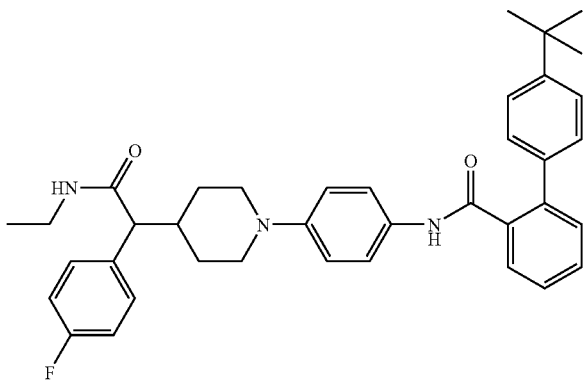
Co. No. 257; Ex. B.2
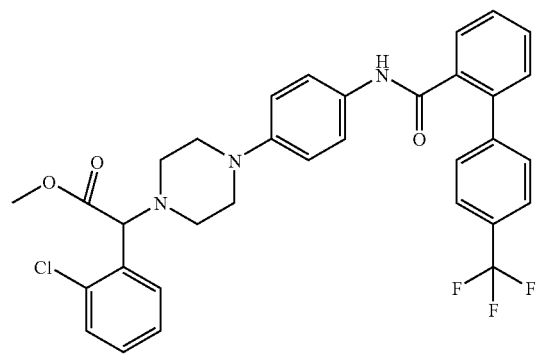
Co. No. 258; Ex. B.9
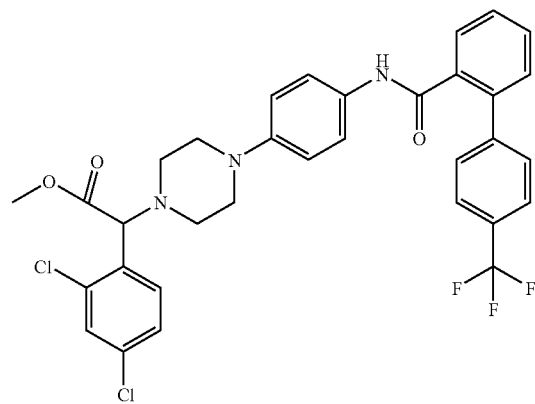
Co. No. 259; Ex. B.9

TABLE F-1-continued
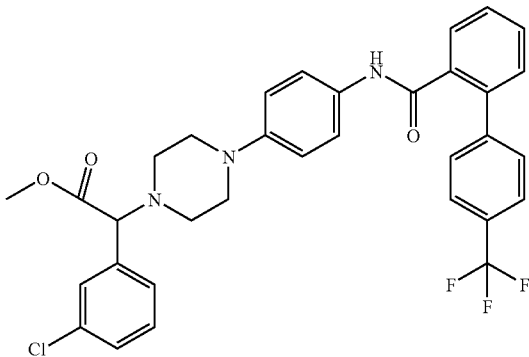
Co. No. 260; Ex. B.9
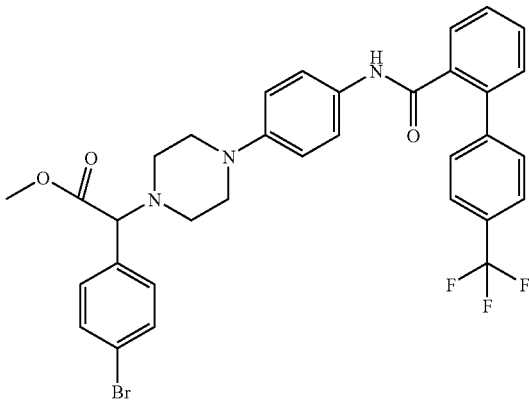
Co. No. 261; Ex. B.9
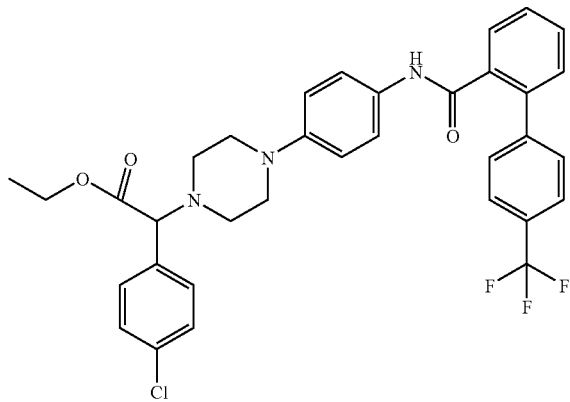
Co. No. 262; Ex. B.9

TABLE F-1-continued
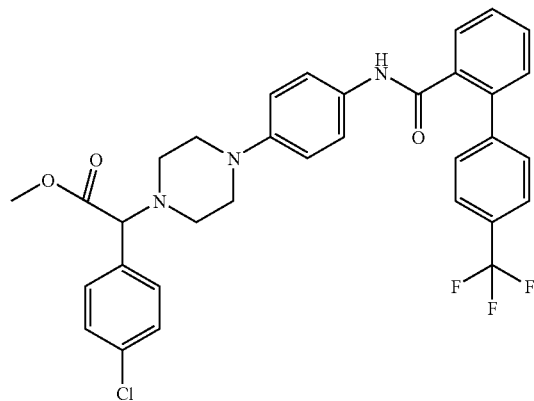
Co. No. 263; Ex. B.9
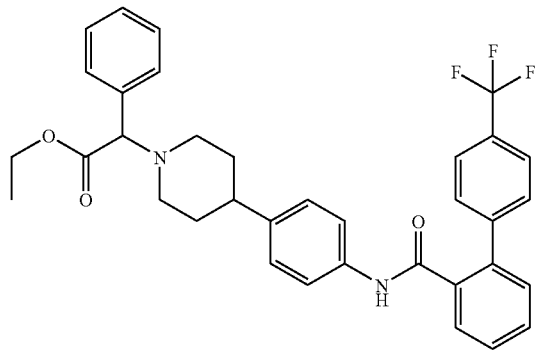
(−); Co. No. 264; Ex. B.24; mp. 147° C.;
$[\alpha]_D^{20} = -18.03°$ (c = 25.51 mg/5 ml in CH$_3$OH)
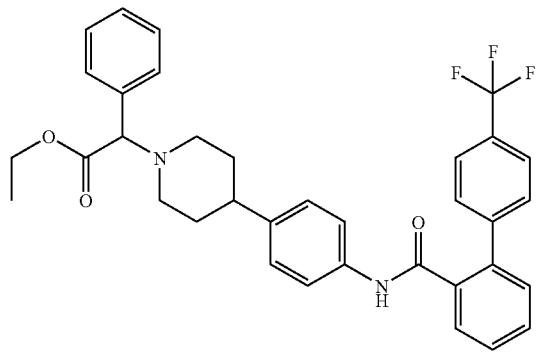
(+); Co. No. 265; Ex. B.24; mp. 142° C.;
$[\alpha]_D^{20} = +15.76°$ (c = 25.70 mg/5 ml in CH$_3$OH)

TABLE F-1-continued
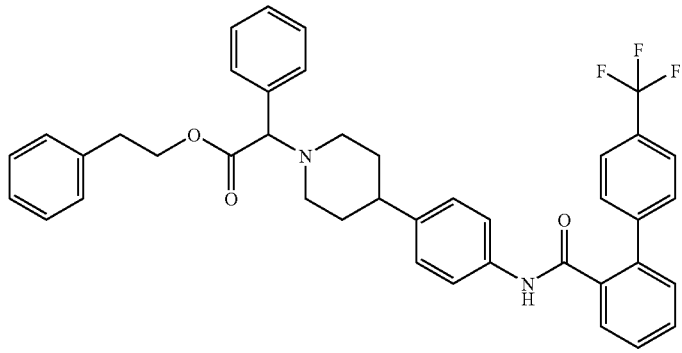
Co. No. 266; Ex. B.24
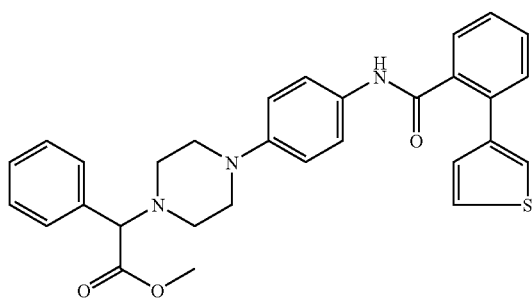
Co. No. 267; Ex. B.29; mp. 150° C.
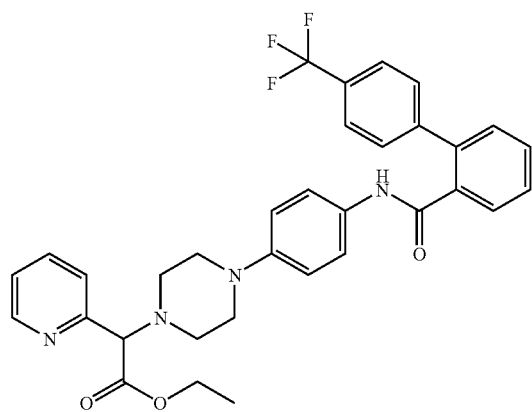
Co. No. 268; Ex. B.9; mp. 114° C.
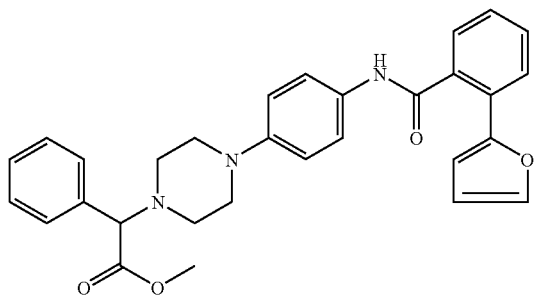
Co. No. 269; Ex. B.29; mp. 90° C.

TABLE F-1-continued
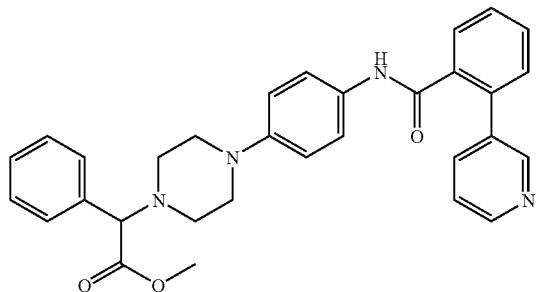
Co. No. 270; Ex. B.30; mp. 194° C.
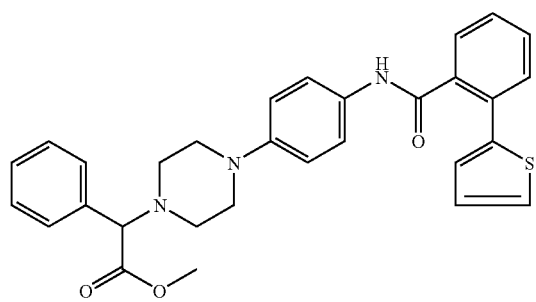
Co. No. 271; Ex. B.29; mp. 60° C.
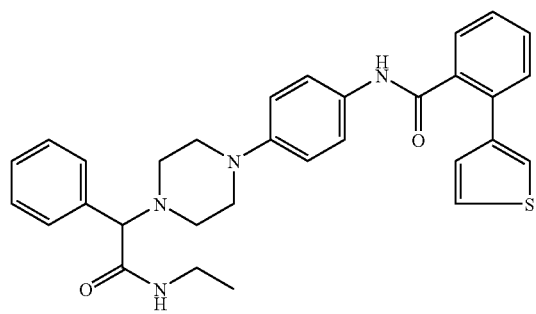
Co. No. 272; Ex. B.28; mp. 114° C.
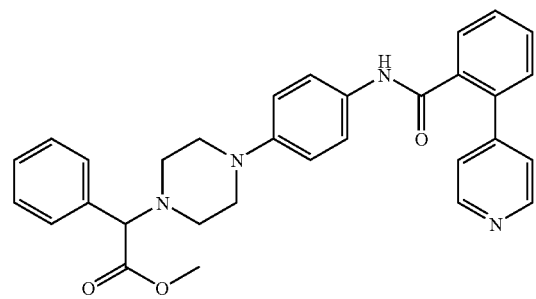
Co. No. 273; Ex. B.30

TABLE F-1-continued

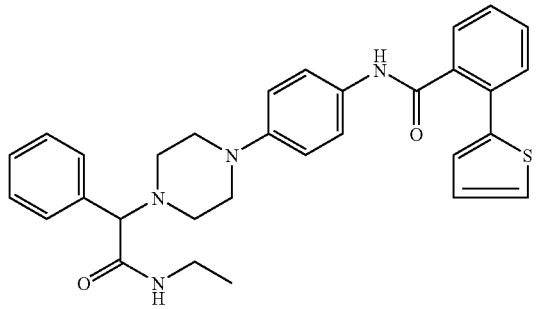

Co. No. 274; Ex. B.28

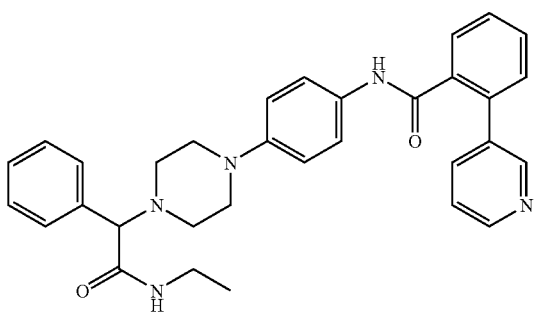

Co. No. 275; Ex. B.28

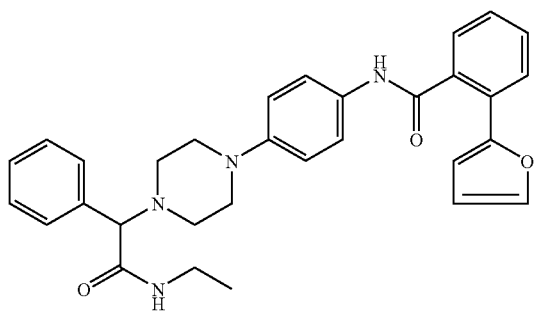

Co. No. 276; Ex. B.28

C. PHARMACOLOGICAL EXAMPLES

C.1. Quantification of the Secretion of ApoB

HepG2 cells were cultured in 24-well plates in Minimal Essential Medium Rega 3 containing 10% fetal calf serum. Rega 3 has the following composition: $CaCl_2$ (264 µg/ml), KCl (400 µg/ml), $MgSO_4.7H_2O$ (200 µg/ml), NaCl (6800 µg/ml), $NaHCO_3$ (850 µg/ml), $NaH_2PO_4.H_2O$ (158 µg/ml), D-glucose (1000 µg/ml), phenol red (10 µg/ml), L-alanine (8.9 µg/ml), L-arginine HCl (12 µg/ml), L-asparagine.$H_2O$ (15 µg/ml), L-aspartic acid (13.3 µg/ml), L-cystine (24 µg/ml), L-glutamic acid (14.7 µg/ml), glycine (7.5 µg/ml), L-histidine.HCl.$H_2O$ (42 µg/ml), L-isoleucine (52 µg/ml), L-leucine (52 µg/ml), L-lysine.HCl (72.5 µg/ml), L-methionine (15 µg/ml), L-phenylalanine (32 µg/ml), L-proline (11.5 µg/ml), L-serine (10.5 µg/ml), L-threonine (48 µg/ml), L-tryptophan (10 µg/ml), L-tyrosine (36 µg/ml), L-valine (46 µg/ml), D-Ca pantothenate (1 µg/ml), choline chloride (1 µg/ml), folic acid (1 µg/ml), 1-enositol (2 µg/ml), nicotinamide (1 µg/ml), pyridoxal HCl (1 µg/ml), riboflavin (0.1 µg/ml) and thiamine HCl (1 µg/ml).

At 70% confluency, the medium was changed and the test compound or carrier (dimethylsulfoxide, 0.4% final concentration) was added. After 24 hours of incubation, the medium was transferred to Eppendorf tubes and cleared by centrifugation. A sheep antibody directed against either apo B was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM 4-morpholinepropanesulfonic acid, 40 mM $NaH_2PO_4$, 100 mM NaF, 0.2 mM dithiothreitol, 5 mM ethylenediamine tetraacetic acid, 5 mM ethylenebis (oxyethylenenitrilo) tetraacetic acid, 1% Triton-X-100, 0.5% sodium deoxycholate, 0.1% sodium dodecylsulphate, 0.2 µM leupeptin and 0.2 µM phenylmethylsulphonylfluoride. Radioactivity in the pellet was quantified by liquid scintillation counting.

Resulting IC$_{50}$ values are enumerated in Table C.1 for a number of compounds No. 1 to No. 123.

TABLE C.1

| Co. No. | pIC$_{50}$ |
|---|---|
| 1 | 8.103 |
| 2 | 6.974 |
| 3 | 7.591 |
| 4 | 5.523 |
| 5 | 6.802 |
| 6 | 6.967 |
| 7 | 6.583 |
| 8 | 7.221 |
| 9 | 6.655 |
| 10 | 6.618 |
| 11 | 8.335 |
| 12 | 6.636 |
| 13 | 7.523 |
| 14 | 5.523 |
| 15 | 6.688 |
| 16 | 7.077 |
| 17 | 6.702 |
| 18 | 6.687 |
| 19 | 6.578 |
| 20 | 6.005 |
| 21 | 6.611 |
| 22 | 6.984 |
| 23 | 5.523 |
| 24 | 6.072 |
| 25 | 6.542 |
| 26 | 6.561 |
| 27 | 5.885 |
| 28 | 6.115 |
| 29 | 5.523 |
| 30 | 6.782 |
| 31 | 5.894 |
| 32 | 5.621 |
| 33 | 5.523 |
| 34 | 5.809 |
| 35 | 5.523 |
| 36 | 7.523 |
| 37 | 7.507 |
| 38 | 8.179 |
| 39 | 7.791 |
| 40 | 7.586 |
| 41 | 7.666 |
| 42 | 5.523 |
| 43 | 5.751 |
| 44 | 5.981 |
| 45 | 5.523 |
| 46 | 6.336 |
| 47 | 6.702 |
| 48 | 6.198 |
| 49 | 6.627 |
| 50 | 7.028 |
| 51 | 7.163 |
| 52 | 6.531 |
| 53 | 8.736 |
| 54 | 8.103 |
| 55 | 7.523 |
| 56 | 7.523 |
| 57 | 8.121 |
| 58 | 7.523 |
| 59 | 7.523 |
| 60 | 7.523 |
| 61 | 8.414 |
| 62 | 7.19 |
| 63 | 6.912 |
| 64 | 6.799 |
| 65 | 6.62 |
| 66 | 7.099 |
| 67 | 6.608 |
| 68 | 7.523 |
| 69 | 8.051 |
| 70 | 7.523 |
| 71 | 7.987 |
| 72 | 7.523 |
| 73 | 8.216 |
| 74 | 7.523 |

TABLE C.1-continued

| Co. No. | pIC$_{50}$ |
|---|---|
| 75 | 7.943 |
| 76 | 7.286 |
| 77 | 7.523 |
| 78 | 7.488 |
| 79 | 7.301 |
| 80 | 6.448 |
| 81 | 6.749 |
| 82 | 7.011 |
| 83 | 7.364 |
| 84 | 7.1 |
| 85 | 6.888 |
| 86 | 7.075 |
| 87 | 8.688 |
| 88 | 7.523 |
| 89 | 6.44 |
| 90 | 7.851 |
| 91 | 8.061 |
| 92 | 7.199 |
| 93 | 7.141 |
| 94 | 7.356 |
| 95 | 7.523 |
| 96 | 7.493 |
| 97 | 6.63 |
| 98 | 7.237 |
| 99 | 7.523 |
| 99 | 8.062 |
| 100 | 7.935 |
| 101 | 6.684 |
| 102 | 7.732 |
| 103 | 7.133 |
| 104 | 8.1 |
| 105 | 7.043 |
| 106 | 6.6 |
| 107 | 6.535 |
| 108 | 6.725 |
| 109 | 5.833 |
| 110 | 6.8 |
| 111 | 6.655 |
| 112 | 6.363 |
| 113 | 6.938 |
| 114 | 6.078 |
| 115 | 5.766 |
| 116 | 6.414 |
| 117 | 6.916 |
| 118 | 6.895 |
| 119 | 6.757 |
| 120 | 6.447 |
| 121 | 5.676 |
| 122 | 6.383 |
| 123 | 6.618 |
| 129 | 5.557 |
| 130 | 6.444 |
| 131 | 6.38 |
| 132 | 7.299 |
| 133 | <5.523 |
| 134 | 7.185 |
| 135 | 6.826 |
| 136 | 6.829 |
| 137 | 5.752 |
| 138 | 7.003 |
| 139 | 7.065 |
| 140 | 7.693 |
| 141 | 7.601 |
| 142 | 6.944 |
| 143 | 6.631 |
| 144 | 6.695 |
| 145 | 6.732 |
| 146 | 6.467 |
| 147 | 6.542 |
| 148 | 7.219 |
| 149 | 7.38 |
| 150 | 6.761 |
| 151 | 6.213 |
| 152 | 7.025 |
| 153 | 5.809 |
| 154 | 5.634 |
| 156 | 6.915 |

TABLE C.1-continued

| Co. No. | pIC$_{50}$ |
|---|---|
| 157 | 6.97 |
| 158 | 7.671 |
| 159 | 6.973 |
| 160 | 7.489 |
| 161 | 7.162 |
| 162 | 7.015 |
| 163 | 6.602 |
| 164 | 7 |
| 165 | 7.482 |
| 166 | 7.444 |
| 167 | >7.523 |
| 168 | 6.881 |
| 174 | 7.035 |
| 175 | >7.523 |
| 176 | 6.873 |
| 177 | 6.583 |
| 178 | 7.465 |
| 179 | 6.395 |
| 180 | 6.945 |
| 181 | 8.48 |
| 182 | 8.118 |
| 183 | 7.666 |
| 184 | 8.505 |
| 185 | 7.312 |
| 186 | 6.698 |
| 187 | 7.386 |
| 188 | 8 |
| 189 | 6.979 |
| 190 | 8.193 |
| 191 | 8.143 |
| 192 | 6.802 |
| 193 | 6.629 |
| 194 | 7.367 |
| 195 | 7.047 |
| 196 | 6.999 |
| 197 | 7.783 |
| 198 | 7.136 |
| 200 | 7.096 |
| 201 | >7.523 |
| 202 | 6.736 |
| 203 | 8.333 |
| 204 | 6.369 |
| 205 | 7.323 |
| 206 | 6.106 |
| 207 | >7.523 |
| 208 | 8.126 |
| 209 | 8.099 |
| 210 | 6.316 |
| 211 | 7.702 |
| 212 | >7.523 |
| 213 | >7.523 |
| 214 | >7.523 |
| 215 | >7.523 |
| 216 | 7.327 |
| 217 | 5.57 |
| 218 | >7.523 |
| 219 | 7.105 |
| 220 | >7.523 |
| 221 | >7.523 |
| 222 | 7.716 |
| 223 | 6.432 |
| 224 | 6.254 |
| 225 | 7.17 |
| 227 | 6.727 |
| 229 | 7.409 |
| 230 | 8.31 |
| 231 | >7.523 |
| 232 | >7.523 |
| 233 | >7.523 |
| 234 | >7.523 |
| 235 | >7.523 |
| 236 | 7.663 |
| 237 | >7.523 |
| 238 | 7.824 |
| 239 | 7.855 |
| 240 | 7.982 |
| 241 | 7.578 |
| 242 | 8.133 |
| 243 | >7.523 |
| 245 | 6.28 |
| 246 | 6.762 |
| 247 | <5.523 |
| 248 | 7.164 |
| 249 | <5.523 |
| 250 | 6.632 |
| 251 | 8.016 |
| 252 | 7.915 |
| 253 | 6.887 |
| 254 | 7.541 |
| 255 | 8.298 |
| 256 | 7.821 |
| 257 | 7.857 |
| 258 | 6.856 |
| 259 | 6.377 |
| 260 | >7.523 |
| 261 | 6.129 |
| 262 | 6.253 |
| 263 | 6.555 |
| 266 | 7.591 |

C.2. MTP Assay

MTP activity was measured using an assay similar to one described by J. R. Wetterau and D. B. Zilversmit in *Chemistry and Physics of Lipids* (1985) 38, 205–222. In order to prepare the donor and acceptor vesicles, the appropriate chloroform were put into a glass test tube and dried under a stream of nitrogen. A buffer containing 15 mM Tris-HCl (pH 7.5), 1 mM ethylenediamine tetra-acetic acid, 40 mM NaCl, 0.02% NaN$_3$ (assay buffer) was added to the dried lipid. The mixture was vortexed briefly and the lipids were then allowed to hydrate for 20 minutes on ice. Vesicles were then prepared by bath sonication (using a Branson 2200 device) at room temperature for at most 15 minutes. Butylated hydroxytoluene was included in all vesicle preparations at a concentration of 0.1%. The lipid transfer assay mixture contained donor vesicles (40 nmole phosphatidylcholine, 7.5 mole % cardiolipin and 0.25 mole % glycerol tri[1-$^{14}$C]-oleate), acceptor vesicles (240 nmol phosphatidylcholine) and 5 mg bovine serum albumin in a total volume of 675 µl in a 1.5 ml microcentrifuge tube. Test compounds were added dissolved in dimethylsulfoxide (0.13% final concentration). After 5 minutes of pre-incubation at 37° C., the reaction was started by the addition of MTP in 100 µl of a dialysis buffer. The reaction was stopped by the addition of 400 µl diethylaminoalkyl (DEAE)-52 cellulose (Sephadex) pre-equilibrated in 15 mM Tris-HCl (pH 7.5), 1 mM ethylenediamine tetra-acetic acid and 0.02% NaN$_3$ (11:1 volume/volume). The mixture was agitated for 4 minutes and centrifuged for 2 minutes at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

Resulting IC$_{50}$ values are enumerated in Table C.2 for some of the above-referred compounds.

TABLE C.2

| Co. No. | pIC$_{50}$ |
|---|---|
| 1 | 7.864 |
| 3 | 7.735 |
| 6 | 6.703 |
| 7 | 6.44 |
| 10 | <5.523 |
| 11 | 8.136 |
| 16 | 6.682 |
| 39 | 7.922 |
| 40 | 8.344 |
| 41 | 8.063 |
| 54 | 8.269 |
| 55 | 8.37 |
| 57 | 8.163 |
| 58 | 7.799 |
| 60 | 8.082 |
| 61 | 8.32 |
| 62 | 7.98 |
| 75 | 8.077 |
| 87 | 8.495 |
| 199 | 8.334 |
| 203 | 8.682 |
| 222 | 8.075 |
| 229 | 7.279 |
| 230 | 8.439 |
| 232 | 7.602 |
| 239 | 8.703 |
| 241 | 7.985 |
| 242 | 7.94 |
| 264 | 7.497 |
| 265 | 8.25 |

The invention claimed is:

1. Polyarylcarboxamide compounds of formula (I)

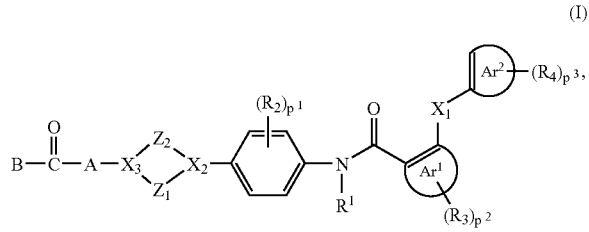

the N-oxides, the pharmaceutically acceptable addition salts and the stereochemically isomeric forms thereof, wherein
$Z_1$ is $(CH_2)_n$ wherein n is 2;
$Z_2$ is $(CH_2)_m$ wherein m is 2;
$X_1$ represents O, $CH_2$, CO, NH, $CH_2O$, $OCH_2$, $CH_2S$, $SCH_2$ or a direct bond;
$X_2$ is CH and $X_3$ is N;
$R_1$ is hydrogen or $C_{1-4}$alkyl;
$Ar^1$ is optionally substituted with one or two $R_3$ substituents;
$Ar^2$ is an aromatic ring selected from phenyl, naphthalenyl, pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl and thienyl, optionally substituted with one, two or three $R_4$ substituents;
each $R_2$ and $R_3$ is independently selected from $C_{1-4}$alkyl, $C_{1-4}$alkyloxy, halo and trifluoromethyl;
each $R_4$ is independently selected from $C_{1-4}$alkyl, $C_{1-4}$alkyloxy, halo, hydroxy, mercapto, cyano, nitro, $C_{1-4}$alkylthio or polyhalo$C_{1-6}$alkyl, amino, $C_{1-4}$alkylamino and di($C_{1-4}$alkyl)amino;
$p^1$ and $p^2$ are each 0 to 2;
$p^3$ is 0 to 3;
$X_1$ and $R_4$ taken together with the aromatic rings $Ar^1$ and $Ar^2$ to which they are attached may form a fluoren-1-yl or a fluoren-4-yl group;
A represents a $C_{1-6}$alkanediyl substituted with one or two groups selected from aryl, heteroaryl, and $C_{3-10}$cycloalkyl;
B represents hydrogen; $C_{1-10}$alkyl; aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkoxycarbonyl, $C_{1-10}$alkylaminocarbonyl and di($C_{1-10}$alkyl)aminocarbonyl; aryl$C_{1-6}$alkyl; heteroaryl$C_{1-10}$alkyl; $C_{3-10}$cycloalkyl; polyhalo$C_{1-6}$alkyl; $C_{3-6}$alkenyl; $C_{3-6}$alkynyl; $NR_6R_7$; or $OR_8$;
$R_6$ and $R_7$ each independently represent hydrogen, $C_{1-10}$alkyl, aryl or heteroaryl each optionally substituted with a group selected from halo, cyano, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl, heteroaryl$C_{1-10}$alkyl, $C_{3-10}$cycloalkyl, $C_{7-10}$polycycloalkyl, polyhalo$C_{1-6}$alkyl, $C_{3-8}$alkenyl, $C_{3-8}$alkynyl, fused benzo-$C_{5-8}$cycloalkyl, and wherein $R_6$ and $R_7$ taken together with the nitrogen atom to which they are attached may form a $C_{4-8}$ saturated heterocyclic radical;
$R_8$ represents $C_{1-10}$alkyl, aryl or heteroaryl each optionally substituted with a group selected from halo, cyano, nitro, $C_{1-4}$alkyloxy, amino, $C_{1-10}$alkylamino, di($C_{1-10}$alkyl)amino, $C_{1-10}$acyl, $C_{1-10}$alkylthio, $C_{1-10}$alkylaminocarbonyl and di($C_{1-10}$alkyl)aminocarbonyl; aryl$C_{1-10}$alkyl; heteroaryl$C_{1-10}$alkyl; and $C_{3-10}$cycloalkyl; $C_{7-10}$polycycloalkyl; polyhalo$C_{1-6}$alkyl; $C_{3-8}$alkenyl; $C_{3-8}$alkynyl; or fused benzo-$C_{5-8}$cycloalkyl.

2. Polyarylcarboxamide compounds according to claim 1 wherein $X_1$ is a direct bond.

3. Polyarylcarboxamide compounds according to claims 1 wherein $p^1$ and $p^2$ are each 0 and $R_4$ is trifluoromethyl, chloro or tert-butyl.

4. A pharmaceutical composition comprising at least one pharmaceutically acceptable carrier and a therapeutically effective amount of a compound according to claim 1.

5. A pharmaceutical composition according to claim 4, further comprising at least one additional lipid-lowering agent.

* * * * *